(12) United States Patent  
Christianson et al.

(10) Patent No.: US 10,786,351 B2  
(45) Date of Patent: Sep. 29, 2020

(54) PROSTHETIC MITRAL VALVES AND APPARATUS AND METHODS FOR DELIVERY OF SAME

(71) Applicant: Tendyne Holdings, Inc., Roseville, MN (US)

(72) Inventors: Mark Christianson, Plymouth, MN (US); Zachary Vidlund, Robbinsdale, MN (US); Robert Vidlund, Forest Lake, MN (US); Igor Kovalsky, Minnetonka, MN (US); William Peckels, St. Paul, MN (US); Michael Evans, Minneapolis, MN (US); Chad Perrin, Andover, MN (US); John F. Otte, Minneapolis, MN (US); Son Mai, Centerville, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 11 days.

(21) Appl. No.: 15/626,607

(22) Filed: Jun. 19, 2017

(65) Prior Publication Data

US 2017/0281343 A1 Oct. 5, 2017

Related U.S. Application Data

(63) Continuation of application No. PCT/US2016/012305, filed on Jan. 6, 2016, which is (Continued)

(51) Int. Cl.  
*A61F 2/24* (2006.01)

(52) U.S. Cl.  
CPC .......... *A61F 2/2418* (2013.01); *A61F 2/246* (2013.01); *A61F 2/2436* (2013.01); (Continued)

(58) Field of Classification Search  
CPC ............................ A61F 2/2409; A61F 2/2418  
See application file for complete search history.

(56) References Cited

U.S. PATENT DOCUMENTS 2,697,008 A 12/1954 Rowley  
3,409,013 A 11/1968 Berry  
(Continued)

FOREIGN PATENT DOCUMENTS

CN 1486161 3/2004  
CN 1961845 A 5/2007  
(Continued)

OTHER PUBLICATIONS

US 9,155,620 B2, 10/2015, Gross et al. (withdrawn)  
(Continued)

*Primary Examiner* — Leslie Lopez  
(74) *Attorney, Agent, or Firm* — Lerner, David, Littenberg, Krumholz & Mentlik, LLP

(57) ABSTRACT

Apparatus and methods are described herein for use in the transvascular delivery and deployment of a prosthetic mitral valve. In some embodiments, a method includes inverting an outer frame of a prosthetic mitral valve when the valve is in a biased expanded configuration. After inverting the outer frame, the prosthetic mitral valve is inserted into a lumen of a delivery sheath such that the mitral valve is moved to a collapsed configuration. The distal end portion of the delivery sheath is inserted into a left atrium of a heart. The prosthetic mitral valve is moved distally out of the delivery sheath such that the inverted outer frame reverts and the prosthetic mitral valve assumes its biased expanded configuration. In some embodiments, actuation wires are used to assist in the reversion of the outer frame. The prosthetic mitral valve is then positioned within a mitral annulus of the heart.

26 Claims, 73 Drawing Sheets

Related U.S. Application Data a continuation-in-part of application No. PCT/US2015/014572, filed on Feb. 5, 2015.

(60) Provisional application No. 62/100,548, filed on Jan. 7, 2015, provisional application No. 62/187,896, filed on Jul. 2, 2015, provisional application No. 62/137,384, filed on Mar. 24, 2015.

(52) U.S. Cl.
CPC .......... *A61F 2/2439* (2013.01); *A61F 2/2457* (2013.01); *A61F 2220/0016* (2013.01); *A61F 2220/0041* (2013.01); *A61F 2220/0075* (2013.01); *A61F 2220/0083* (2013.01); *A61F 2230/0093* (2013.01); *A61F 2250/0039* (2013.01); *A61F 2250/0063* (2013.01); *A61F 2250/0098* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |

(56) References Cited

U.S. PATENT DOCUMENTS

| | | | |
|---|---|---|---|
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,361,137 B2 | 4/2008 | Taylor et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |

(56) References Cited

U.S. PATENT DOCUMENTS

| | | |
|---|---|---|
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,961,597 B2 | 2/2015 | Subramanian et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,468,526 B2 | 10/2016 | Subramanian et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,848,880 B2 | 12/2017 | Coleman et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,016,271 B2 | 7/2018 | Morriss et al. |
| 10,226,334 B2 | 3/2019 | Rowe et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0069593 A1 | 4/2003 | Tremulis et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049211 A1 | 3/2004 | Tremulis et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0210304 A1 | 10/2004 | Seguin et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |

(56) References Cited

U.S. PATENT DOCUMENTS

| | | |
|---|---|---|
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0074484 A1 | 4/2006 | Huber |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0109069 A1 | 5/2008 | Coleman et al. |
| 2008/0114442 A1 | 5/2008 | Mitchell et al. |
| 2008/0125861 A1 | 5/2008 | Webler et al. |
| 2008/0140189 A1 | 6/2008 | Nguyen et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |

(56) References Cited

U.S. PATENT DOCUMENTS

| | | |
|---|---|---|
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0004740 A1 | 1/2010 | Seguin et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0121435 A1 | 5/2010 | Subramanian et al. |
| 2010/0121437 A1 | 5/2010 | Subramanian et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280589 A1* | 11/2010 | Styrc .................. A61F 2/2412 623/1.12 |
| 2010/0280604 A1 | 11/2010 | Zipory et al. |
| 2010/0280604 A1 | 11/2010 | Alkhatib |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0213459 A1 | 9/2011 | Garrison et al. |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0010700 A1 | 1/2012 | Spenser |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0109079 A1 | 5/2012 | Asleson et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0245678 A1 | 9/2012 | Solem |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0103140 A1 | 4/2013 | Subramanian et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0226290 A1 | 8/2013 | Yellin et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1 | 11/2013 | McLean et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0338764 A1 | 12/2013 | Thornton et al. |
| 2014/0005778 A1 | 1/2014 | Buchbinder et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243965 A1 | 8/2014 | Benson et al. |
| 2014/0243966 A1 | 8/2014 | Garde et al. |
| 2014/0257466 A1* | 9/2014 | Board .................. A61F 2/2403 623/2.11 |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358222 A1 | 12/2014 | Gorman, III et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |

(56) References Cited

U.S. PATENT DOCUMENTS

| | | |
|---|---|---|
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0223935 A1 | 8/2015 | Subramanian et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100245 A1 | 4/2017 | Subramanian et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102791223 A | 11/2012 |
| CN | 102869317 | 1/2013 |
| CN | 102869318 | 1/2013 |
| CN | 102869321 | 1/2013 |
| CN | 103220993 | 7/2013 |
| CN | 103974674 A | 8/2014 |
| CN | 102639179 B | 10/2014 |
| DE | 2246526 A1 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2005515836 A | 6/2005 |
| JP | 2009-514628 | 4/2009 |
| JP | 2009519783 A | 5/2009 |
| JP | 2013512765 A | 4/2013 |
| JP | 2014532457 A | 12/2014 |
| NL | 1017275 | 8/2002 |
| SU | 1271508 A1 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | 2006064490 A1 | 6/2006 |
| WO | WO 2006/070372 | 7/2006 |
| WO | 2006105009 A1 | 10/2006 |
| WO | WO 2006/113906 | 10/2006 |
| WO | WO 2006/127756 | 11/2006 |
| WO | WO 2007/081412 | 7/2007 |
| WO | 2007100408 A2 | 9/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |

(56) References Cited

FOREIGN PATENT DOCUMENTS

| WO | WO 2011/072084 | 6/2011 |
|---|---|---|
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/028387 | 2/2013 |
| WO | WO 2013/045262 | 4/2013 |
| WO | WO 2013/059747 | 4/2013 |
| WO | 2013096757 A1 | 6/2013 |
| WO | WO 2013/096411 | 6/2013 |
| WO | 2013116785 A1 | 8/2013 |
| WO | WO 2013/175468 | 11/2013 |
| WO | WO 2014/121280 | 8/2014 |
| WO | 2014138284 A1 | 9/2014 |
| WO | 2014144020 A1 | 9/2014 |
| WO | WO 2014/144937 | 9/2014 |
| WO | WO 2014/162306 | 10/2014 |
| WO | WO 2014/189974 | 11/2014 |
| WO | 2014194178 A1 | 12/2014 |
| WO | WO 2014/210124 | 12/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |
| WO | WO 2017/218375 | 12/2017 |
| WO | WO 2018/005779 | 1/2018 |
| WO | WO 2018/013515 | 1/2018 |

OTHER PUBLICATIONS

International Search Report and Written Opinion for International Application No. PCT/US2016/012305, dated Aug. 3, 2016, 18 pages.
Al Zaibag, M. et al., "Percutaneous Balloon Valvotomy in Tricuspid Stenosis," British Heart Journal, Jan. 1987, 57(1):51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R. et al., "Transluminal implantation of artificial heart valves. Description of a new expandable aortic valve and initial results with implantation by catheter technique in closed chest pigs," European Heart Journal, 1992, 13(5):704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Bernacca, G. M. et al., "Polyurethane heart valves: Fatigue failure, calcification, and polyurethane structure," Journal of Biomedical Materials Research, Mar. 5, 1997, 34(3):371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive CardioVascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html> , Dec. 10, 2012, 5 pages.
Gray, H., The Heart, Anatomy of the Human Body, 1918, Retrieved from the Internet <http://education.yahoo.com/reference/gray/subjects/subject/138> , Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-arteries-gets-a-faili...,>, published Jan. 3, 1991, retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, G. et al., "Mitral Valved Stent Implantation," European Journal of Cardio-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2):194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11):173-174.

(56) References Cited

OTHER PUBLICATIONS

Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Intery Radiol., Jul. 2003, 4:841-853.
Ross, D. N., "Aortic Valve Surgery," Guy's Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, J. B., "Experience with New Retrieval Forceps for Foreign Body Removal in the Vascular, Urinary, and Biliary Systems," Radiology, 1990, 176:535-538.
Serruys, P. W. et al., "Stenting of Coronary Arteries. Are we the Sorcerer's Apprentice?," European Heart Journal, Sep. 1989, 10(9):774-782.
"Shape Memory Alloys," Retrieved from the Internet: <http://webdocs.cs.ualberta.ca/~database/MEMS/sma.html>, Feb. 5, 2016, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, B. T. et al., "Modifications of Gianturco Expandable Wire Stents," Am. J. Roentgenol., May 1988, 150(5):1185-1187.
Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.
Webb, J. G. et al., "Percutaneous Aortic Valve Implantation Retrograde from the Femoral Artery," Circulation, 2006, 113:842-850.
Wheatley, D. J., "Valve Prostheses," Rob & Smith's Operative Surgery, Fourth Edition, 1986, pp. 415-424, Butterworths.
Yoganathan, A. P. et al., "The Current Status of Prosthetic Heart Valves," In Polymetric Materials and Artificial Organs, American Chemical Society, 1984, pp. 111-150.
Cullen, et al., "Transvenous, Antegrade Melody Valve-in-Valve Implantation for Bioprosthetic Mitral and Tricuspid Valve Dysfunction", JACC: Cardiovascular Interventions, vol. 6, No. 6, Jun. 2013, pp. 598-605.

\* cited by examiner

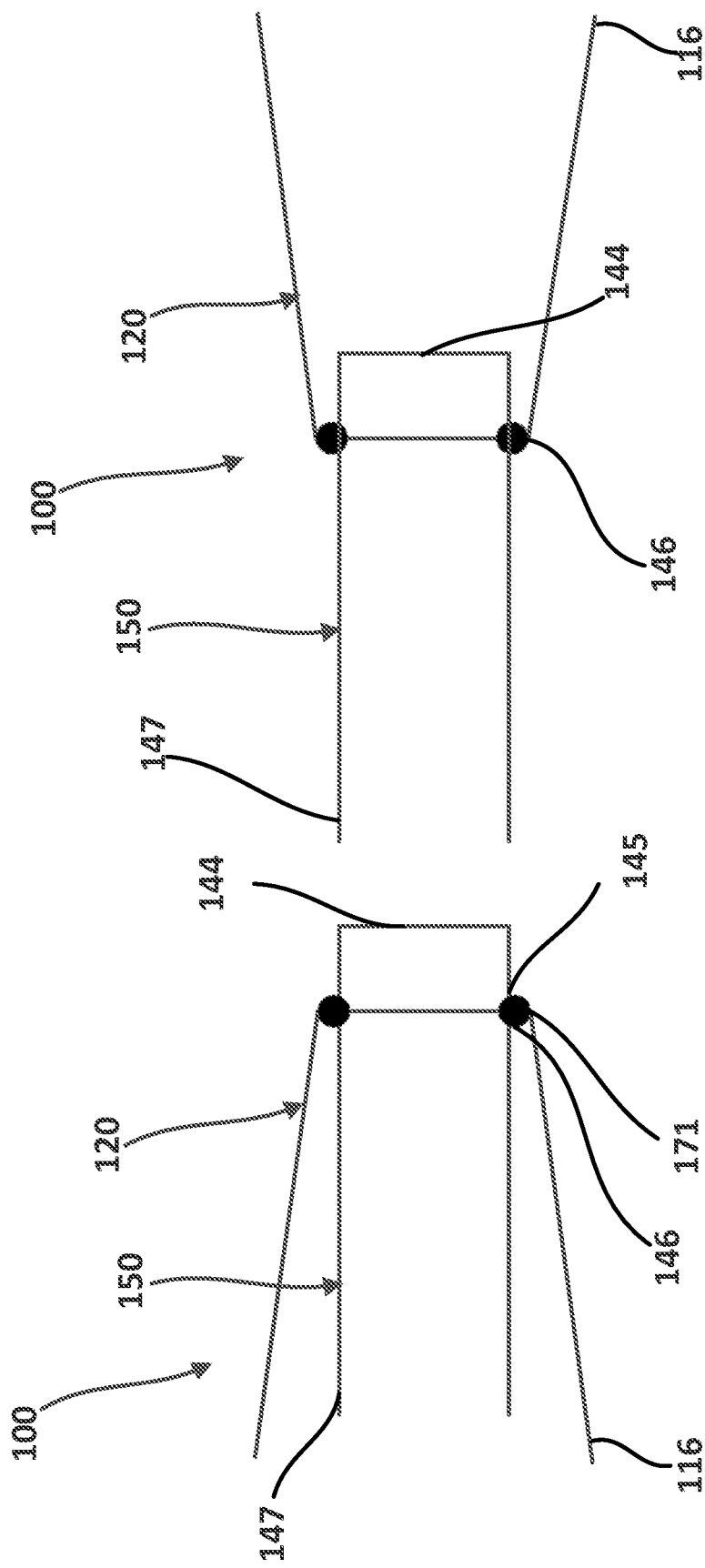

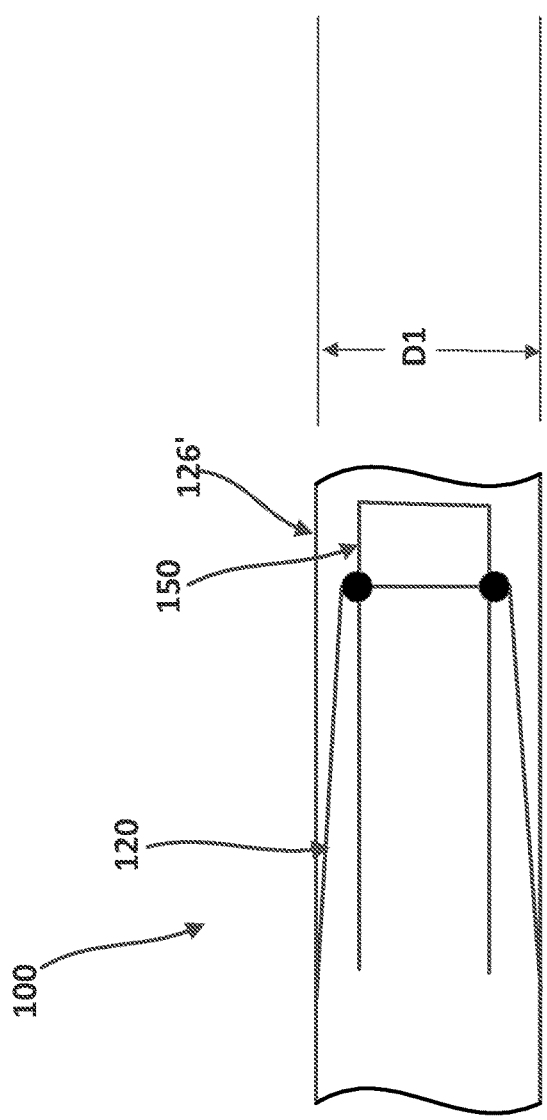
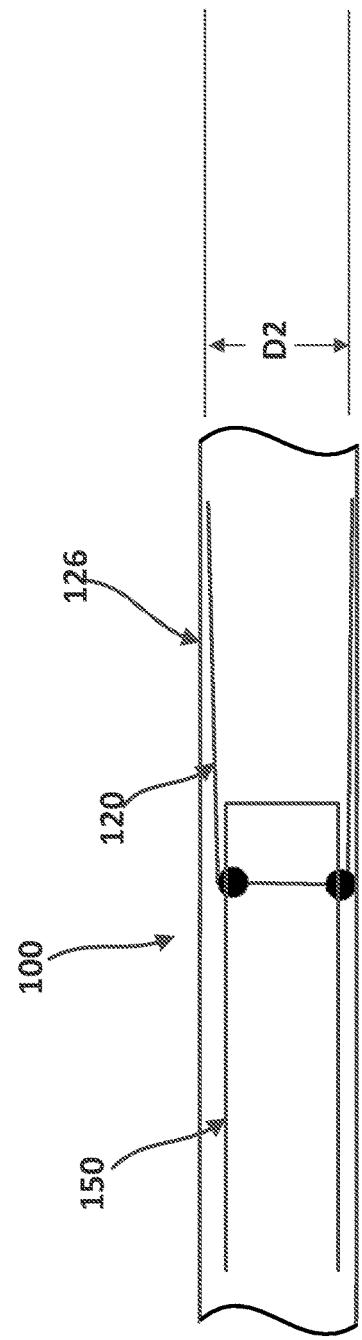

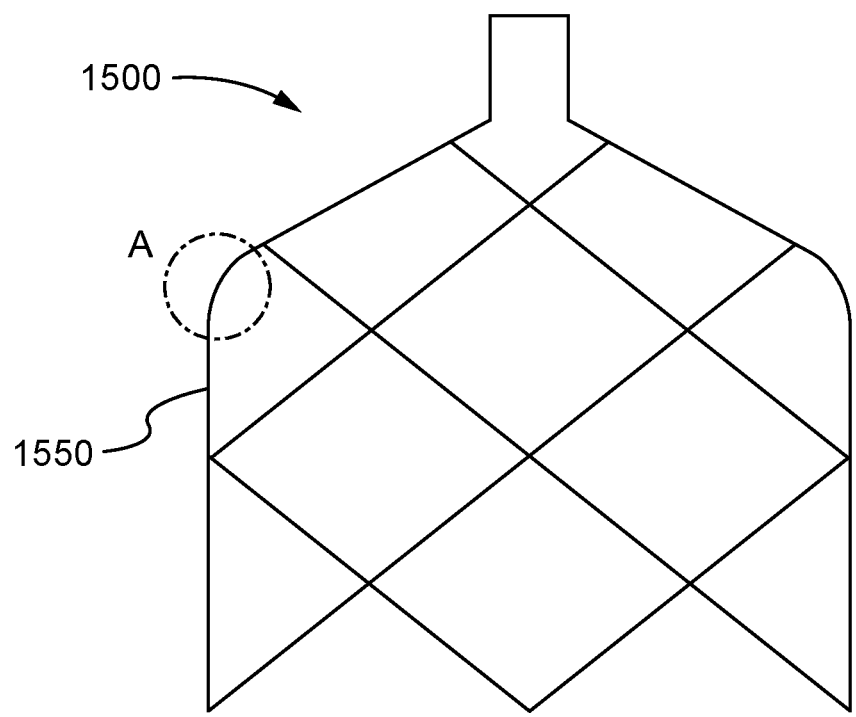
FIG. 41A
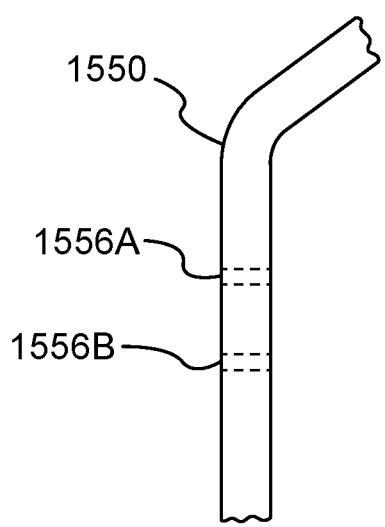 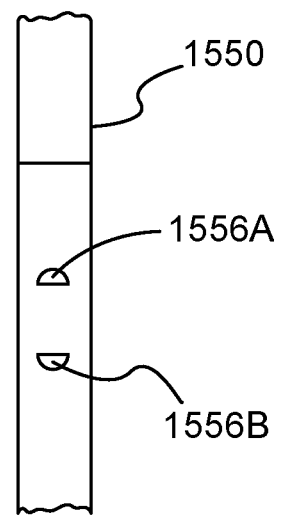
FIG. 41B  FIG. 41C

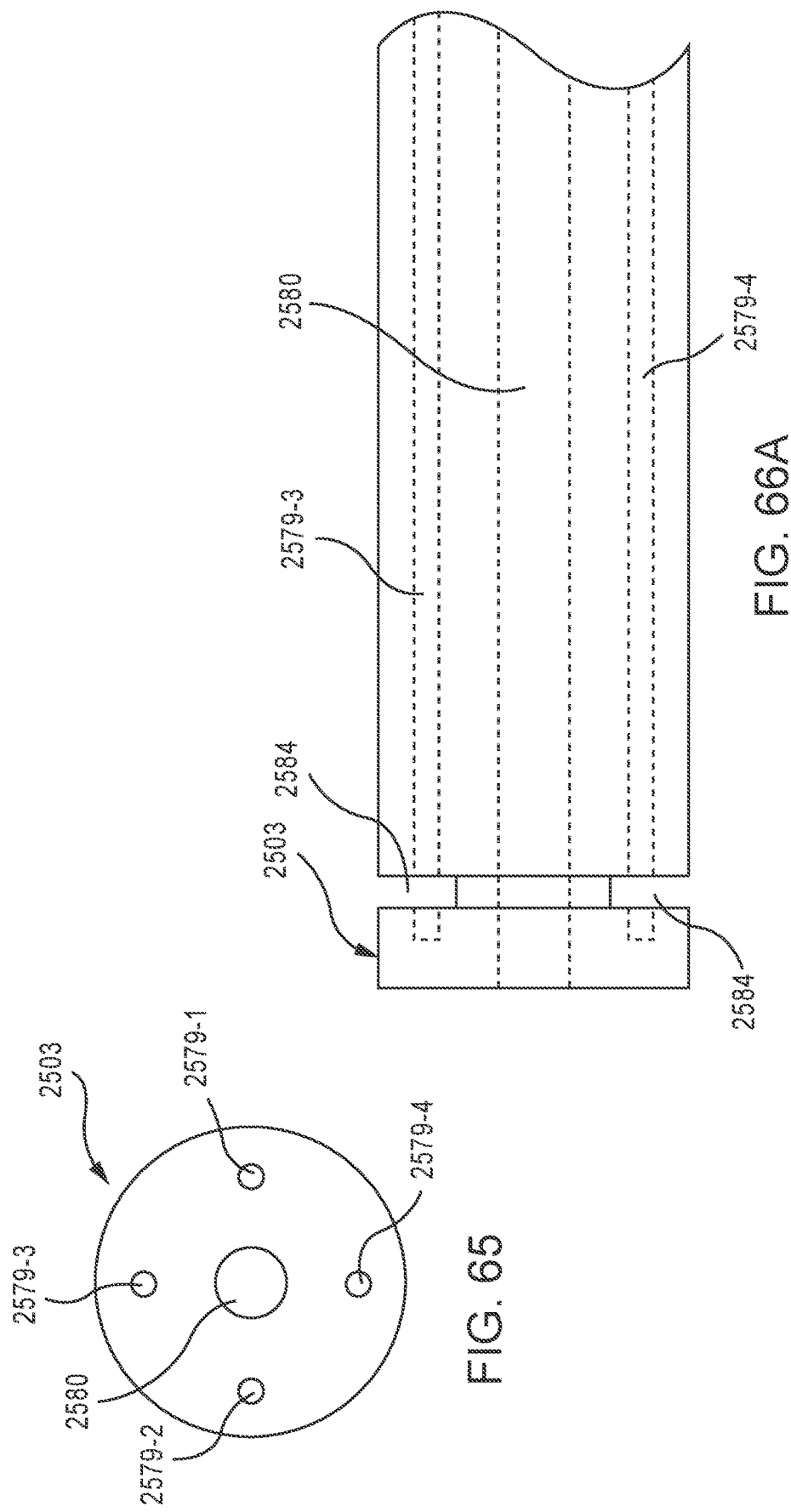

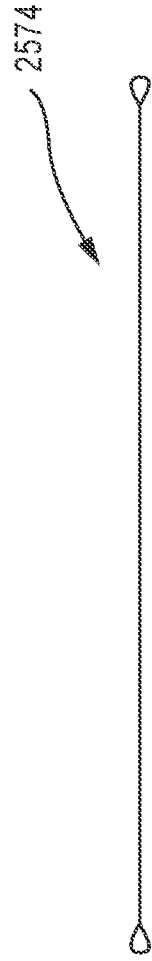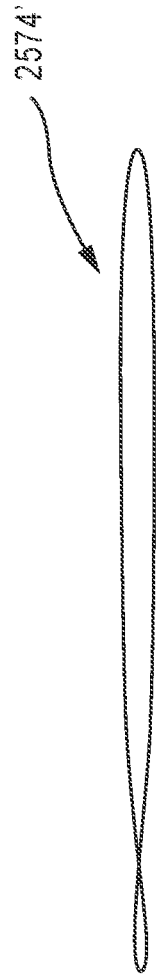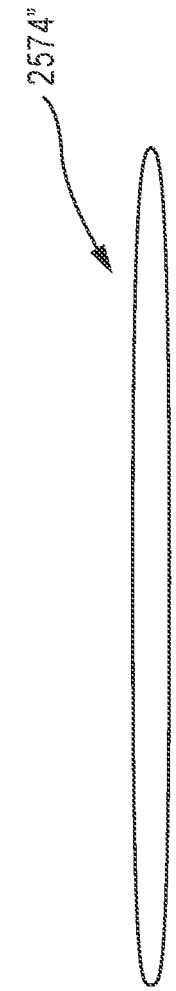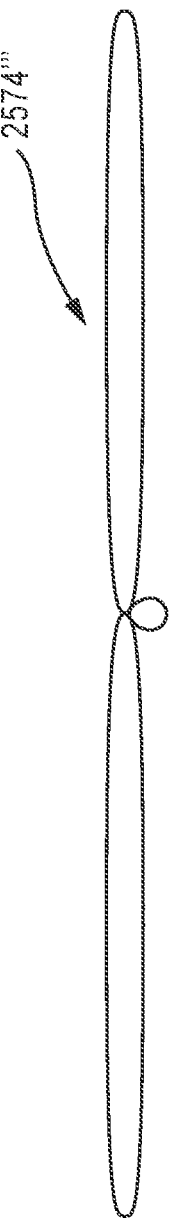

PROSTHETIC MITRAL VALVES AND APPARATUS AND METHODS FOR DELIVERY OF SAME

CROSS-REFERENCE TO RELATED APPLICATIONS

This application is a continuation of International Application No. PCT/US2016/012305, filed on Jan. 6, 2016, which claims priority to and is a continuation-in-part of International Application No. PCT/US15/14572, entitled "Apparatus and Methods for Transfemoral Delivery of Prosthetic Valve," filed Feb. 5, 2015, which claims priority to and the benefit of U.S. Provisional Patent Application Ser. No. 61/935,899, entitled "Transfemoral Delivery of Prosthetic Mitral Valve," filed Feb. 5, 2014, and U.S. Provisional Patent Application No. 62/100,548, entitled "Apparatus and Methods for Transfemoral Delivery of Prosthetic Mitral Valve," filed Jan. 7, 2015. The disclosure of each of the foregoing applications is incorporated herein by reference in its entirety.

International Application No. PCT/US2016/012305 also claims priority to and the benefit of U.S. Provisional Patent Application No. 62/100,548, entitled "Apparatus and Methods for Transfemoral Delivery of Prosthetic Mitral Valve," filed Jan. 7, 2015. The disclosure of which is incorporated herein by reference in its entirety.

International Application No. PCT/US2016/012305 also claims priority to and the benefit of U.S. Provisional Patent Application Ser. No. 62/187,896, entitled "Apparatus and Methods for Delivery of a Prosthetic Mitral Valve," filed Jul. 2, 2015, and U.S. Provisional Patent Application Ser. No. 62/137,384, entitled "Apparatus and Method for Delivery of a Prosthetic Mitral Valve," filed Mar. 24, 2015. The disclosure of each of the foregoing applications is incorporated herein by reference in its entirety.

BACKGROUND

Embodiments are described herein that relate to devices and methods for use in the delivery and deployment of prosthetic valves, and particularly to devices and methods for prosthetic heart valves that provide for delivery of the prosthetic heart valves to within a heart of a patient in an inverted configuration.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

Some known delivery methods include delivering a prosthetic mitral valve through an apical puncture site. In such a procedure, the valve is placed in a compressed configuration within a lumen of a delivery catheter of, for example, 34-36 Fr (i.e. an outer diameter of about 11-12 mm). Delivery of a prosthetic valve to the atrium of the heart can be accomplished, for example, via a transfemoral approach, transatrially directly into the left atrium of the heart or via a jugular approach. In such cases, it is desirable for the prosthetic valve to have a small outer perimeter or profile to allow insertion through a smaller delivery catheter of, for example, 28 Fr (i.e. an outer diameter of about 9 mm). Thus, a need exist for prosthetic heart valves that can have a small profile during delivery while still maintaining the size and characteristics needed to perform their desired function within the heart.

Thus, a need exist for prosthetic heart valves that can have a small profile during delivery while still maintaining the size and characteristics needed to perform their desired function within the heart.

A need also exists for devices and methods for delivering and deploying a prosthetic heart valve within a heart, with the valve disposed within a small diameter delivery sheath and then moving the valve to an expanded configuration within the heart.

SUMMARY

Apparatus and methods are described herein for various embodiments of a prosthetic heart valve that can be moved to an inverted configuration for delivery of the prosthetic heart valve to within a patient's heart. In some embodiments, an apparatus includes a prosthetic heart valve that includes an inner frame and an outer frame coupled to the inner frame at multiple coupling joints. The prosthetic valve is movable between a first configuration and a second configuration. The multiple coupling joints are configured to allow the outer frame to be moved between a first position relative to the inner frame and a second position relative to inner frame in which the outer frame is inverted relative to the inner frame. The prosthetic valve is in the first configuration when the outer frame is in the first position, and in the second configuration when the outer frame is in the second position.

In some embodiments, an apparatus includes a delivery sheath that defines a lumen, a valve holder movably disposable within the lumen of the delivery sheath, and a prosthetic heart valve disposed at least partially within the lumen of the delivery sheath in a collapsed configuration. The prosthetic heart valve includes an outer frame coupled to an inner frame and the inner frame is releasably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the delivery sheath with the outer frame in the second configuration. A first actuation wire is releasably coupled to a first portion of an open free end portion of the outer frame and a second actuation wire is releasably coupled to a second portion of the open free end portion of the outer frame. Each of the first actuation wire and the second actuation wire has a first portion extending proximally from the outer frame and a second portion extending proximally from the outer frame. The first portion and the second portion of each of the first actuation wire and the second actuation wire are configured to be pulled proximally to urge the outer frame from the second configuration towards the first configuration relative to the inner frame.

BRIEF DESCRIPTION OF THE FIGURES

FIGS. 1A and 1B are schematic illustrations of a portion of a prosthetic heart valve, according to an embodiment, shown in a first configuration and a second configuration, respectively.

FIGS. 1C and 1D are schematic illustrations of the portion of the prosthetic heart valve of FIGS. 1A and 1B, respectively, shown disposed within a delivery sheath.

FIG. 41A is a side view of a portion of an inner frame of a prosthetic heart valve, according to an embodiment.

FIGS. 41B and 41C are a side view and a front view, respectively, of encircled portion A in FIG. 41A.

FIG. 65 is a proximal end view of a tube member of the delivery system of FIG. 63.

FIG. 66A is a side view of a portion of the tube member of FIG. 65.

FIGS. 67A-67D are each a side view of a different embodiment of an actuation wire.

DETAILED DESCRIPTION

Figure 2B:
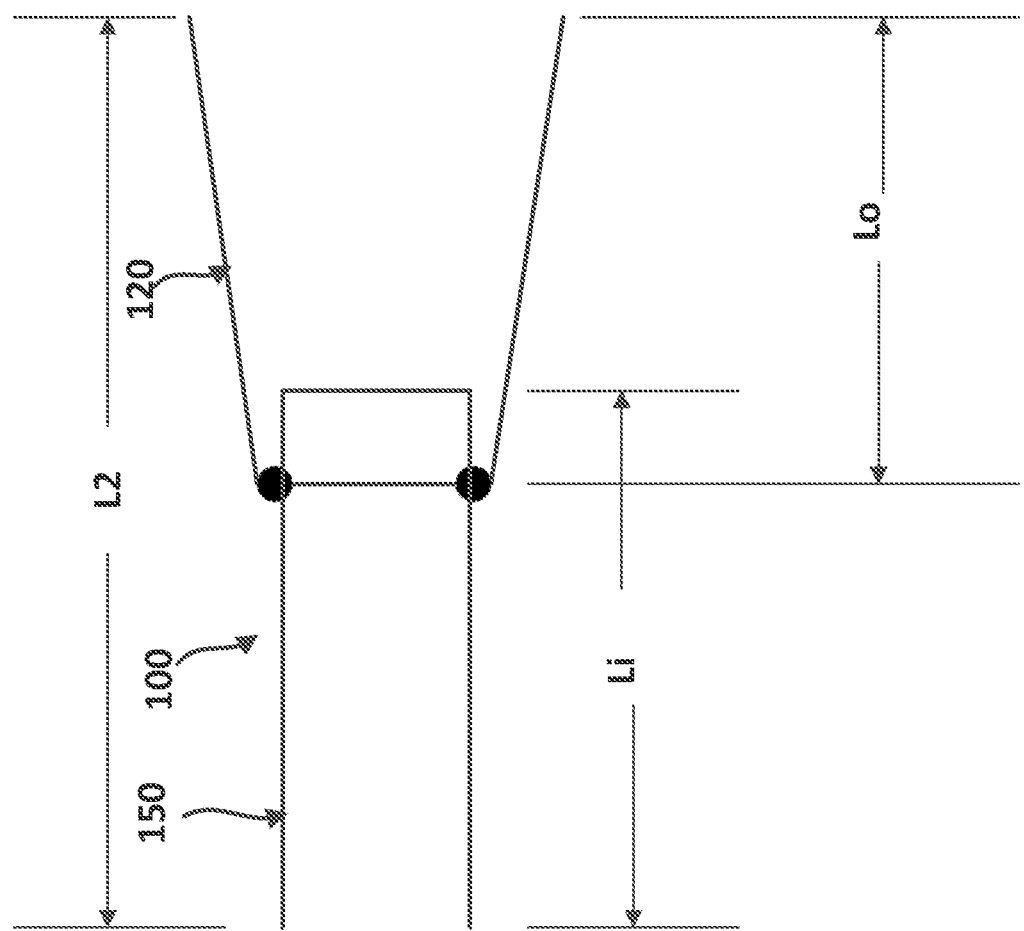
FIGS. 2A and 2B are schematic illustrations of the portion of a prosthetic heart valve of FIGS. 1A and 1B, shown in the first configuration and the second configuration, respectively.

Apparatus and methods are described herein for prosthetic heart valves, such as prosthetic mitral valves, that can be configured to be moved to an inverted configuration for delivery of the prosthetic valve to within a heart of a patient. As described herein, in some embodiments, a prosthetic valve includes an outer frame that can be inverted relative to an inner frame when the prosthetic valve is in a biased expanded configuration. The prosthetic mitral valve can be formed with, for example, a shape-memory material. After inverting the outer frame, the prosthetic valve can be inserted into a lumen of a delivery sheath such that the prosthetic valve is moved to a collapsed configuration.

The delivery sheath can be used to deliver the prosthetic valve to within a patient's heart using a variety of different delivery approaches for delivering a prosthetic heart valve (e.g., prosthetic mitral valve) where the inverted prosthetic valve would enter the heart through the atrium of the heart. For example, the prosthetic valves described herein can be delivered using a transfemoral delivery approach as described in International Application No. PCT/US15/14572 (the '572 PCT application) incorporated by reference above or via a transatrial approach, such as described in U.S. Provisional Patent Application Ser. No. 62/220,704, entitled "Apparatus and Methods for Transatrial Delivery of Prosthetic Mitral Valve," filed Sep. 18, 2015 ("the '704 provisional application"), which is incorporated herein by reference in its entirety. In another example, an inverted valve as described herein could be delivered via a transjugular approach, via the right atrium and through the atrial septum and into the left atrium. The prosthetic valves described herein can also be delivered apically if desired. After the delivery sheath has been disposed within the left atrium of the heart, the prosthetic mitral valve is moved distally out of the delivery sheath such that the inverted outer frame reverts and the prosthetic valve assumes its biased expanded configuration. The prosthetic mitral valve can then be positioned within a mitral annulus of the heart.

In some embodiments, an apparatus includes a prosthetic valve that includes an inner frame and an outer frame coupled to the inner frame at multiple coupling joints. The multiple coupling joints are configured to allow the outer frame to be moved relative to inner frame such that the prosthetic valve can be moved between a first configuration and a second configuration. The outer frame and the inner frame collectively define a first length of the prosthetic valve when the prosthetic valve is in the first configuration and a second length of the prosthetic valve when the prosthetic valve is in the second configuration and the second length is greater than the first length. The inner frame has a length that is the same when the prosthetic valve is in both the first configuration and the second configuration.

In some embodiments, an apparatus includes a prosthetic heart valve that includes an inner frame and an outer frame coupled to the inner frame at multiple coupling joints. The prosthetic valve is movable between a first configuration and a second configuration. The multiple coupling joints are configured to allow the outer frame to be moved between a first position relative to the inner frame and a second position relative to inner frame in which the outer frame is inverted relative to the inner frame. The prosthetic valve is in the first configuration when the outer frame is in the first position, and in the second configuration when the outer frame is in the second position.

In some embodiments, an apparatus includes a prosthetic heart valve that includes an inner frame, and an outer frame coupled to the inner frame at multiple coupling joints. The multiple coupling joints are configured to allow the outer frame to be moved relative to inner frame such that the prosthetic valve can be moved between a first configuration and a second configuration. The outer frame has an outer frame coupling portion coupled to the inner frame at multiple coupling joints and an outer frame free end portion. The inner frame has an inner frame coupling portion coupled to the outer frame at the multiple coupling joints. A first end portion and an inner frame free end portion are on an opposite end of the inner frame from the first end portion. The multiple coupling joints are disposed between the outer frame free end portion and the first end portion of the inner frame when the prosthetic valve is in the first configuration. The multiple coupling joints are disposed between the inner frame free end portion and the outer frame free end portion when the prosthetic valve is in the second configuration.

In some embodiments, an apparatus includes a prosthetic heart valve that includes an inner frame coupled to an outer frame at multiple coupling joints. The multiple coupling joints are configured to allow the outer frame to be moved relative to inner frame such that the prosthetic valve can be moved between a first configuration and a second configuration. The outer frame has an outer frame coupling portion coupled to the inner frame at the multiple coupling joints and an outer frame free end portion. The inner frame has an inner frame coupling portion coupled to the outer frame at the multiple coupling joints and an inner frame free end portion. The outer frame free end portion and the inner frame free end portion each open in the same direction when the prosthetic valve is in the first configuration. The outer frame free end portion and the inner frame free end portion open in opposite directions when the prosthetic valve is in the second configuration.

In some embodiments, an apparatus includes a delivery sheath that defines a lumen, a valve holder movably disposable within the lumen of the delivery sheath and a prosthetic heart valve disposed at least partially within the lumen of the delivery sheath in a collapsed configuration. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the delivery sheath with the outer frame in the second configuration. A first actuation wire is releasably coupled to a first portion of an open free end portion of the outer frame and a second actuation wire is releasably coupled to a second portion of the open free end portion of the outer frame. Each of the first actuation wire and the second actuation wire have a first portion extending proximally from the outer frame and a second portion extending proximally from the outer frame. The first portion and the second portion of each of the first actuation wire and the second actuation wire are configured to be pulled proximally to urge the outer frame from the second configuration towards the first configuration relative to the inner frame.

In some embodiments, an apparatus includes an outer sheath that defines a lumen, an inner sheath movably disposed within the lumen of the outer sheath and defining a lumen, a tube member movably disposed within the lumen of the outer sheath and defining a lumen, a valve holder movably disposed within the lumen of the inner sheath and within a lumen defined by the tube member and a prosthetic heart valve disposed at least partially within the lumen of the outer sheath and at least partially within the lumen of the inner sheath. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the outer sheath and the lumen of the inner sheath with the outer frame in the second configuration. A first actuation wire is releasably coupled to a first portion of an open free end portion of the outer frame and releasably coupled to the tube member at a first location on the tube member. A second actuation wire is releasably coupled to a second portion of the open free end portion of the outer frame and releasably coupled to the tube member at a second location on the tube member.

In some embodiments, a method includes inserting a distal end portion of a delivery sheath into a left atrium of a heart. The delivery sheath having a prosthetic mitral valve disposed within a lumen of the delivery sheath and the prosthetic mitral valve has an outer frame coupled to an inner frame such that the outer frame can be moved between a first position relative to the inner frame and a second position relative to the inner frame in which the outer frame is inverted relative to the inner frame. The prosthetic valve is disposed within the lumen of the delivery sheath with the outer frame in the second position relative to the inner frame. The prosthetic mitral valve is moved distally out of the delivery sheath causing the outer frame of the prosthetic mitral valve to revert back to the first position relative to the inner frame such that the prosthetic mitral valve at least partially assumes a biased expanded configuration. The prosthetic mitral valve is positioned within a mitral annulus of the heart.

Figure 2A:
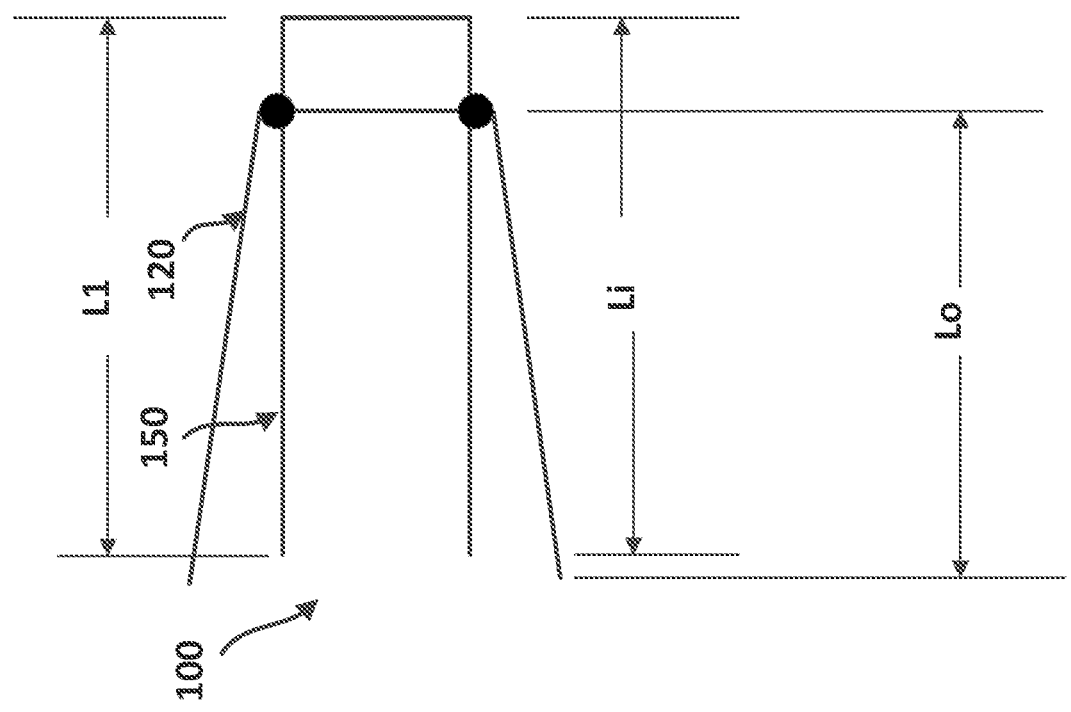

FIGS. 1A and 1B are schematic illustrations of a portion of a prosthetic heart valve 100, according to an embodiment, shown in a first configuration and a second configuration respectively, and FIGS. 1C and 1D illustrate the portions of the prosthetic heart valve 100 of FIGS. 1A and 1B, respectively, shown disposed within a lumen of a delivery sheath 126. FIGS. 2A and 2B illustrate a portion of the prosthetic heart valve 100 of FIGS. 1A and 1B, respectively, and show length dimensions for the prosthetic heart valve in each of the first configuration and the second configuration. The prosthetic heart valve 100 (also referred to herein as "prosthetic valve" or "valve") can be, for example, a prosthetic mitral valve. The valve 100 includes an outer frame 120 and an inner frame 150. The outer frame 120 and the inner frame 150 are each formed as a tubular structure as described in more detail below with reference to FIGS. 3-15. The outer frame 120 and the inner frame 150 can be coupled together at multiple coupling joints 146 disposed about a perimeter of the inner frame 150 and a perimeter of the outer frame 120 as described in more detail below. The valve 100 can also include other features, such as those described with respect to FIGS. 3-15 below. For illustration purposes, only the inner frame 150 and the outer frame 120 are discussed with respect to FIGS. 1A-2B. The various characteristics and features of valve 100 described with respect to FIGS. 1A-2B can apply to any of the prosthetic valves described here.

The outer frame 120 is configured to have a biased expanded or undeformed shape and can be manipulated and/or deformed (e.g., compressed or constrained) and, when released, return to its original (expanded or undeformed) shape. For example, the outer frame 120 can be formed of materials, such as metals or plastics, which have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 150 can be formed from a laser-cut tube of Nitinol®. The inner frame 150 can also have a biased expanded or undeformed shape and can be manipulated and/or deformed (e.g., compressed and/or constrained) and, when released, return to its original (expanded or undeformed) shape. Further details regarding the inner frame 150 and the outer frame 120 are described below with respect to valve 200 and FIGS. 3-15.

The valve 100 can be delivered and deployed within a left atrium of a heart using a variety of different delivery approaches including, for example, a transfemoral delivery approach, as described in the '572 PCT application, or a transatrial approach, as described in the '704 provisional application. As described above, in some situations, such as when delivering a prosthetic valve to the heart via a transfemoral or transatrial approach, because of the smaller size of the lumen of the delivery sheath, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 100 and the embodiments of a prosthetic valve described herein can be constructed and formed to achieve these desired functions and characteristics.

More specifically, the valve 100 can have a biased expanded configuration (as shown in FIGS. 1A and 2A), an inverted configuration (as shown in FIGS. 1B and 2B), and a compressed or collapsed configuration (as shown in FIGS. 1C and 1D). The expanded configuration allows the valve 100 to function when implanted within the heart. The valve 100 can be moved to the inverted configuration and the compressed or collapsed configuration for delivery of the valve 100 to the heart of a patient.

To enable the valve 100 to be moved to the inverted configuration, the outer frame 120 can be coupled to the inner frame 150 in such a manner to allow the outer frame 120 to move relative to the inner frame 150. More specifically, the coupling joints 146 can couple the outer frame 120 to the inner frame 150 in such a manner to allow the outer frame 120 to be moved relative to the inner frame 150. For example, in some embodiments, the coupling joints 146 can be configured to allow the outer frame 120 to rotate about the coupling joint 146 relative to the inner frame 150. In some embodiments, coupling joints can provide a pivotal coupling between the outer frame 120 and the inner frame 150. In some embodiments, the coupling joints can provide a flexible attachment between the outer frame 120 and the inner frame 150. The coupling joints 146 can be a variety of different types and configurations as described herein with reference to the various embodiments of a prosthetic valve. For example, the coupling joints 146 can include a living hinge, a flexible member, sutures, a suture wrapped through an opening, a pin or tab inserted through an opening or any combinations thereof.

To move the valve 100 from the expanded configuration (FIG. 1A) to the inverted configuration (FIG. 1B), the outer frame 120 is moved to a prolapsed or inverted configuration relative to the inner frame 150, as shown in FIGS. 1B, 1D and 2B, by moving (e.g., rotating, pivoting, flexing) the outer frame 120 about the coupling joints 146. The elastic or superelastic structure of outer frame 120 of valve 100 also allows the outer frame 120 to be moved to, and disposed in, the prolapsed or inverted configuration relative to the inner frame 150. To move the outer frame 120 to the inverted configuration relative to the inner frame 150, the outer frame 120 is folded or inverted distally (to the right in FIG. 1B) relative to the inner frame 150 via the coupling joints 146. As shown in FIGS. 1A and 2A, the outer frame 120 is in a first position relative to the inner frame 150 prior to being inverted in which an open or free end portion 116 (also referred to the atrium portion 116 of the outer frame 120) is disposed proximally or to the left of the coupling joints 146 and in the same direction as a free end portion 147 (also referred to as a second end portion of the inner frame) of the inner frame 150. When the outer frame 120 is moved to an inverted configuration (i.e., second position relative to the inner frame 150), the free end portion 116 is disposed distally of the coupling joints 146 (or to the right in FIGS. 1B and 2B) and in an opposite direction as the free end portion 147 of the inner frame 150. Said another way, when the valve 100 is in a biased expanded configuration (e.g., FIG. 1A), the coupling joints 146 are disposed between a first end portion 144 (also referred to as a tether coupling portion) of the inner frame 150 and the free end portion 116 of the outer frame 120. When the valve 100 is in the inverted configuration (e.g., FIG. 1B) (i.e., the outer frame 120 has been moved to an inverted configuration or position), the coupling joints 146 are disposed between the free end portion or second end portion 147 of the inner frame 150 and the free end portion 116 of the outer frame 120.

When in the inverted configuration, an overall length of the valve 100 is increased, but a length of the inner frame 150 and a length of the outer frame 120 remains the same (or substantially the same). For example, as shown in FIGS. 2A and 2B an overall length L1 of the valve 100 in the biased expanded configuration (prior to being inverted as shown in FIG. 2A) is less than the overall length L2 of the valve 100 when in the inverted configuration (FIG. 2B). A length Li of the inner frame 150 and a length Lo of the outer frame 120 is substantially the same (or the same) when the valve 100 is in both the biased expanded configuration and the inverted configuration. In addition, in some instances, depending on the specific configuration of the outer frame, an overall outer perimeter or outer diameter of the valve 100 can be smaller when the valve 100 is in the inverted configuration.

With the valve 100 in the inverted configuration, the valve 100 can be placed within a lumen of the delivery sheath 126 for delivery of the valve 100 to the left atrium of the heart, as shown in FIG. 1D. When placed within the lumen of the delivery sheath 126, the valve 100 is moved to the collapsed or compressed configuration in which the outer diameter or outer perimeter of the valve 100 is reduced. Because the valve 100 is in the inverted configuration, the valve 100 is able to be placed within a smaller delivery sheath 126 than would otherwise be possible. For example, for comparison purposes, FIG. 1C illustrates the valve 100 placed within a lumen of a delivery sheath 126' where the valve 100 has not been moved to an inverted configuration prior to being disposed within the delivery sheath 126'. As shown in FIG. 1C, an outer diameter of the valve 100 is reduced, but not to as small of a diameter as for the valve 100 when placed in a delivery sheath 126 when in the inverted configuration. Thus, in FIG. 1C, the valve 100 has an overall outer perimeter or outer diameter D1 and in FIG. 1D, the valve 100 has an overall outer perimeter or outer diameter D2, which is less than D1.

Thus, by disposing the outer frame 120 in the inverted configuration, the valve 100 can be collapsed into a smaller overall diameter, i.e. placed in a smaller diameter delivery sheath 126, than would be possible if the valve 100 were merely collapsed radially. This is because when the valve is in the biased expanded configuration, the inner frame 150 is nested within an interior of the outer frame 120, and thus the outer frame 120 must be collapsed around the inner frame 150. In some embodiments, the inner frame 150 and the outer frame are disposed concentrically. Whereas in the inverted configuration, the inner frame 150 and the outer frame 120 are arranged axially with respect to each other (i.e., the inner frame is not nested within the outer frame 150), such that the outer frame 120 can be collapsed without needing to accommodate all of the structure of the inner frame 150 inside it. In other words, with the inner frame 150 disposed mostly inside or nested within the outer frame 120, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 3:
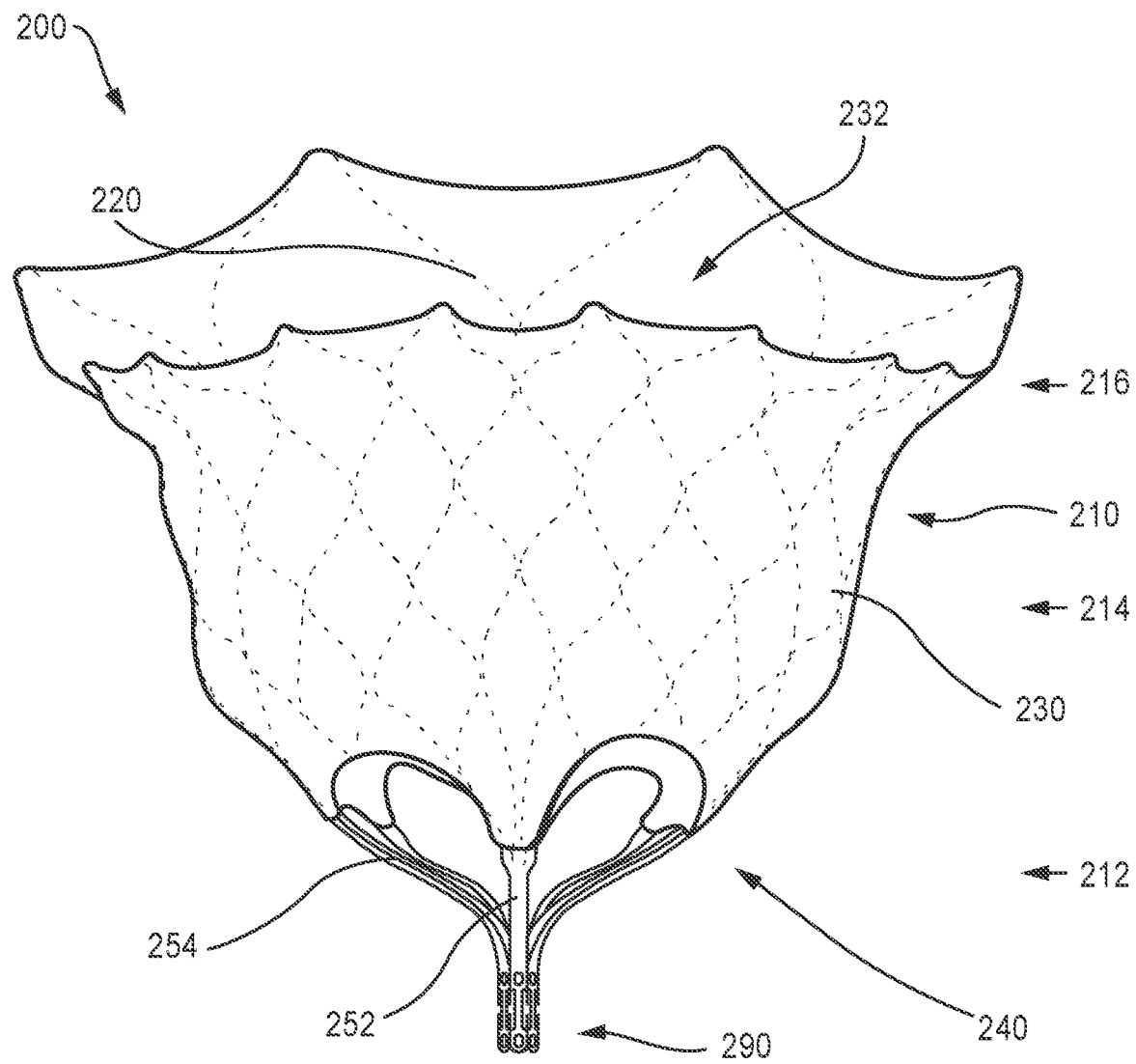
FIGS. 3-5 are front, bottom, and top views of a prosthetic heart valve according to an embodiment.
Figure 4:
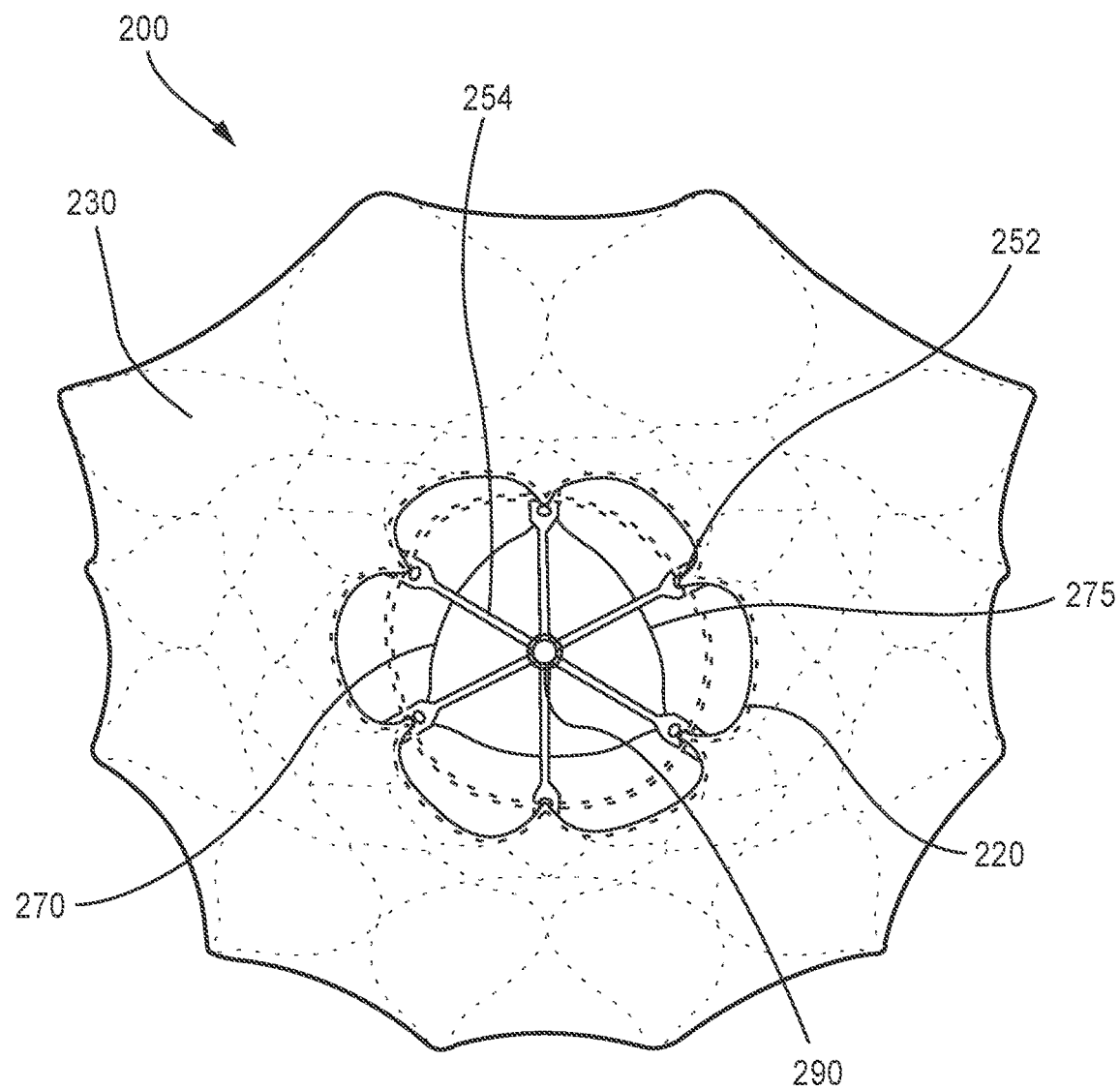
Figure 5:
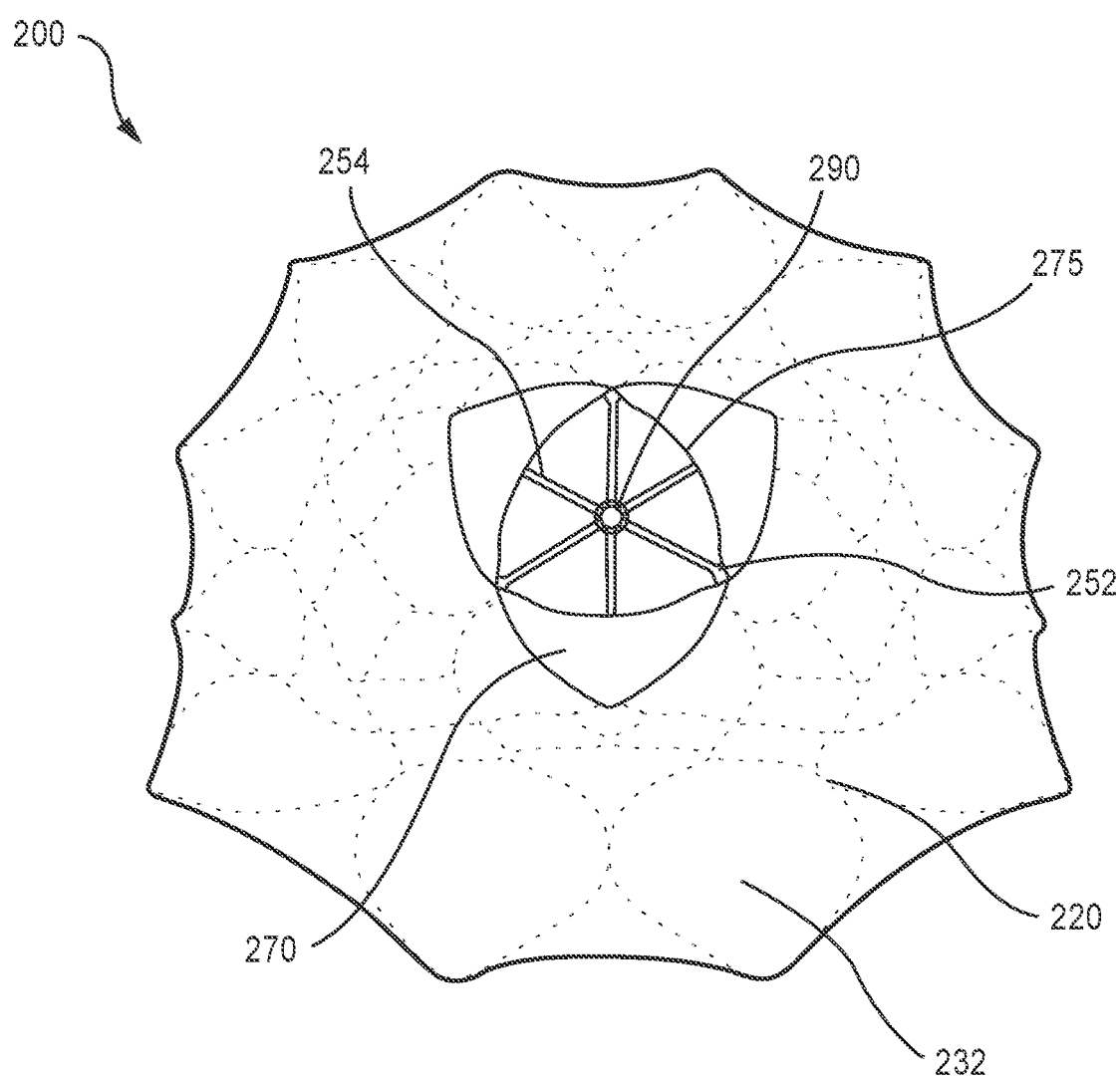

FIGS. 3-14 illustrate another embodiment of a prosthetic heart valve that can be delivered and deployed within a left atrium of a heart using a variety of different delivery approaches including, for example, a transfemoral delivery approach or a transatrial delivery approach. FIGS. 3-5 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering (not shown), and leaflets 270. As shown, the inner valve assembly 240 includes an upper portion having a periphery formed with multiple arches. The inner frame 250 includes six axial posts or frame members that support the outer covering of the inner valve assembly and leaflets 270. Leaflets 270 are attached along three of the posts, shown as commissure posts 252 (best illustrated in FIG. 4), and the outer covering of the inner valve assembly 240 is attached to the other three posts, 254 (best illustrated in FIG. 4), and optionally to commissure posts 252. Each of the outer covering of the inner valve assembly 240 and leaflets 270 are formed of approximately rectangular sheets of material, which are joined together at their upper, or atrium end. The lower, ventricle end of the outer covering may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 6:
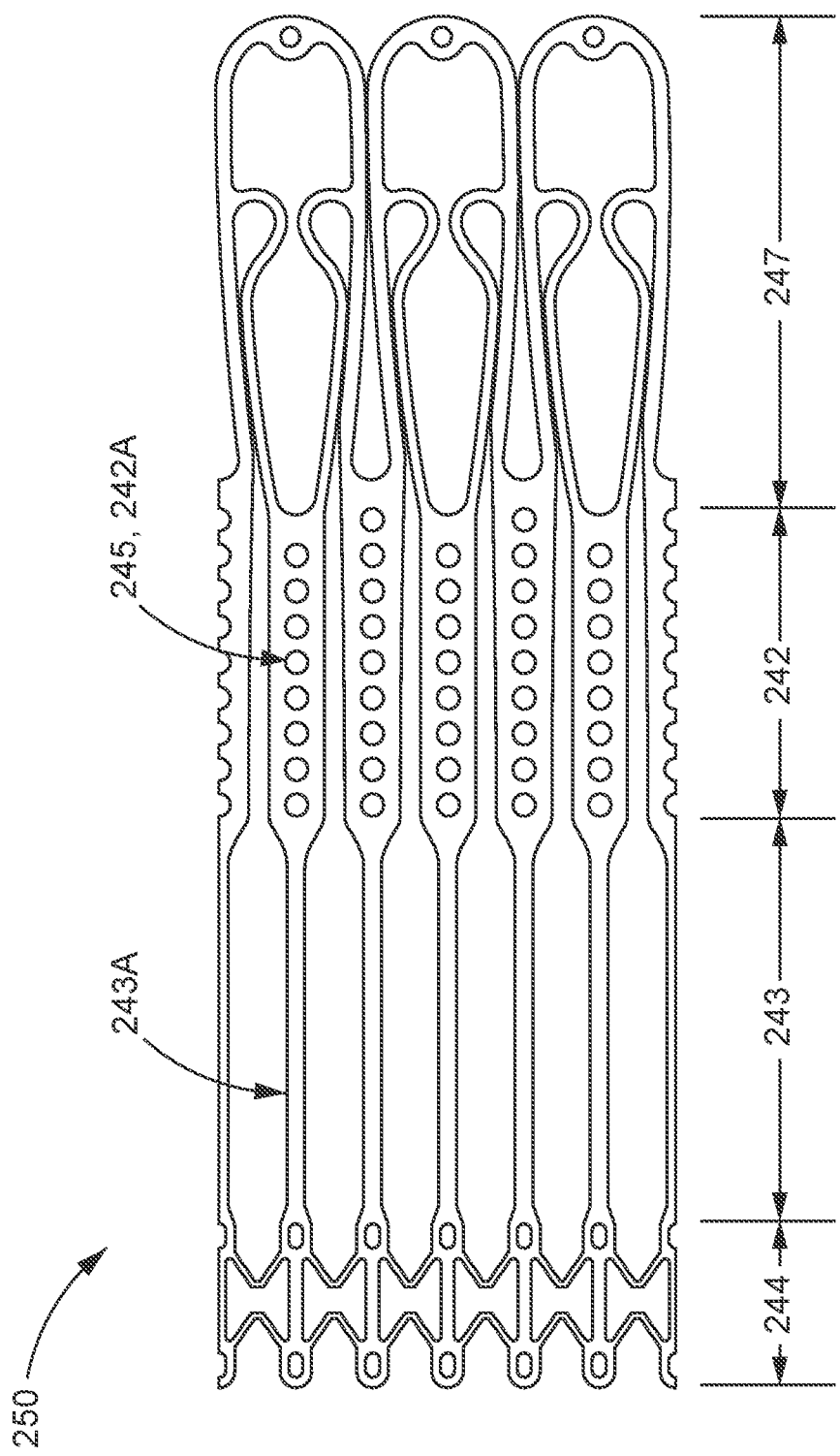
FIG. 6 is an opened and flattened view of the inner frame of the prosthetic heart valve of FIGS. 3-5, in an unexpanded configuration.
Figure 7:
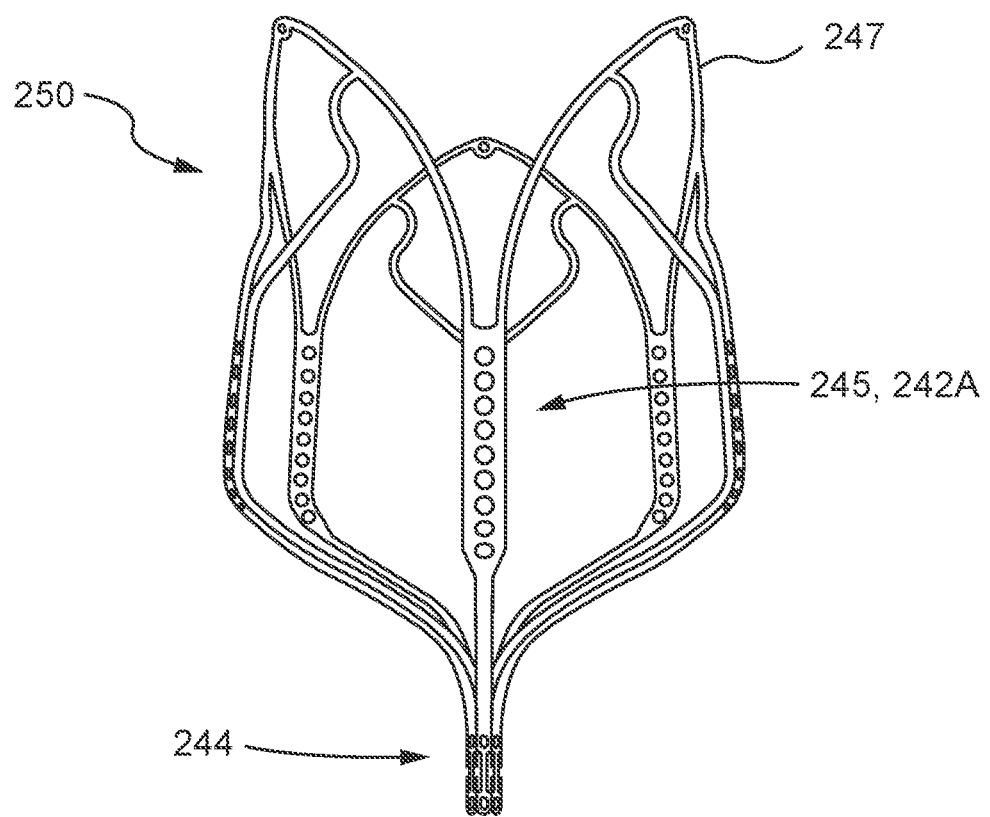
FIGS. 7 and 8 are side and bottom views, respectively, of the inner frame of FIG. 6 in an expanded configuration.
Figure 8:
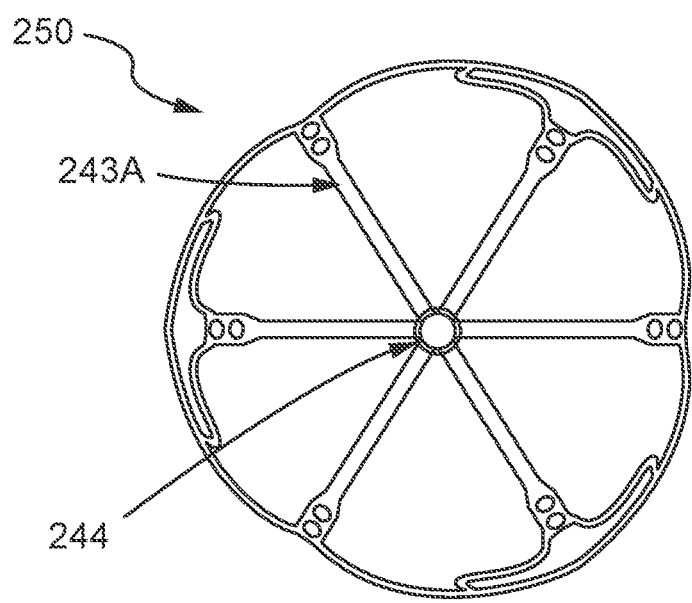

Inner frame 250 is shown in more detail in FIGS. 6-8. Specifically, FIGS. 6-8 show inner frame 250 in an undeformed, initial state (FIG. 6), a side view of the inner frame 250 in an expanded configuration (FIG. 7), and a bottom view of the inner frame 250 in the expanded configuration (FIG. 8), respectively, according to an embodiment.

In this embodiment, inner frame 250 is formed from a laser-cut tube of Nitinol®. Inner frame 250 is illustrated in FIG. 6 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in term firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, i.e. the final, deployed configuration, in side view and bottom view in FIGS. 7 and 8, respectively.

Figure 9:
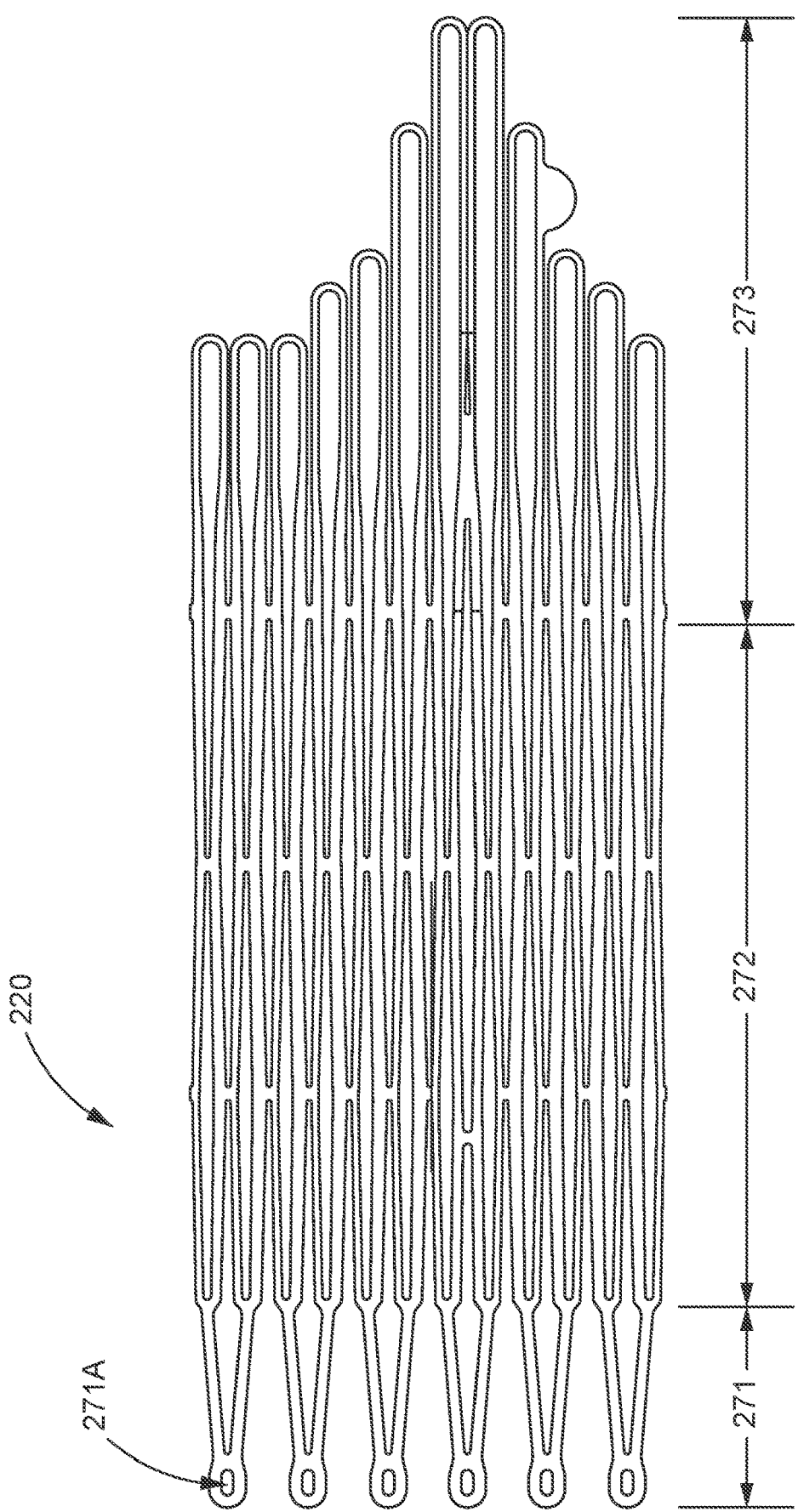
FIG. 9 is an opened and flattened view of the outer frame of the valve of FIGS. 3-5, in an unexpanded configuration.
Figure 10:
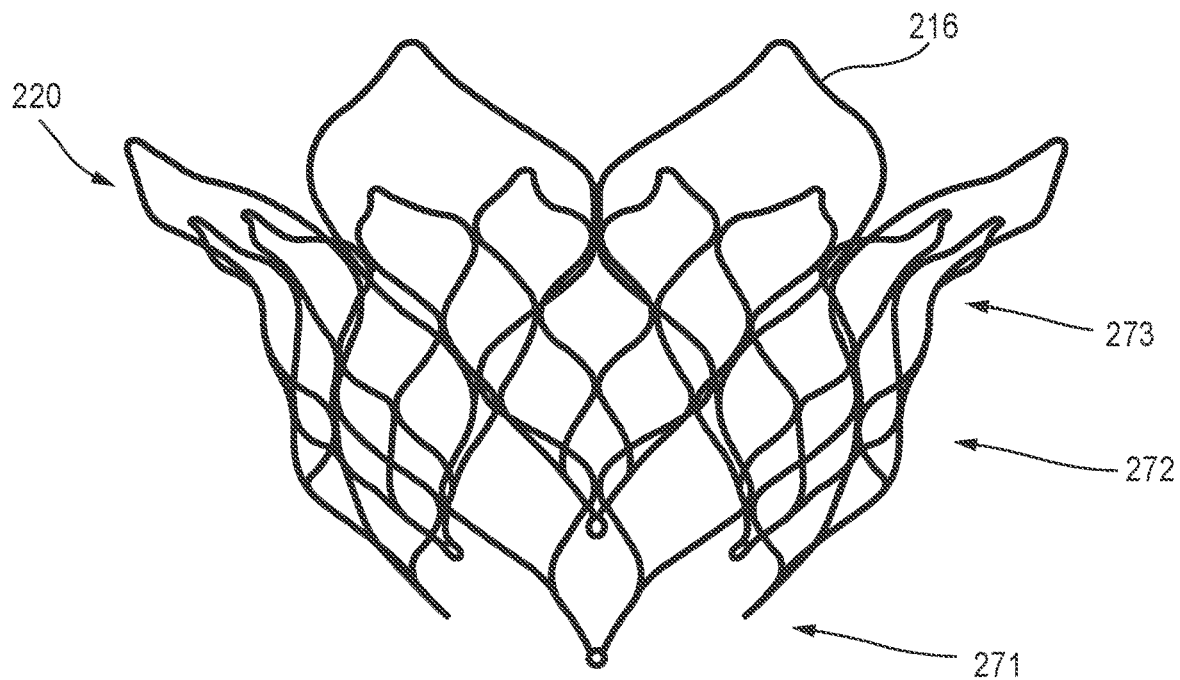
FIGS. 10 and 11 are side and top views, respectively, of the outer frame of FIG. 9 in an expanded configuration.
Figure 11:
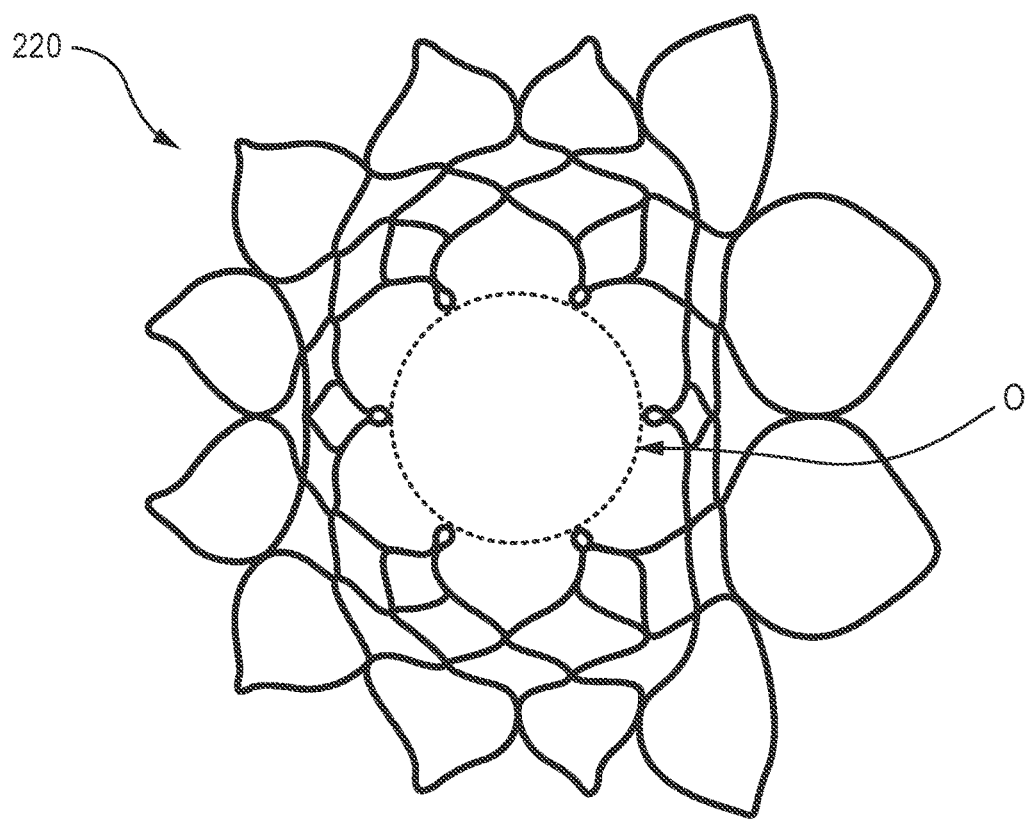

Outer frame 220 of valve 200 is shown in more detail in FIGS. 9-11. In this embodiment, outer frame 220 is also formed from a laser-cut tube of Nitinol®. Outer frame 220 is illustrated in FIG. 9 in an undeformed, initial state, i.e. as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 9. Outer frame coupling portion 271 includes multiple openings or apertures, such as 271A, by which outer frame 220 can be coupled to inner frame 250, as discussed in more detail below.

Outer frame 220 is shown in a fully deformed, i.e. the final, deployed configuration, in side view and top view in FIGS. 10 and 11, respectively. As best seen in FIG. 11, the lower end of outer frame coupling portion 271 forms a roughly circular opening (identified by "O" in FIG. 11). The diameter of this opening preferably corresponds approximately to the diameter of body portion 242 of inner frame 250, to facilitate coupling of the two components of valve 200.

Figure 12:
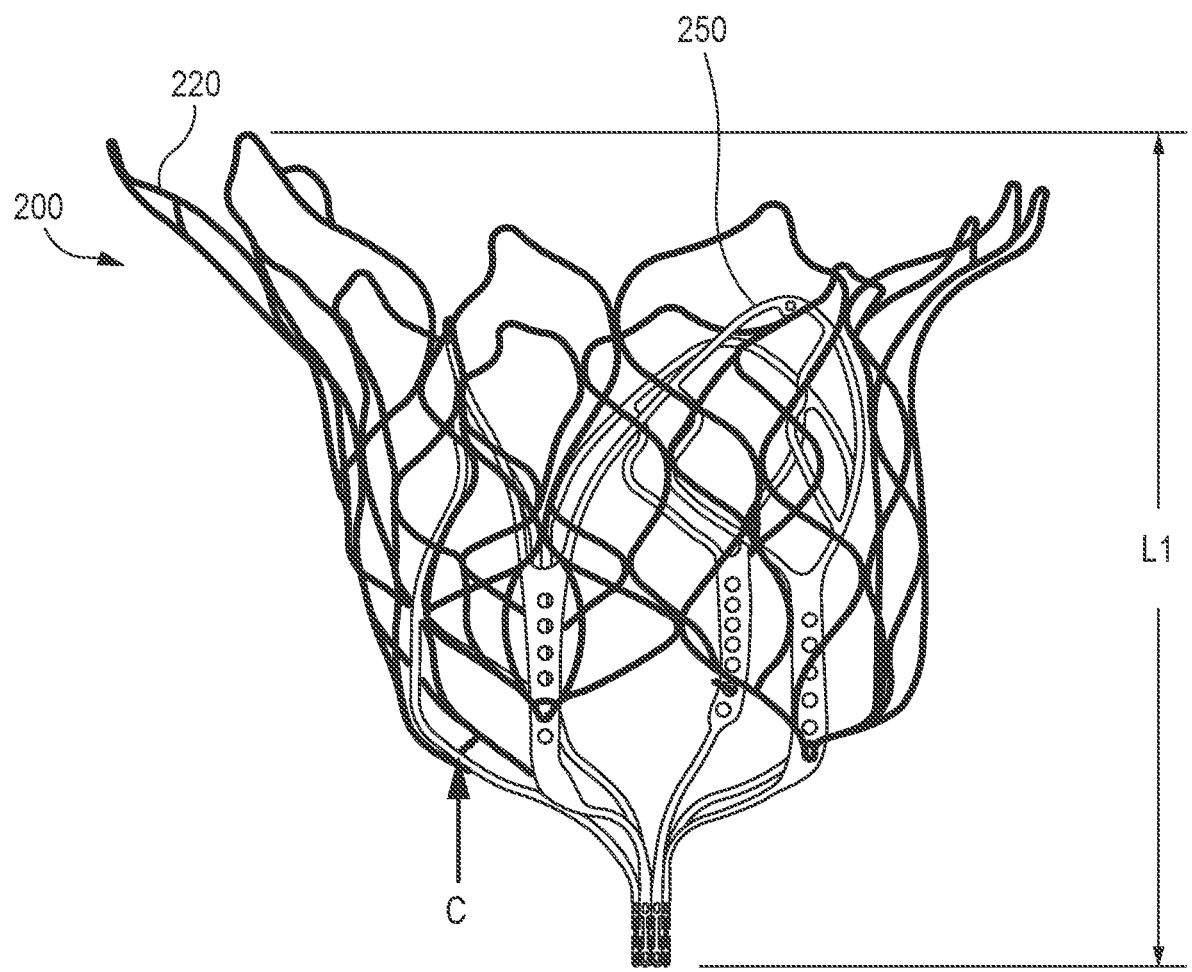
FIGS. 12-14 are side, front, and top views of an assembly of the inner frame of FIGS. 6-8 and the outer frame of FIGS. 9-11.
Figure 13:
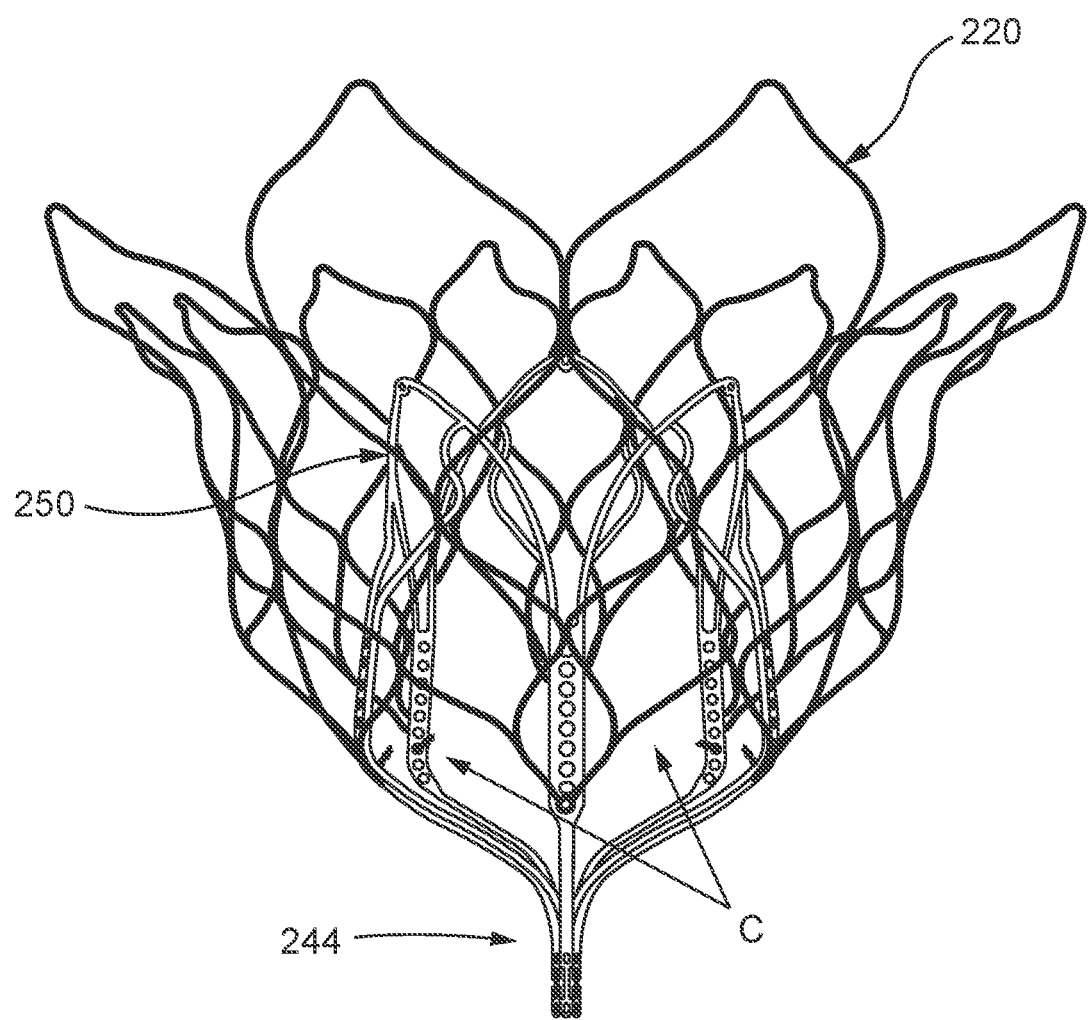
Figure 14:
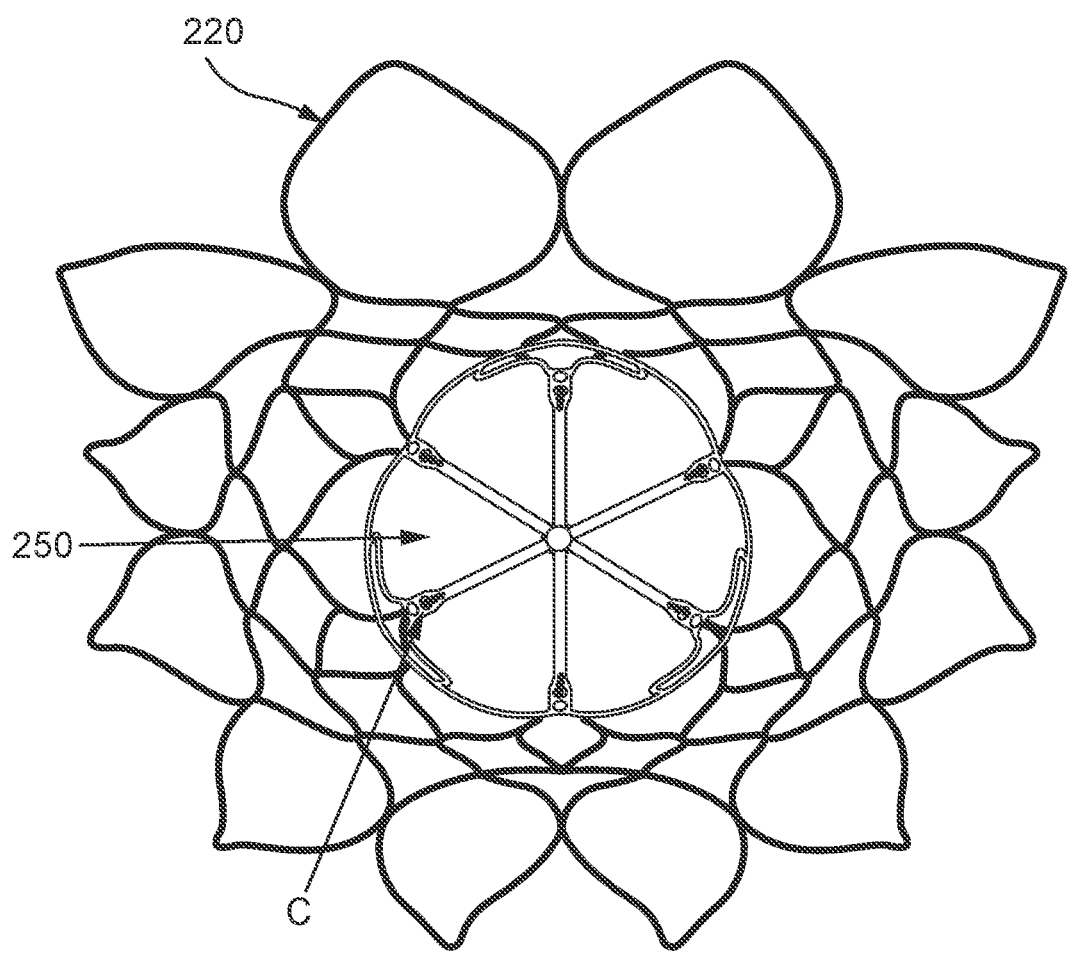

Outer frame 220 and inner frame 250 are shown coupled together in FIGS. 12-14, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering of inner valve assembly 240) for the two frames to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall. The outer frame 220 and the inner frame 250 are connected at six coupling points (representative points are identified as "C"). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

FIGS. 15-21 illustrate a method of reconfiguring a prosthetic heart valve 300 (e.g., prosthetic mitral valve) prior to inserting the prosthetic heart valve 300 into a delivery sheath 326 (see, e.g., FIGS. 17-21) for delivery into the atrium of the heart. The prosthetic heart valve 300 (also referred to herein as "valve") can be constructed the same as or similar to, and function the same as or similar to the valves 100 and 200 described above. Thus, some details regarding the valve 300 are not described below. It should be understood that for features and functions not specifically discussed, those features and functions can be the same as or similar to the valve 200.

Figure 15:
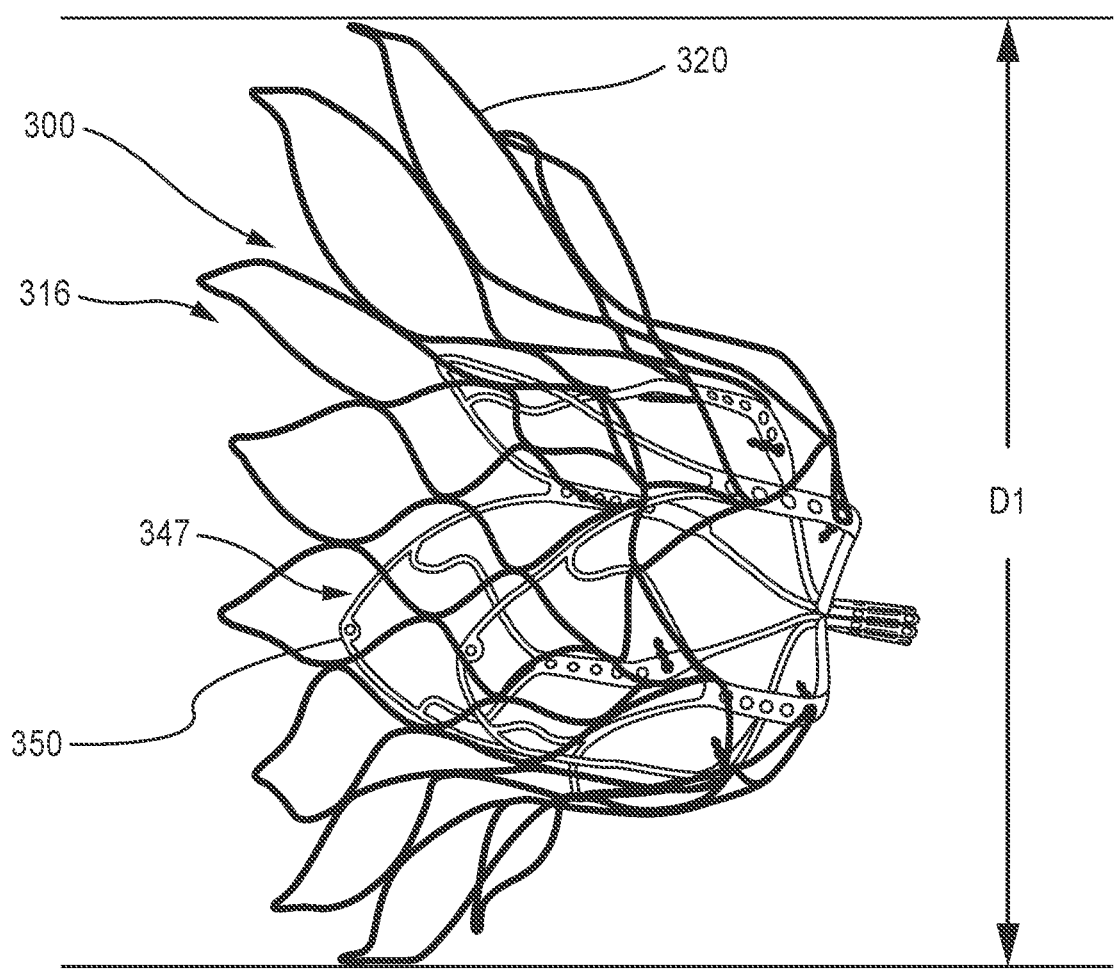
FIG. 15 is a side perspective view of an assembly of an inner frame and an outer frame shown in a biased expanded configuration, according to an embodiment.
Figure 16:
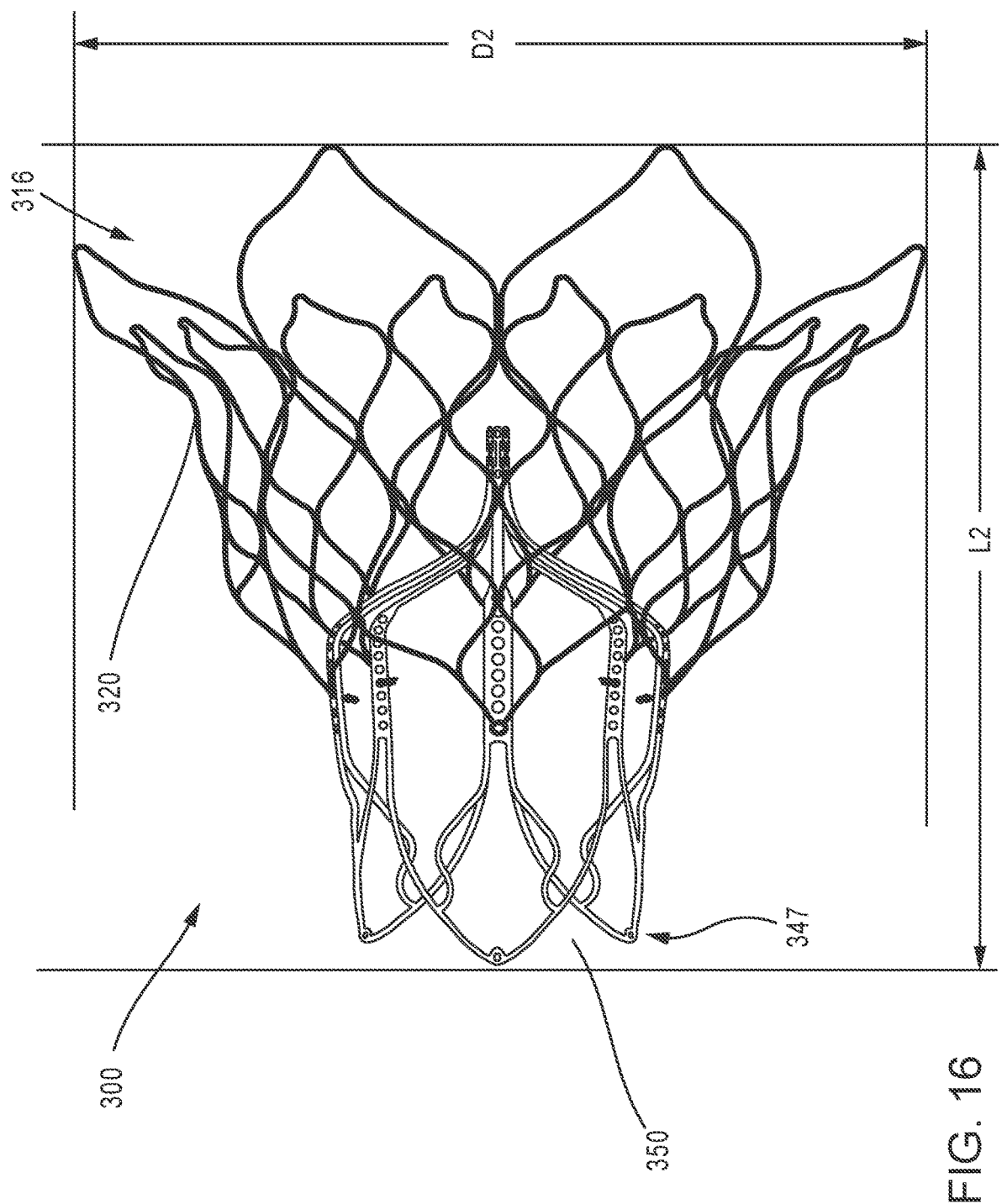
FIG. 16 is a side perspective view of the assembly of FIG. 15 with the outer frame shown inverted.
Figure 17:
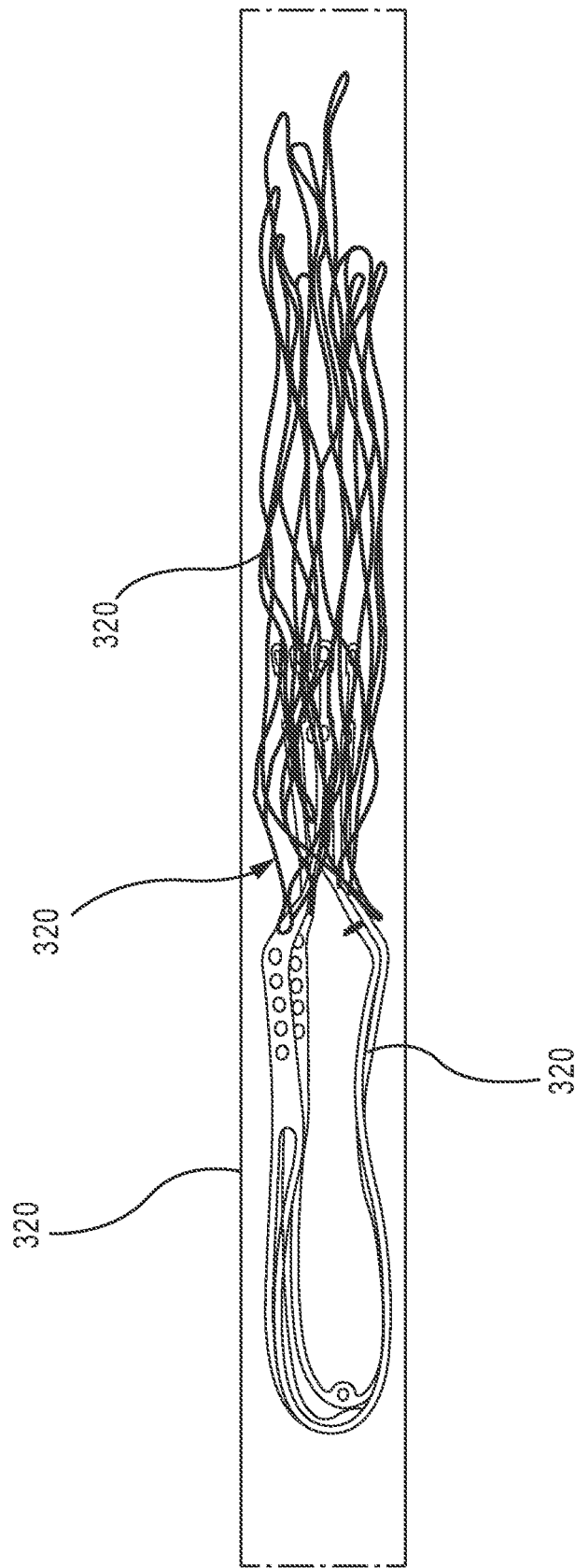
FIG. 17 is side view of the assembly of FIG. 16 shown in a collapsed configuration within a lumen of a delivery sheath.

As shown in FIG. 15, the valve 300 has an outer frame 320 and an inner frame 350. As discussed above for valves 100 and 200, the outer frame 320 and the inner frame 350 of valve 300 can each be formed with a shape-memory material and have a biased expanded configuration. The outer frame 320 and the inner frame 350 can be moved to a collapsed configuration for delivery of the valve 300 to the heart. In this example method of preparing the valve 300 for delivery to the heart, the outer frame 320 of the valve 300 is first disposed in a prolapsed or inverted configuration as shown in FIG. 16. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 16, to dispose the outer frame 320 in the inverted configuration, the outer frame 320 is folded or inverted distally (to the right in FIG. 16) such that an open free end 316 of the outer frame 320 is pointed away from an open free end 347 of the inner frame 350. As described above for valve 100, in this inverted configuration, the overall outer perimeter or outer diameter of the valve 300 is reduced and the overall length is increased. For example, the diameter D1 shown in FIG. 15 is greater than the diameter D2 shown in FIG. 16, and the length L1 (shown in FIG. 12 for valve 200) is less than the length L2 shown in FIG. 16 for valve 300. With the outer frame 320 in the inverted configuration relative to the inner frame 350, the valve 300 can be placed within a lumen of a delivery sheath 326 as shown in FIG. 17 for delivery of the valve 300 to the left atrium of the heart. By disposing the outer frame 320 in the inverted configuration relative to the inner frame 350, the valve 300 can be collapsed into a smaller overall diameter, i.e. when placed in a smaller diameter delivery sheath, than would be possible if the valve 300 in the configuration shown in FIG. 15 were collapsed radially without being inverted. This is because in the configuration shown in FIG. 15, the two frames are concentric or nested, and thus the outer frame 320 must be collapsed around the inner frame 350, whereas in the configuration shown in FIG. 16, the two frames are substantially coaxial but not concentric or nested. Thus, in the configuration shown in FIG. 16 the outer frame 320 can be collapsed without the need to accommodate the inner frame 350 inside of it. In other words, with the inner frame 350 disposed mostly inside or nested within the outer frame 320, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 22:
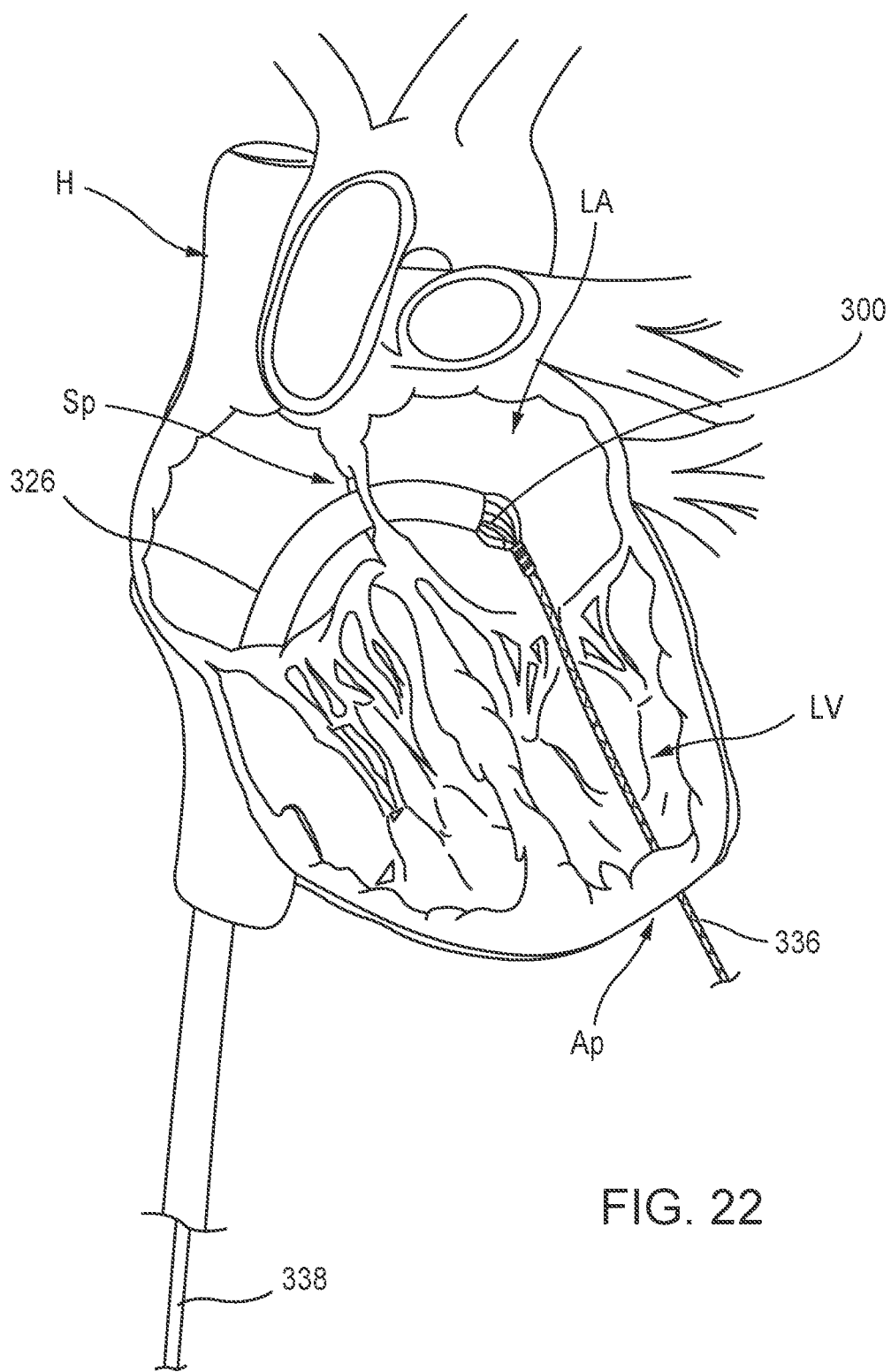
FIGS. 22-24 illustrate steps of a portion of a method to deliver the prosthetic valve of FIGS. 15-21 to an atrium of a heart and within the native mitral annulus.
Figure 23:
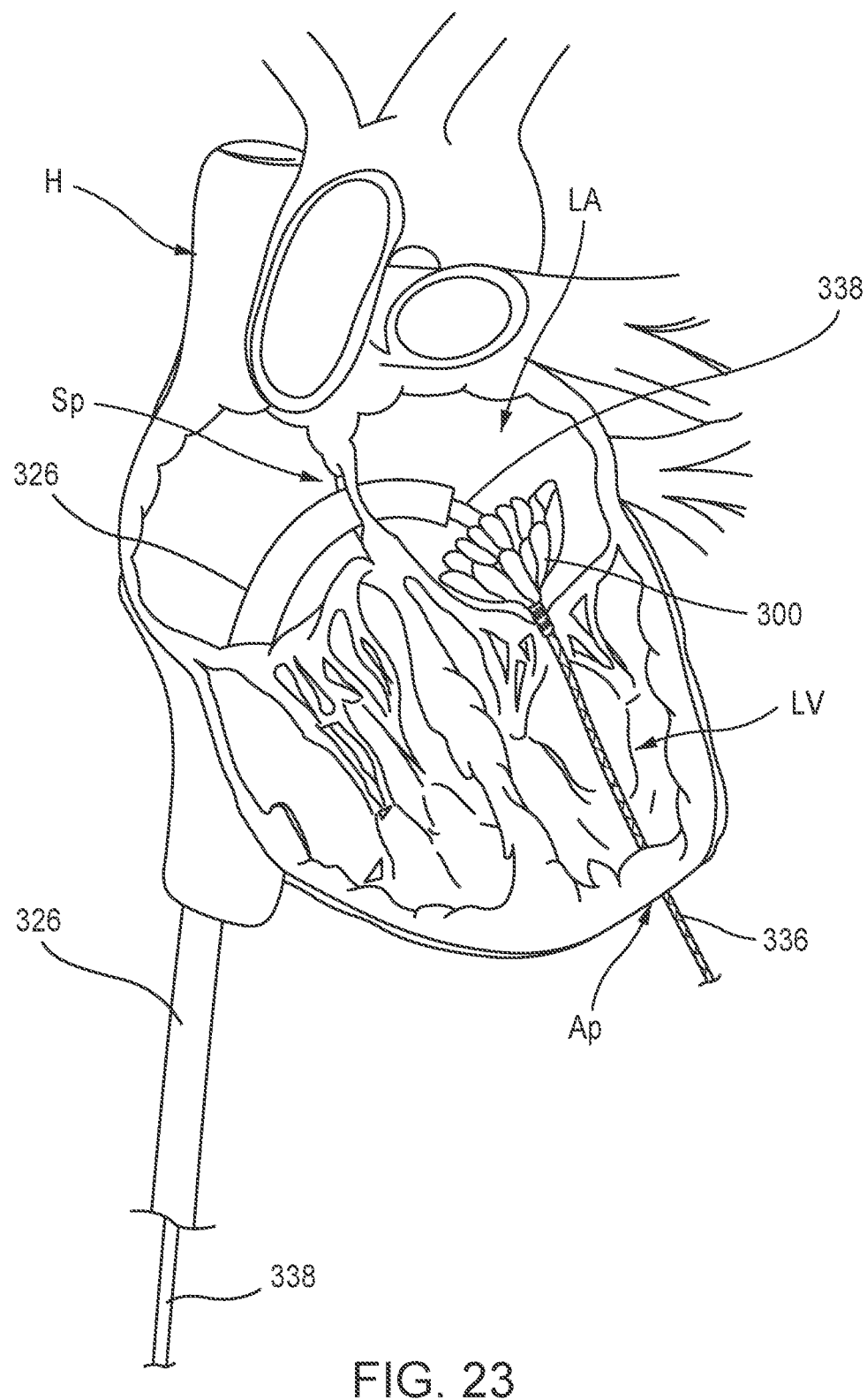
Figure 24:
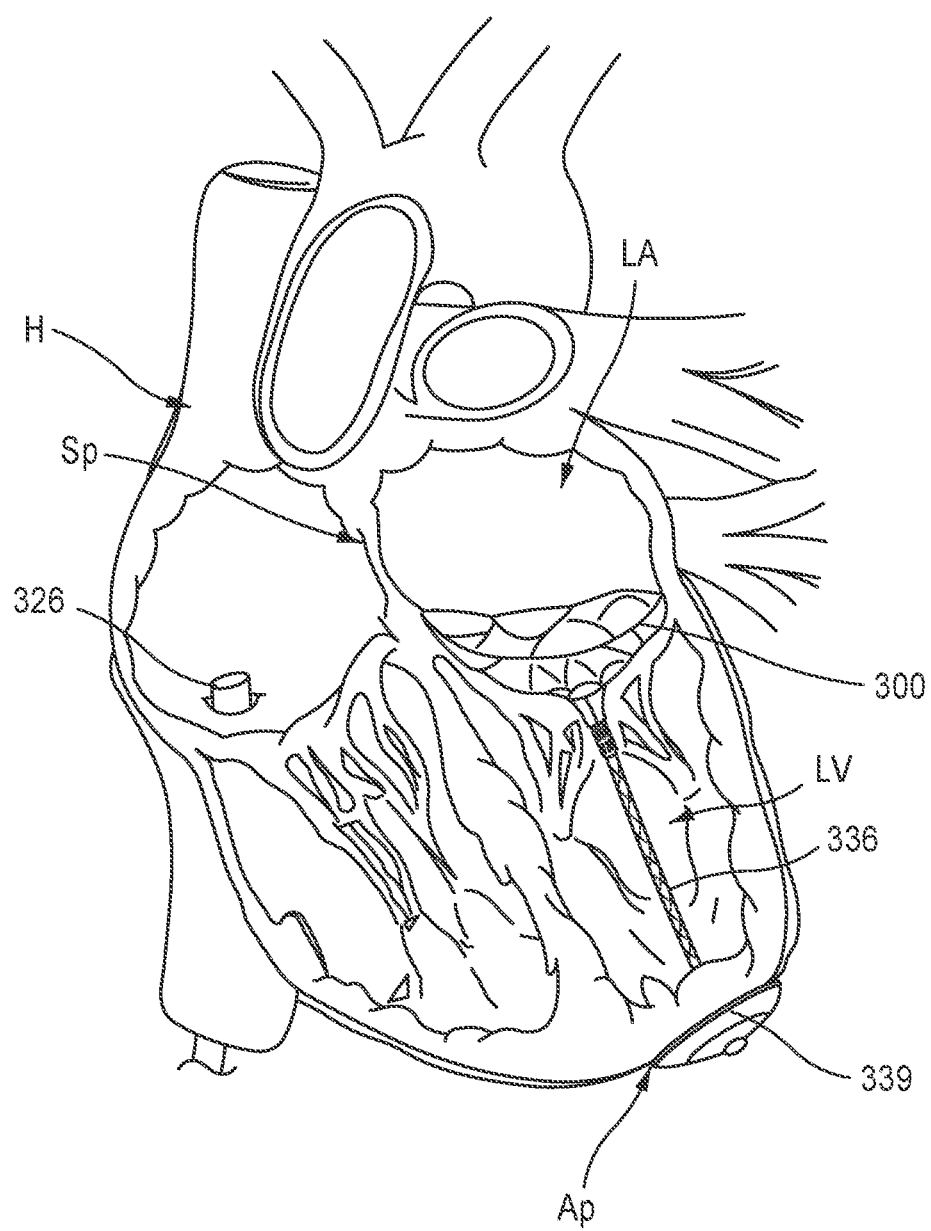
Figure 25:
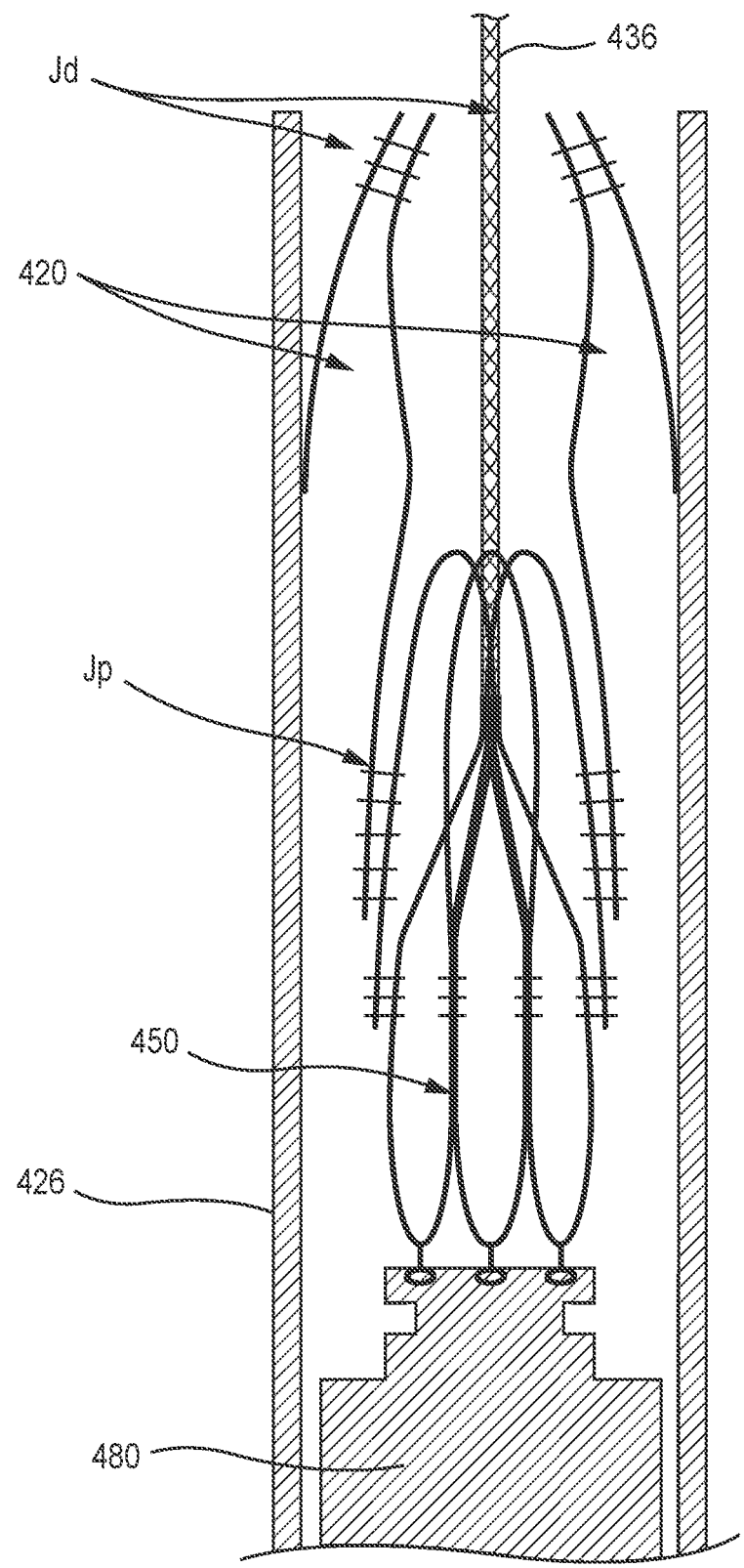
FIGS. 25-28 are cross-sectional side views of a prosthetic valve, according to an embodiment, showing the progression of the prosthetic valve being reconfigured and reoriented, and emerging from a lumen of a portion of a delivery sheath.

FIGS. 22-24 illustrate a portion of a procedure to deliver the valve 300 to the heart. In this embodiment, the valve 300 is shown being delivered via a transfemoral delivery approach as described, for example, in the '572 PCT application incorporated by reference above. The delivery sheath 326, with the valve 300 disposed within a lumen of the delivery sheath 326 and in an inverted configuration as shown in FIG. 17, can be inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside a distal end of the delivery sheath 326. For example, in some embodiments, a pusher device 338 can be used to move or push the valve 300 out the distal end of the delivery sheath 326. As shown in FIGS. 22-24, a tether 336 can be attached to the valve 300, and extend though the mitral annulus, through the left ventricle LV, and out a puncture site at the apex Ap. In some embodiments, the valve 300 can be moved out of the delivery sheath 326 by pulling proximally on the tether 336. In some embodiments, the valve 300 can be deployed by pushing with the pusher device and pulling with the tether.

Figure 18:
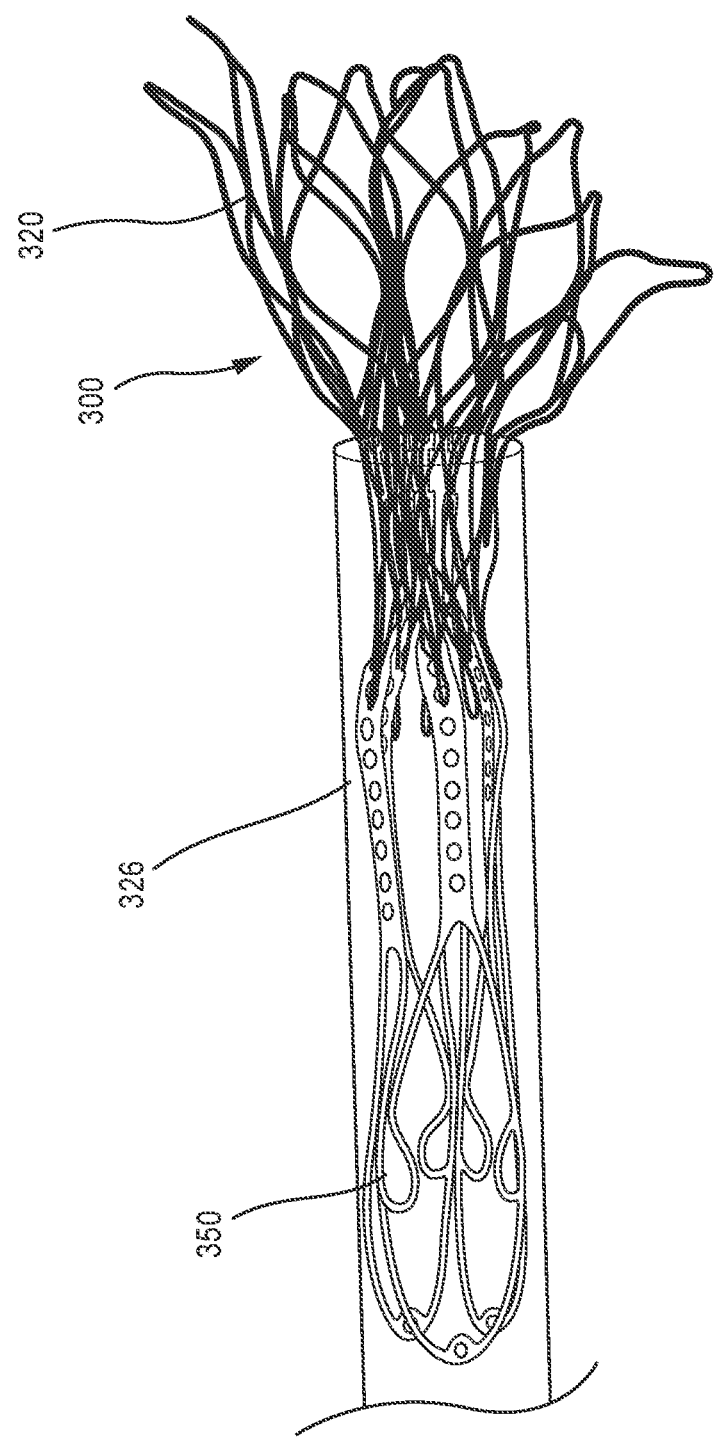
FIG. 18 is a side view of the assembly of FIG. 17 shown in a first partially deployed configuration.
Figure 19:
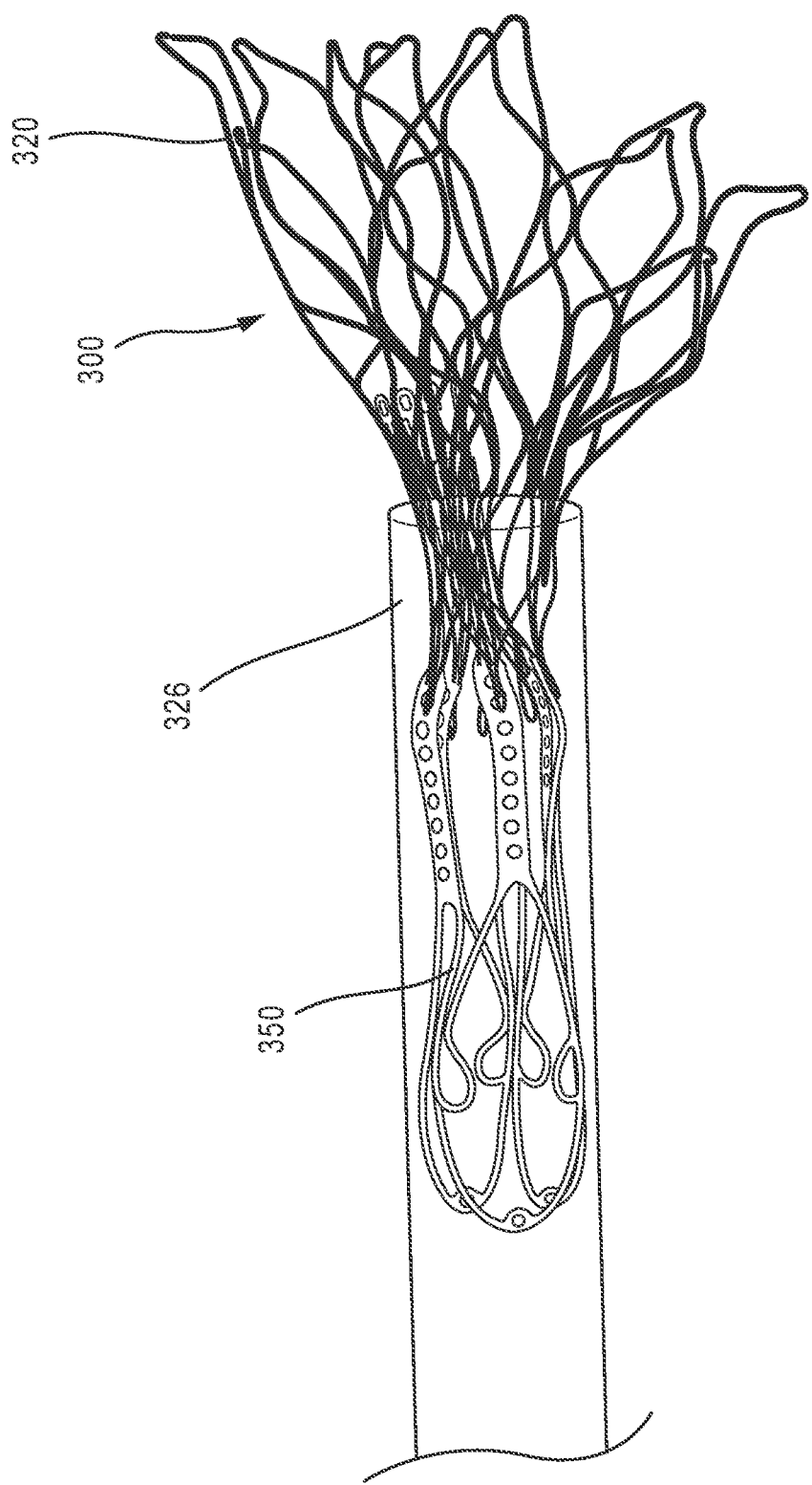
FIG. 19 is a side view of the assembly of FIG. 17 shown in a second partially deployed configuration.
Figure 20:
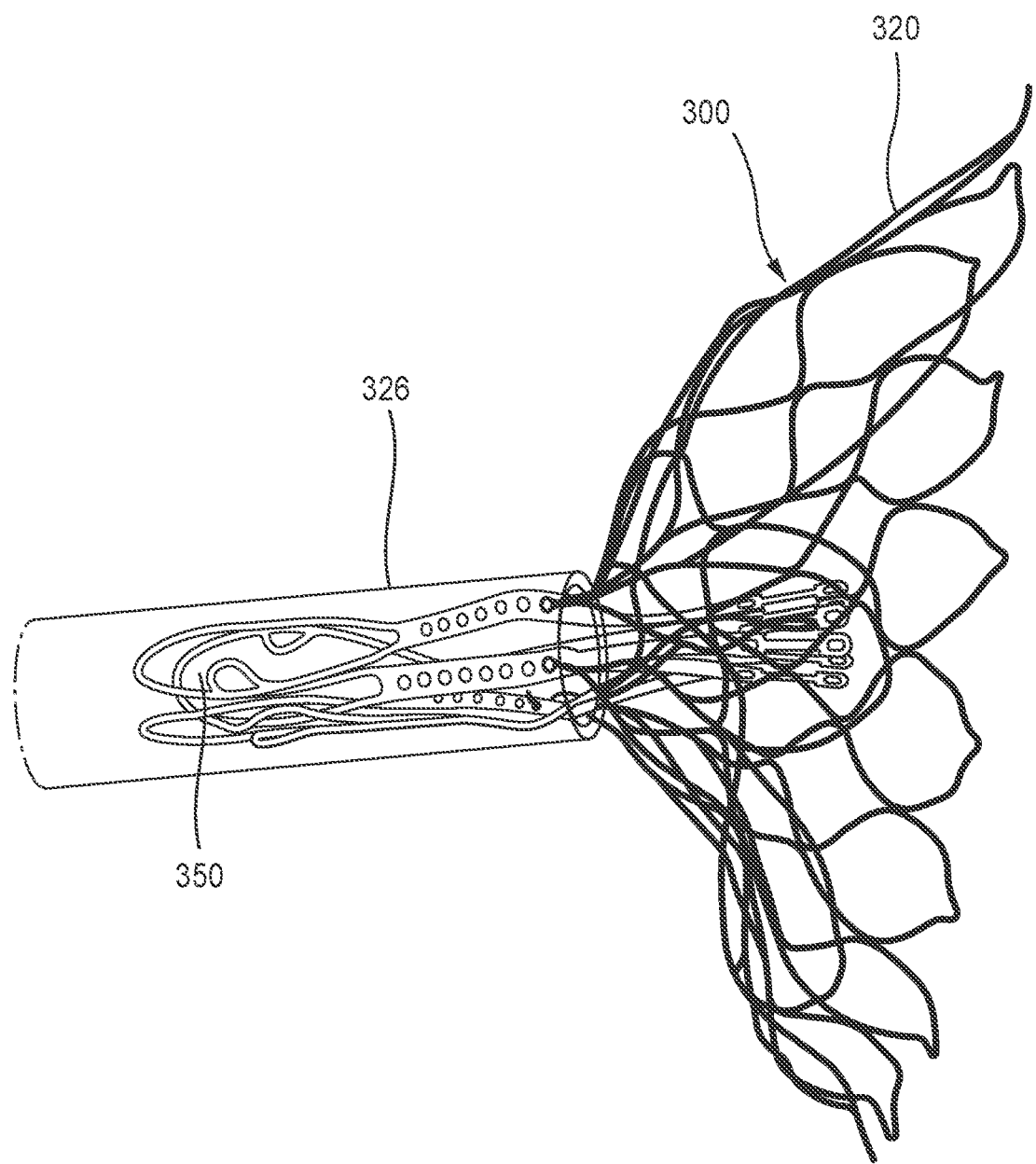
FIG. 20 is a side view of the assembly of FIG. 17 shown in a third partially deployed configuration in which the inverted outer frame is substantially deployed outside of the delivery sheath.
Figure 21:
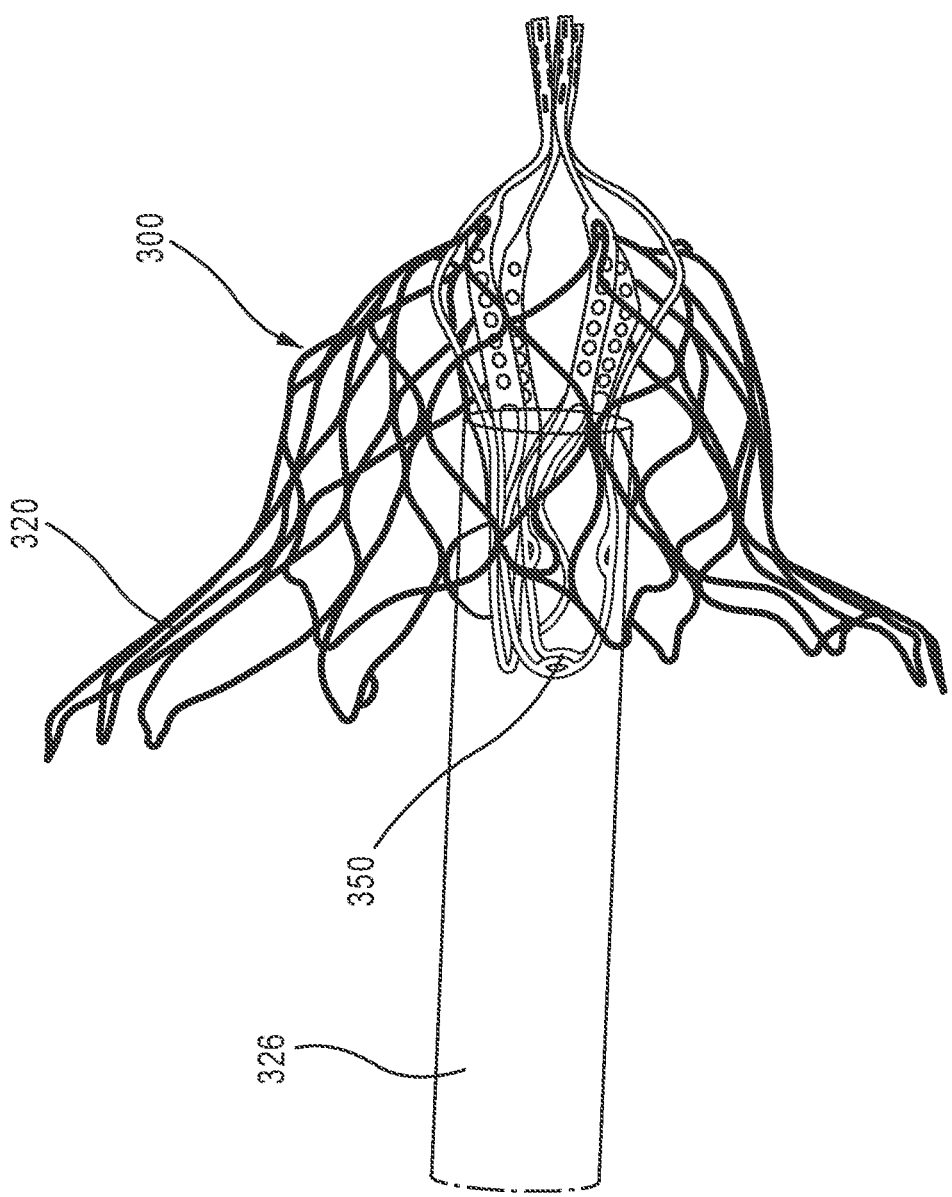
FIG. 21 is a side view of the assembly of FIG. 17 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 18-20 (see also FIG. 22). After the outer frame assembly 310 is fully outside of the lumen of the delivery sheath 326, the outer frame 320 can revert to its expanded or deployed configuration as shown in FIGS. 21, 23 and 24. In some embodiments, the outer frame 320 can revert automatically after fully exiting the lumen of the delivery sheath due to its shape-memory properties. In some embodiments, a component of the delivery sheath or another device can be used to aid in the reversion of the outer frame assembly 310. In some embodiments, the pusher device and/or the tether can be used to aid in the reversion of the outer frame assembly 310. The valve 300 can continue to be deployed until the inner frame 350 is fully deployed with the left atrium and the valve 300 is in the expanded or deployed configuration (as shown, e.g., in FIGS. 15 and 24). The valve 300 and the tether 336 can then be secured to the apex of the heart with an epicardial pad device 339 as shown in FIG. 24 and as described in more detail in the '572 PCT application.

Figure 26:
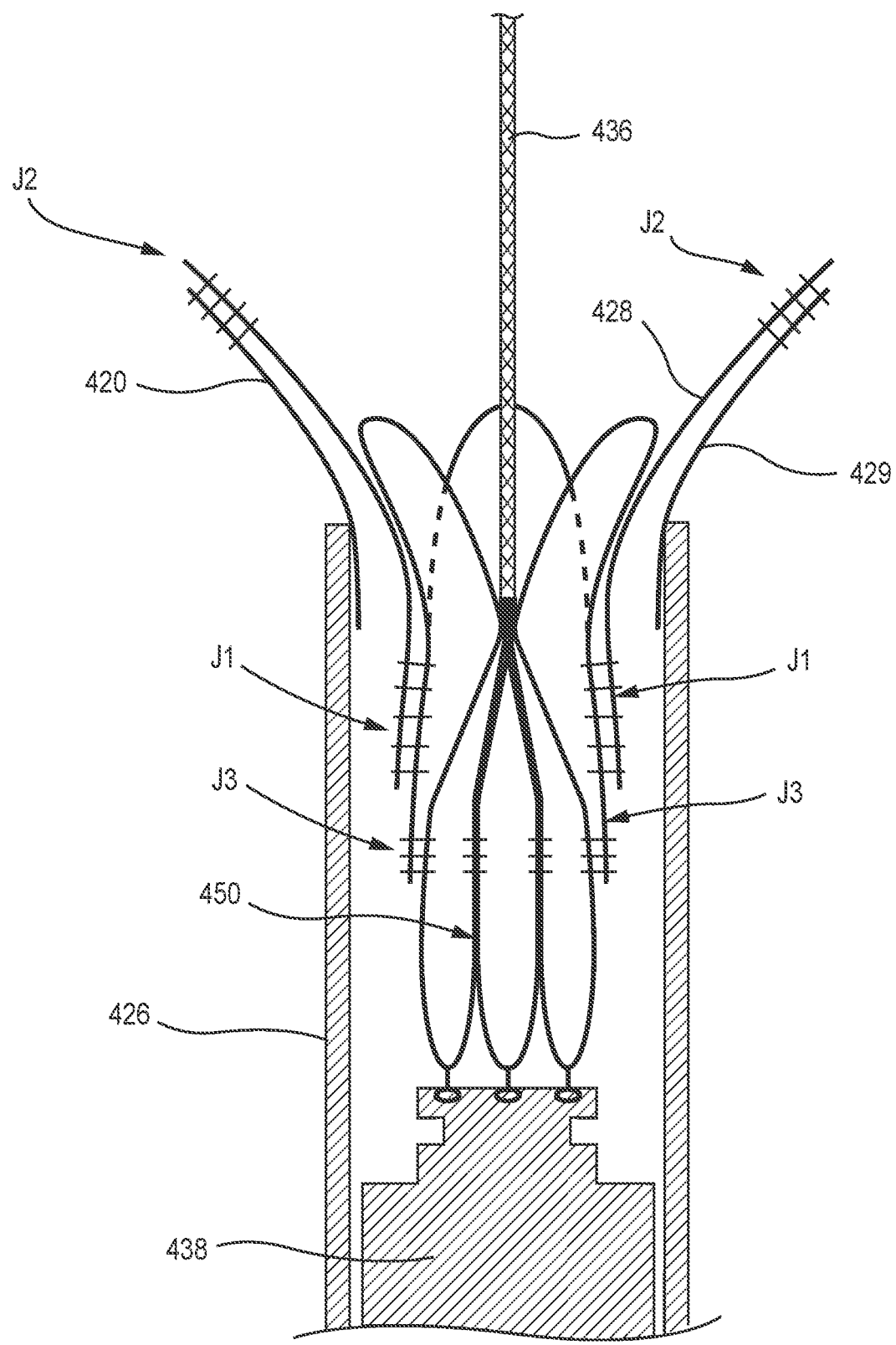
Figure 27:
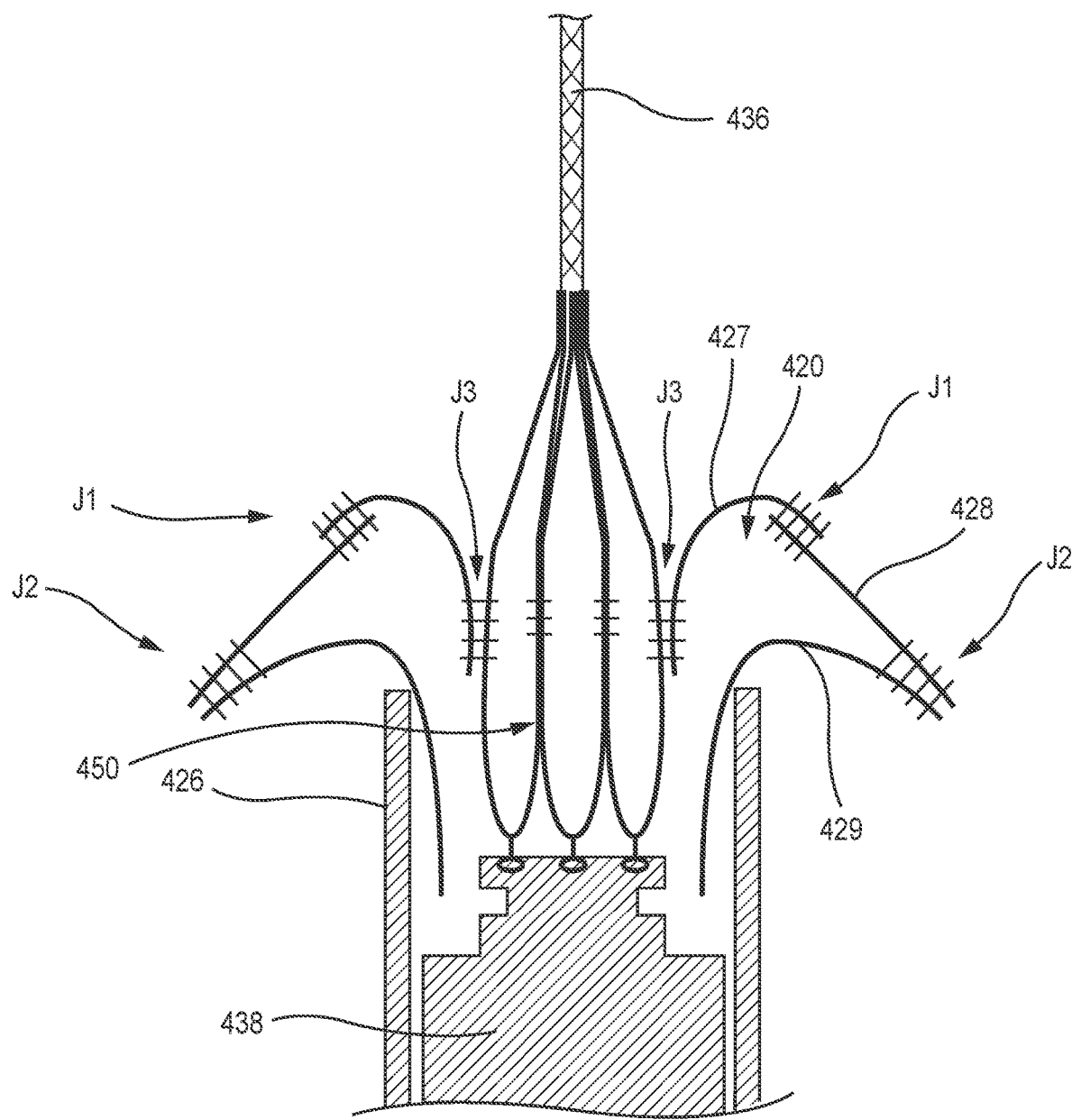
Figure 28:
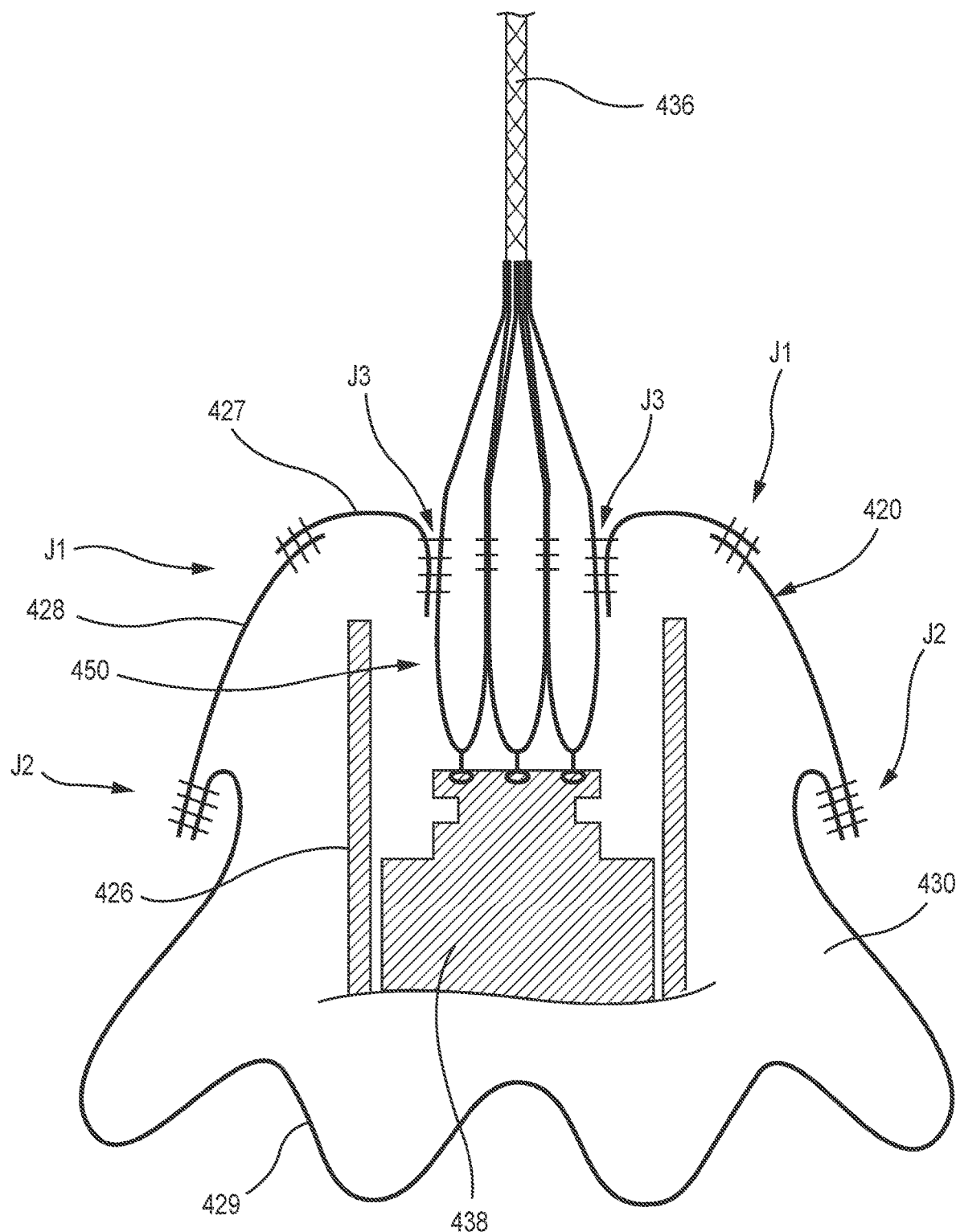

FIG. 25-28 illustrate another embodiment of a prosthetic valve that can be moved between a biased expanded configuration and an inverted configuration in which the outer frame is inverted relative to the inner frame. The valve 400 can be constructed the same as or similar to, and function the same as or similar to any of the valves described herein and in the '572 PCT application, with the addition of the following features. The valve 400 has an outer frame 420 and an inner frame 450 coupled to the outer frame 420. In this embodiment, the outer frame 420 of the valve 400 is formed of three portions (e.g., three cylinders), i.e., a first portion 427, a second portion 428, and a third portion 429, all of which are best shown in FIGS. 27 and 28. The portions 427, 428, 429 can be coupled to one another by any suitable coupling method to allow the portions 427, 428 and 429 to be moved relative to each other. As shown best in FIGS. 27 and 29, the first portion 427 is movably coupled to the second portion 428 via a first joint J1, and the second portion 428 is moveably coupled to the third portion 429 via a second joint J2. The first portion 427 of the outer frame 420 is also coupled to the inner frame 450 via a third joint J3 such that the outer frame 420 can move (e.g., rotate or pivot) relative to the inner frame 450 as described herein. For example, any of the coupling methods described herein can be used (e.g. living hinge, sutures, pins, tabs insertable through openings or slots, etc. or any combination thereof) at each of the joints J1, J2, and J3.

Although the outer frame 420 is shown and described as being formed of three separate portions which are joined together, in other embodiments, an outer frame can be formed of any suitable number of portions or cylinders (e.g., two portions, four portions, five portions, six portions, etc.), which can then be joined to form the outer frame.

As shown in FIG. 26, in use, to dispose the outer frame 420 in an inverted configuration relative to the inner frame 450, the outer frame 420 is folded or inverted distally such that the open free end portion of the outer frame 420 is pointed in an opposite direction as an open free end of the inner frame 450. With the outer frame 420 in the inverted configuration, the valve 400 can be placed within a lumen of a delivery sheath 426 for delivery of the valve 400 to the left atrium of the heart. The delivery sheath 426 can be the same as or similar to any of the delivery sheaths described herein or in the '572 PCT application. In this embodiment, a pusher device 438 is movably disposed within a lumen of the delivery sheath 426 and removably attached to the valve 400. Alternatively, a pusher device similar to pusher 338 can be used that is not attached to the valve 400.

The joints (i.e., joint J1, J2 and joint J3) and outer frame portions (i.e., the first portion 427, the second portion 428, and the third portion 429) of the valve 400 can provide for an easier (e.g., due to less rigidity of the outer frame 420 and/or more focused and selective control of the outer frame 420) and/or faster transition between an inverted and collapsed configuration of valve 400 and an expanded configuration, and vice versa. Further, the joints and portions of the valve 400 can allow the valve 400 to have a lower profile or footprint (e.g., occupy a smaller radial space or diameter), e.g., when transitioning between configurations and orientations.

In use, during reversion of the valve 400 from the inverted and collapsed configuration (e.g., within the delivery sheath 426) to its expanded configuration, the first portion 427 of the outer frame 420, the second portion 428 of the outer frame 420, and the third portion 429 of the outer frame 420 can revert sequentially during the procedure. In other words, the portions 427, 428, 429 of the outer frame 420 can revert in stages as the outer frame 420 exits the delivery sheath 426 within the atrium of the heart. Examples of such stages are shown in FIGS. 26-28.

During delivery of the valve 400 from the delivery sheath 426, as shown by progression in FIGS. 26-28, the second joint J2 disposed between the second portion 428 of the outer frame 420 and the third portion 429 of the outer frame 420 emerges from the delivery sheath 426, allowing the third portion 429 to begin to revert towards an expanded or deployed configuration (as shown, for example, in FIG. 26). Next, as the valve 400 moves further towards the exit (e.g., a distal end opening) of the delivery sheath 426, the first joint J1 disposed between the second portion 428 of the outer frame 420 and the first portion 427 of the outer frame 420 emerges from the delivery sheath 426, allowing the second portion 428 to further revert towards an expanded (as shown, for example, in FIG. 27). Next, as the valve 400 moves even further towards the exit of the delivery sheath 426, and the inner frame 450 begins to emerge from the delivery sheath 426, including the third joint J3 between the inner frame 450 and the first portion 427 of the outer frame 420, the outer frame 420 reverts into its expanded configuration/size (as shown, for example, in FIG. 28).

Upon reversion of the outer frame 420 into its expanded configuration, as shown best in FIG. 28, the inner frame 450 can be decoupled from the pusher device 438 and/or forced out of the delivery sheath 426 such that the inner frame 450 and/or the outer frame 420 can expand further and be suitably seated in the native annulus of the mitral valve.

Similar to the discussion above with respect to the valve 300, a tether 436 (see FIGS. 27 and 28), can be attached to the valve 400 and used to help move the valve 400 out of the lumen of the delivery sheath 426. As described for valve 300, the pusher device 438 and/or the tether 436 can be used to deliver and deploy the valve 400.

Figure 29A:
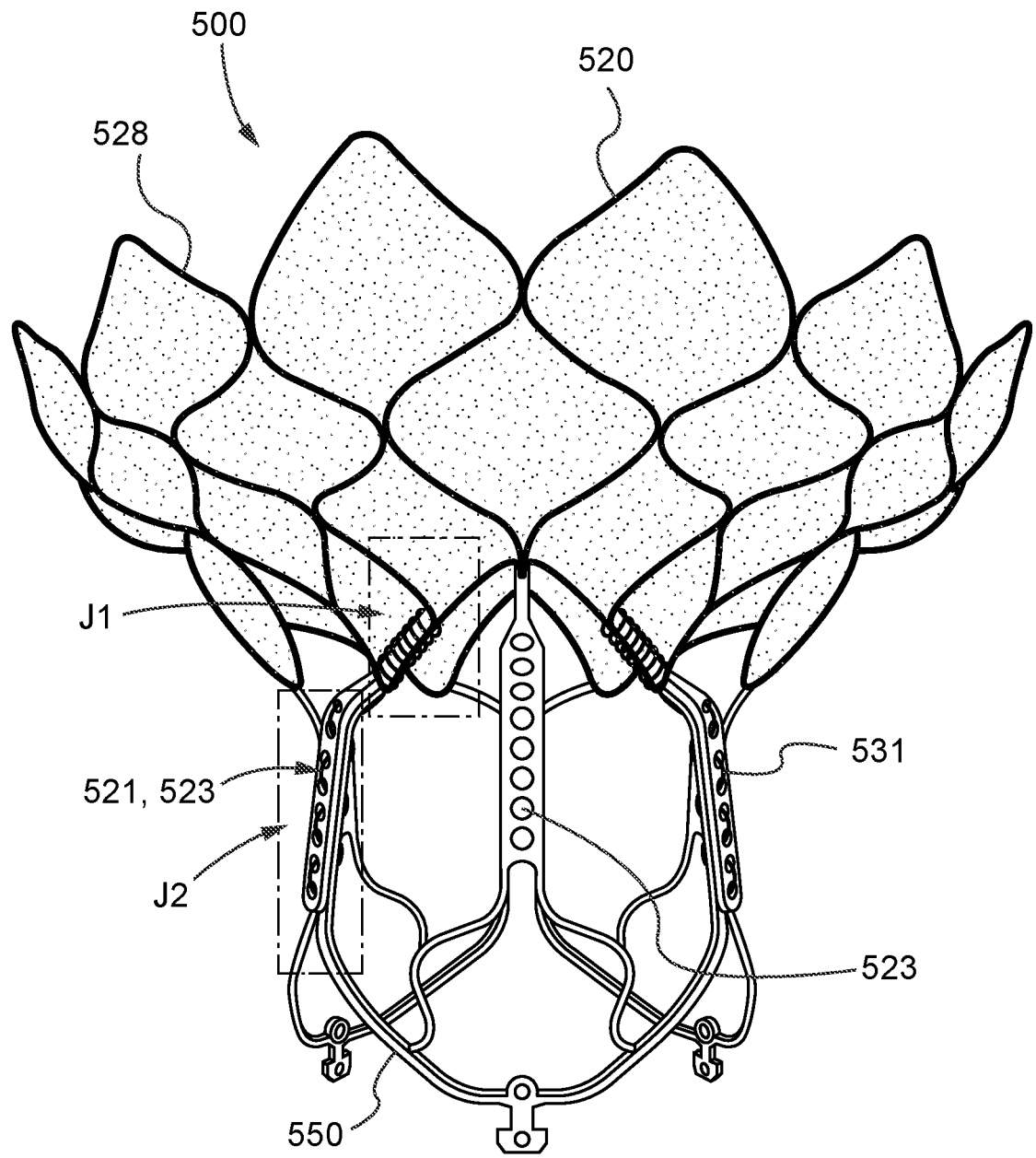
FIG. 29A is a side view of a prosthetic valve, according to an embodiment and shown in an inverted orientation.
Figure 29B:
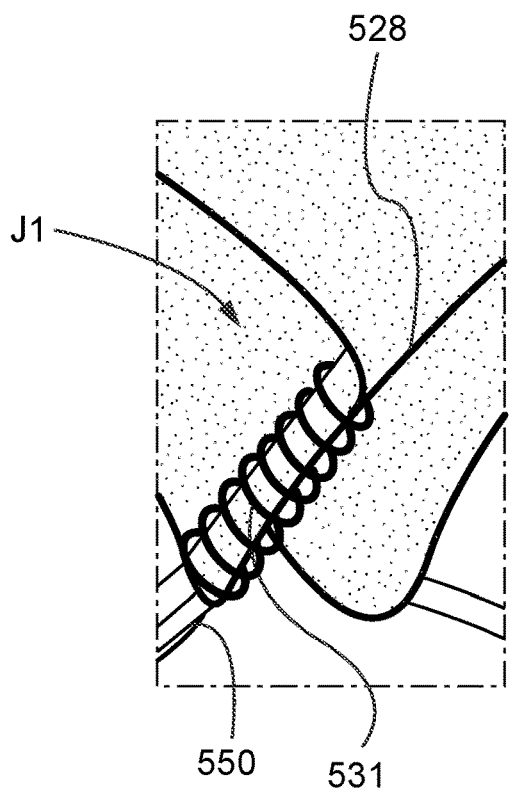
FIGS. 29B and 29C are each an enlarged detail view of a different portion of the prosthetic valve of FIG. 29A.
Figure 29C:
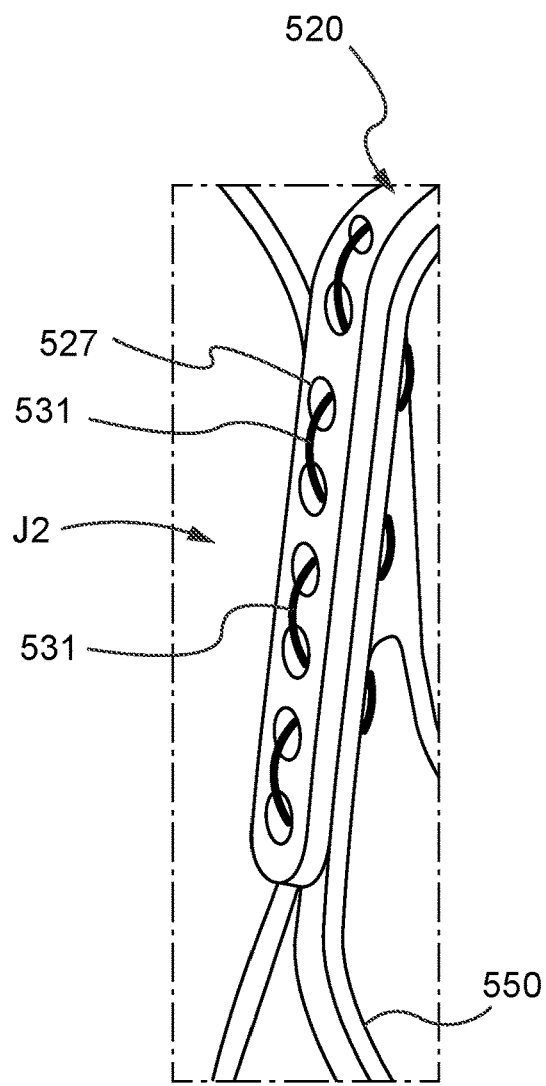

FIGS. 29A-29C illustrate another embodiment of a prosthetic heart valve 500 (also referred to herein as "valve") that can be delivered to a left atrium of a heart in a procedure similar to or the same as the procedures described above, the procedures described in the '572 PCT application, the '704 provisional application or other delivery approach that delivers the valve to the left atrium of the heart. Thus, some details regarding the valve 500 and procedures performed therewith are not described herein. It should be understood that for features and functions not specifically discussed, those features and functions can be the same as or similar to the valves described above or in the '572 PCT application. The valve 500 has an outer frame 520 and an inner frame 550 coupled to the outer frame 520. FIG. 29A illustrates the outer frame 520 in an inverted configuration or position relative to the inner frame 550 (as described above for previous embodiments). In this embodiment, the outer frame 520 of the valve 500 includes two portions, i.e., a first portion 527 and a second portion 528 that can be coupled together at joints, as described in more detail below.

Similar to the discussion with respect to the portions 427, 428, 429 of the valve 400, and the joints J1 and J2, in this embodiment, the first portion 527 of the outer frame 520 is coupled to the second portion 528 of the outer frame 520 via a first joint J1, and the first portion 527 is coupled to the inner frame 550 via a second joint J2. In this embodiment, first portion 527 of the outer frame 520 defines multiple apertures 521 and the inner frame 550 of the valve 500 defines multiple apertures 523 (see also, e.g., the openings of the body portion 242 of the inner frame 550 of the valve 500, described above). As shown best in FIG. 29C, the apertures 521 and the apertures 523 can be aligned, and one or more connecting members 531 (e.g., sutures or wires) are passed through the one or more apertures 521 of the first portion 527 of the outer frame 520 and one or more apertures 523 of the inner frame 550 to couple the first portion 527 of the outer frame 520 to the inner frame 550 at the second joint J2. In this manner, the inner frame 550 of the valve 500 and the outer frame 520 of the valve 500 can be coupled together such that the outer frame 520 can move relative to the inner frame (e.g., rotate, pivot, articulate) between an inverted position relative to the inner frame 550 and a non-inverted position in which the outer frame 520 can assume a biased expanded configuration with the inner frame 550 nested within the outer frame 520 as described above for previous embodiments.

As shown, for example, in FIG. 29B, the first joint J1 between the first portion 527 and the second portion 528 of the outer frame 520 is formed by wrapping one or more connecting member 531 (e.g., suture or wire) around a strut of the first portion 527 and around a strut of the second portion 528. For example, the strut of the first portion 527 and the strut of the second portion 528 can be aligned with one another prior to application of the connecting member(s) 531 thereto. In an embodiment of a valve having an outer frame with for example, three portions, such as valve 400, the second portion and the third portion of the outer frame can be coupled together using either of the coupling methods described for joint J1 and J2 of valve 500. While the valve 500 is shown as having a first joint J1 between the first portion 527 and the second portion 528, and a second joint J2 between the inner frame 550 and the outer frame 520, in some embodiments, any suitable number or type of joints can be used to couple any suitable number of portions of the outer frame 520 together, and the inner frame 550 to the outer frame 520.

FIGS. 30A-42C illustrate various embodiments of a coupling joint(s) for coupling an inner frame to an outer frame of a prosthetic heart valve such that the valve can be reconfigured between a biased expanded configuration for implantation in the heart (e.g., within a native mitral annulus) and a delivery configuration that has a smaller outer perimeter or profile (e.g., inverted configuration) as discussed above, for example, with respect to valve 100. More specifically, the embodiments of FIGS. 30-42C illustrate various embodiments of different coupling joints for coupling the outer frame to the inner frame such that the outer frame can be moved (e.g., rotated, pivoted, flexed) relative to the inner frame between a first configuration and a second configuration in which the outer frame is inverted relative to the inner frame. Each of the embodiments of a prosthetic heart valve described with respect to FIGS. 30A-42C can include the same or similar features and can function the same as or similar to the prosthetic heart valves described above with respect to, for example, valve 100, 200 and 300. Thus, some features and details of the embodiments described with respect to FIGS. 30A-42C are not described below.

Figure 30A:
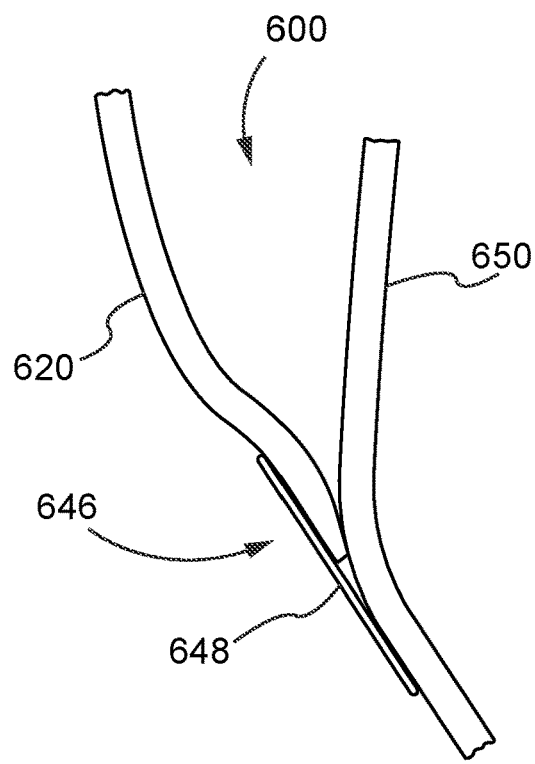
FIG. 30A is a side view of a portion of a prosthetic heart valve, showing a coupling joint and an outer frame of the valve in a first configuration, according to an embodiment.
Figure 30B:
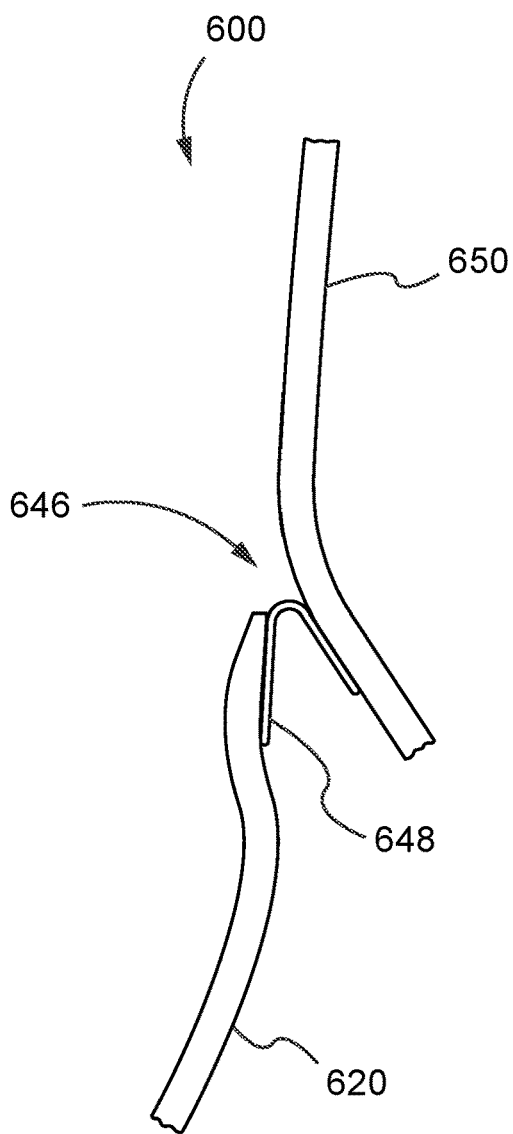
FIG. 30B is a side view of the portion of the prosthetic valve of FIG. 30A, showing the coupling joint and the outer frame in a second configuration.

FIGS. 30A and 30B illustrate a portion of a prosthetic heart valve, which includes an inner frame assembly having an inner frame 650 and an outer frame assembly having an outer frame 620. The prosthetic heart valve 600 (also referred to as "prosthetic valve" or "valve") can be constructed similar to or the same as, for example, the prosthetic heart valve 100 or valve 200 described above. Specifically, FIGS. 30A and 30B illustrate a portion of the outer frame 620 and a portion of the inner frame 650 shown with the outer frame 620 in a first configuration and a second configuration, respectively. The outer frame 620 and the inner frame 650 are coupled via a coupling joint 646. In the illustrated embodiment of FIGS. 30A and 30B, the coupling joint 646 includes a hinge member 648. In some embodiments, the hinge member 648 can include a living hinge. The hinge member 648 can be formed of a material such that the hinge member 648 can flex or bend and permit movement of the outer frame 620 relative to the inner frame 650. For example, as described above for previous embodiments, the coupling joint 646 (i.e., hinge member 648) allows the outer frame 620 to be moved from the first configuration as shown in FIG. 30A to the second configuration, as shown in FIG. 30B, in which the outer frame 620 is inverted relative to the inner frame 650.

The hinge member 648 can be made of any suitable material including, but not limited to, a polymer, an extracted natural tissue, an artificially engineered tissue, an elastic material (including superelastics), and/or the like. In some embodiments, the hinge member 648 is made of the same materials as the outer frame 620 and/or the inner frame 650. In some embodiments, the hinge member 648 can be integrally formed and/or fused with the outer frame 620 and/or the inner frame 650. In other embodiments, the hinge member 648 can be attached to the outer frame 620 and/or the inner frame 650 by any suitable coupling technique, including suturing, spin coating, and/or the like. As shown in FIG. 30B, when the outer frame 620 is in the second configuration (i.e., inverted), the hinge member 648 flexes or bends with the outer frame 620.

Figure 31A:
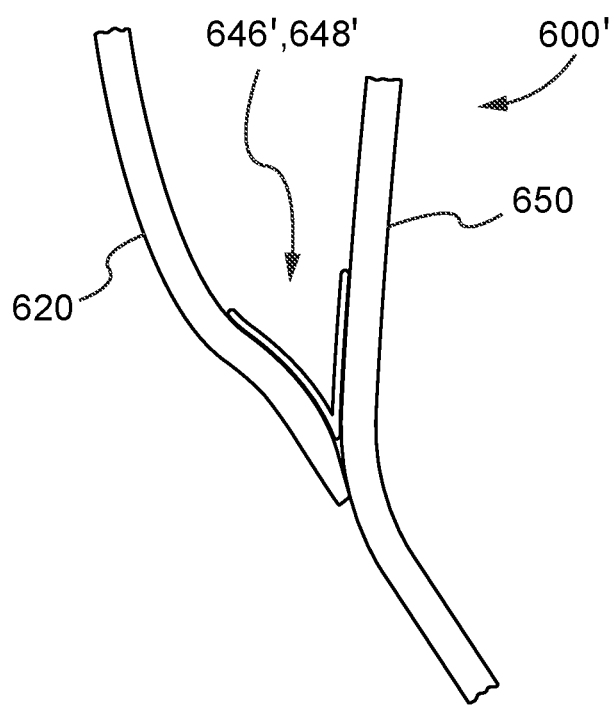
FIG. 31A is a side view of a portion of a prosthetic heart valve, showing a coupling joint and an outer frame of the valve in a first configuration, according to an embodiment.
Figure 31B:
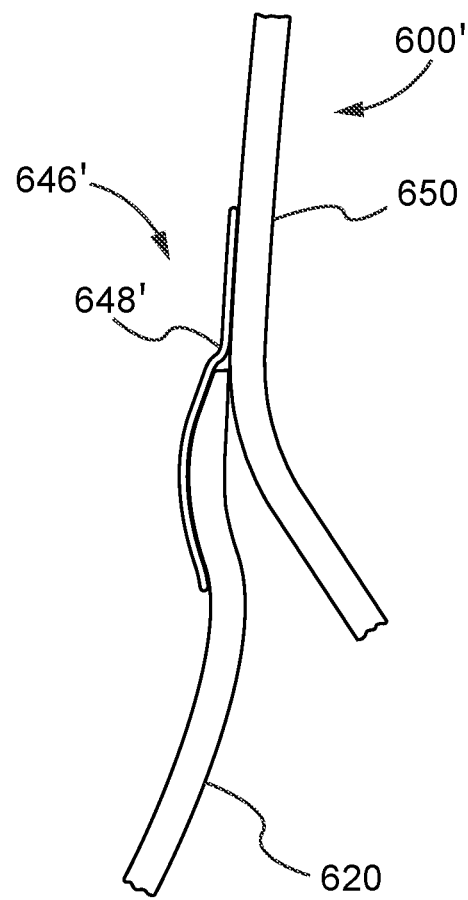
FIG. 31B is a side view of the prosthetic valve of FIG. 31A, showing the coupling joint and the outer frame in a second configuration.

FIGS. 31A and 31B illustrate a portion of a prosthetic heart valve 600' that includes the inner frame 650 and the outer frame 620. In this embodiment, the inner frame 650 and outer frame 620 are coupled at a coupling joint 646' that includes a hinge member 648' that is disposed in a substantially V-shape between the inner frame 650 and the outer frame 620. As with the previous embodiment, the hinge member 648' can be coupled to the outer frame 620 and the inner frame 650 in such a manner so as to allow for the outer frame 620 to move relative to the inner frame 650 between a first configuration as shown in FIG. 31A and a second configuration as shown in FIG. 31B. The hinge member 648' can be formed with the same or similar materials as described above for hinge member 648, and can be coupled to the inner frame 650 and the outer frame 620 with any of the coupling techniques described for hinge member 648. As shown in FIG. 31B, when the outer frame 620 is moved to the second configuration (i.e., inverted), the hinge member 648' can bend or flex with the outer frame 620.

Figure 32A:
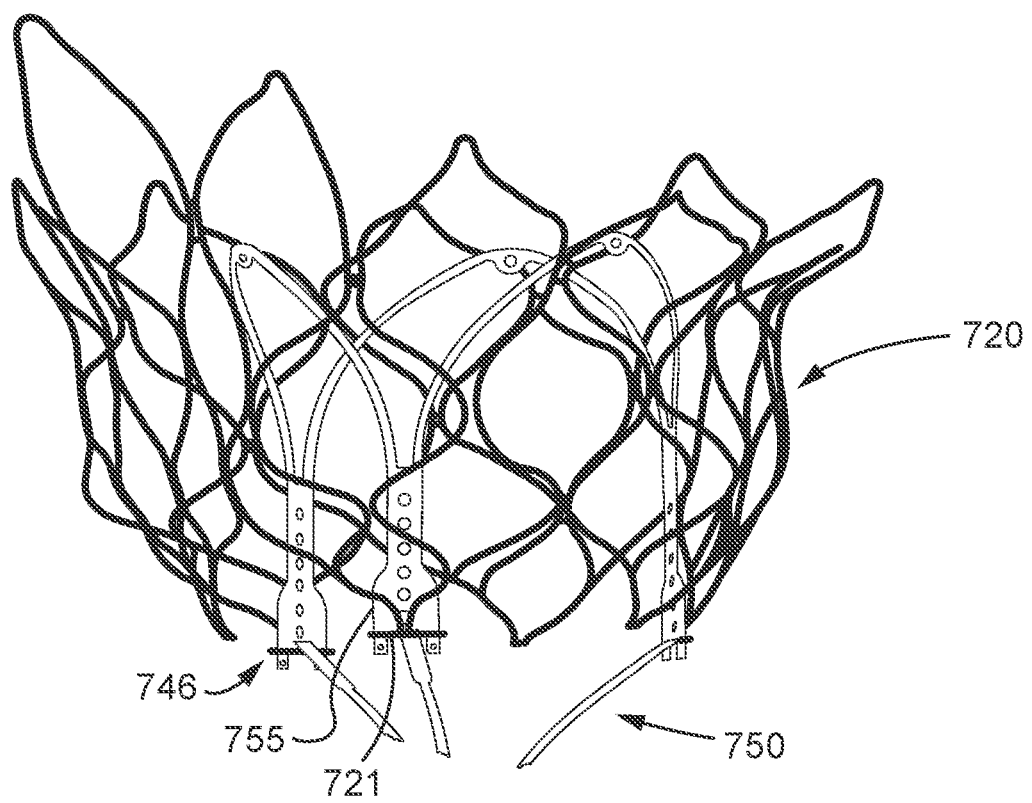
FIG. 32A is a perspective view of a portion of a prosthetic valve, according to an embodiment.
Figure 32B:
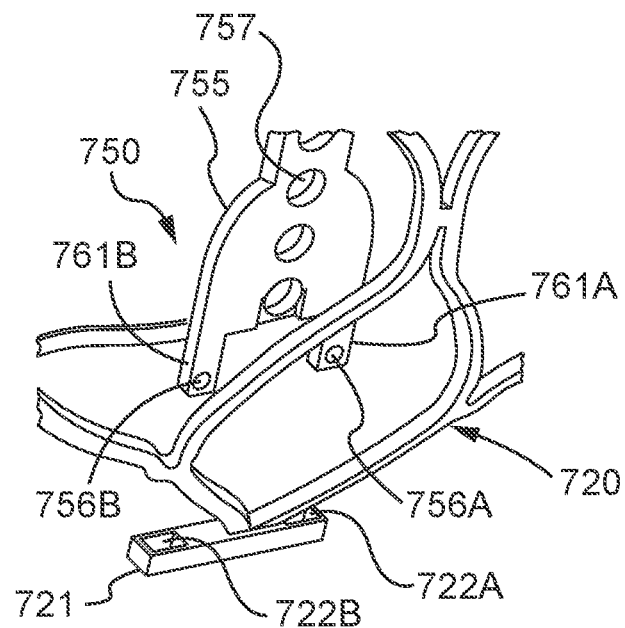
FIG. 32B is a detailed view of a portion of the valve of FIG. 32A, showing a coupling portion that includes a tab and slot arrangement in a disengaged position.
Figure 32C:
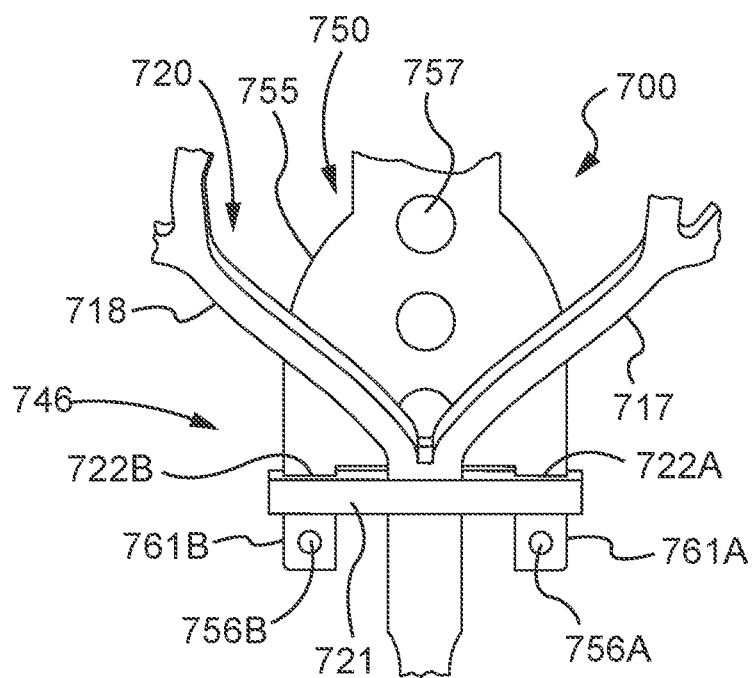
FIG. 32C is a detailed view of a portion of the valve of FIG. 32A, showing a coupling portion in an engaged position.

FIGS. 32A-32C illustrate portions of a prosthetic heart valve 700. The prosthetic heart valve (also referred to as "prosthetic valve" or 'valve") 700 includes an outer frame assembly 710 with an outer frame 720, and an inner frame assembly 740 with an inner frame 750. The valve 700 also includes multiple coupling joints 746 to couple the outer frame 720 to the inner frame 750 such that the outer frame can be moved between a first configuration (as shown in FIGS. 32A-32C) and a second configuration (not shown) in which the outer frame 720 is inverted relative to the inner frame 750. As best illustrated in FIGS. 32B-32C, each coupling joint 746 includes a support member 721 that defines two slots 722A and 722B, and corresponding coupling portions 755 of the inner frame 750 that include tabs 761A and 761B. Also defined by the tabs 761A and 761B are holes 756A and 756B.

To couple the outer frame 720 to the inner frame 750, the tabs 761A and 761B are inserted into the corresponding slots 722A and 722B of the outer frame 720 as shown in FIGS. 32A and 32C. Thus, the tab 756A is received within the slot 722A and the tab 756B is received within the slot 722B as best shown in FIG. 32C. In this manner, mechanical attachment can be achieved between the outer frame 720 and the inner frame 750. In some embodiments, the support member 721 can be formed integrally with the outer frame 720. In such an embodiment, the outer frame 720 (and support member 755) can be made of any suitable, flexible material (e.g., a shape memory metal such as Nitinol) that permits articulation between the frame portions of the outer frame 720, such as frame portions 717 and 718 and the support member 721 such that the outer frame 720 can be moved between the first configuration and the second configuration (i.e., inverted). In some embodiments, the frame portions (e.g., frame portions 717, 718) can be formed separately from the support member 721 and can be coupled to the support member 721 with a pivot joint such as a ball and socket. In such an embodiment, the outer frame 720 can pivot relative to the support member 721 when moved between the first configuration and the second (inverted) configuration.

The interlocking nature of the tabs 761A and 761B within the slots 722A, 722B provides for load bearing without additional components such as sutures. In some embodiments, as illustrated, the tabs 761A, 761B can include the holes 760A, 760B that can receive a stop member (not shown) such as, for example, a pin and/or other component to prevent the tabs 761A, 761B from coming out of the slots 722A, 722B. In some embodiments, one or more strands or suture can be used as the stop member. For example, the suture strands can be threaded through the holes 756A, 756B and/or wrapped about the tabs 761A, 761B. As best illustrated in FIGS. 32B-32C, the coupling portion 755 of the inner frame 750 can also include one or more holes 757 for aiding in attachment (e.g., via sutures) of other components, such as, for example, the covering 232 illustrated in FIG. 3.

Although two tabs 761A, 761B and two slots 722A, 722B are included at coupling joints 746, it should be understood that variations from the illustrated embodiment in FIGS. 32A-32C are within the scope of this disclosure. For example, any suitable number of tabs and slots can be employed to attach the outer frame 720 and the inner frame 750, including a single tab/slot mechanism. As another example, any suitable geometry of the support member 721 and/or the coupling portion 755 can be employed.

Figure 33A:
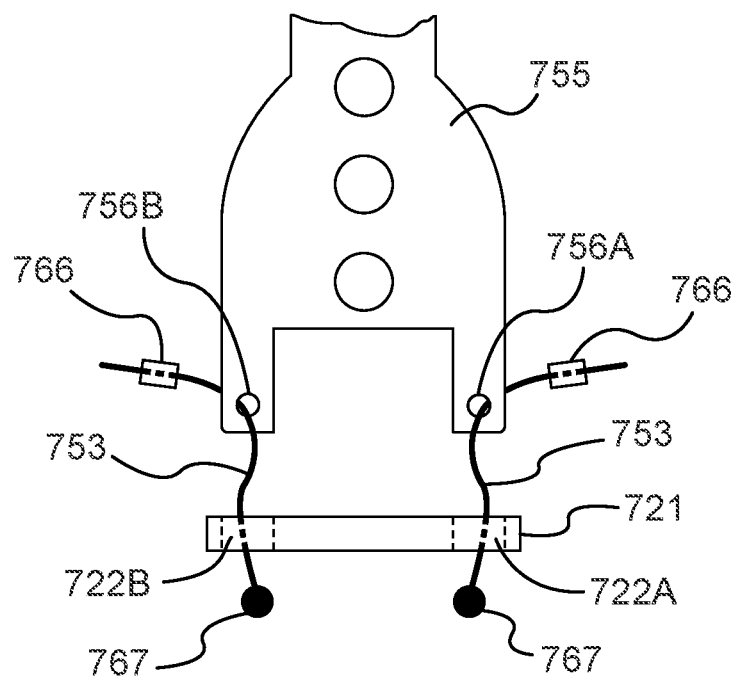
FIG. 33A illustrates a portion of the valve of FIG. 32A illustrating a coupling joint according to another embodiment.
Figure 33B:
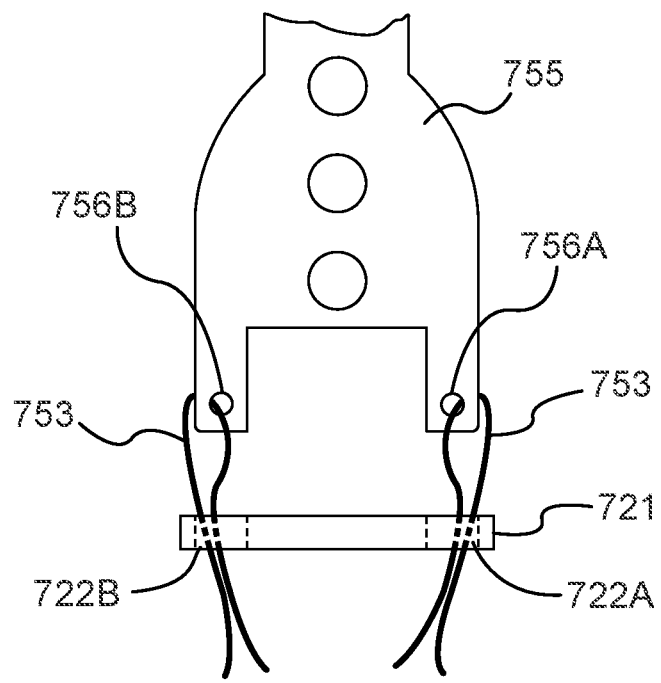
FIG. 33B illustrates a portion of the valve of FIG. 32A illustrating a coupling joint according to yet another embodiment.

To deliver the valve 700 to a heart of a patient, in some cases it may be desirable to deliver the outer frame 720 and the inner frame 750 prior to being coupled together at the coupling joints 746. In such an embodiment, the outer frame 720 and the inner frame 750 can be loosely coupled with a suture strand 753 as shown in FIGS. 33A and 33B. The suture strand 753 is threaded through the opening 756 of the coupling portion 755 of the inner frame 750 and through the slot 722 of the support member 721 of the outer frame 720. Although a single suture strand 753 is shown, it should be understood that a suture strand 753 can be disposed through each of the slots 722 of the outer frame 720 and the openings 756 of the inner frame 750. With the inner frame 750 coupled to the outer frame 720 via the suture strand 753, the outer frame 720 can be inverted separately from the inner frame 750 and then loaded into a delivery sheath (not shown) along with the inner frame 750 such that the inner frame 750 is disposed proximal of the outer frame 720 within the delivery sheath. As shown in FIG. 33A, a clip 766 and a stop element 767 are coupled to the suture strand 753 and can be used to secure the inner frame 750 to the outer frame 720 as described in more detail below.

More specifically, to deploy the valve 700 into the heart of a patient, a distal end portion of the delivery sheath is disposed within the left atrium and the outer frame 720 is moved outside of the distal end of the delivery sheath and into the left atrium. Upon being moved outside of the delivery sheath, the outer frame 720 can revert and assume a biased expanded configuration. The inner frame 750 can be moved into a nested position within the outer frame 720 and the tabs 761A and 761B can be disposed within corresponding slots 722A and 722B of the support member 721 of the outer frame 720. The suture strand 753 can be pulled proximally such that the stop element 767 (coupled to the suture strand 753) is pulled against a distal side of the support member 721, and the clip 766 can be slid distally toward the support member 721 to secure the inner frame 750 to the outer frame 720. The clip 766 can be capable of sliding along the suture strand 753 while having sufficient friction force to hold the clip 766 to the suture strand 753 in a desired location.

FIG. 33B illustrates a variation to the above embodiment in that the suture strand 753 does not have a clip or stop element coupled thereto. In this example embodiment, the suture strand 753 is threaded through the slot 722 of the support member 721 from a distal side, through the opening 759 of the tab 761, and then back through the slot 722 from a proximal side such that the two end portions of the suture strand 753 extend from the distal side of the support member 721. The two end portions of the suture strand 753 can extend through a gap between the native mitral annulus, through the left ventricle and out of the apex of the heart. For example, a procedural catheter can be inserted through a puncture site at the apex and the two ends of the suture strand 753 can extend through a lumen of the procedural catheter. The outer frame 720 and the inner frame 750 can be deployed as described for FIG. 33A, and then the two suture end portions can be pulled taut to secure the tab 756 within the slot 722. For example, the two suture end portions can be tied to form a knot on the distal side of the support member 721 or otherwise secured in place to prevent the tab 761 from pulling out of the slot 722.

Figure 34A:
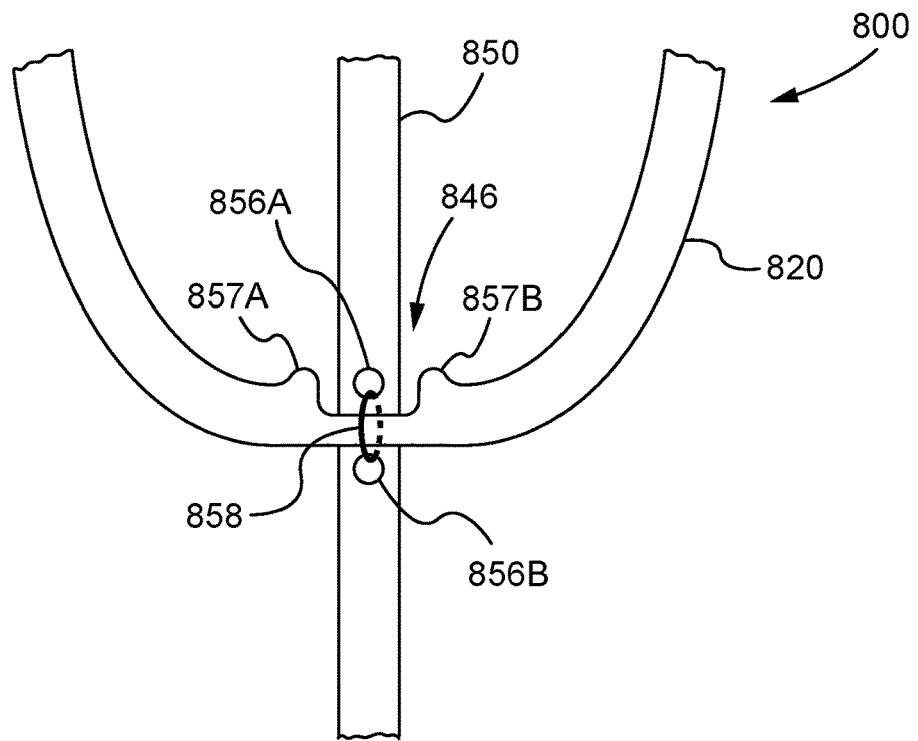
FIG. 34A is a side view of a portion of a prosthetic heart valve, showing a coupling portion and an outer frame of the valve in a first configuration, according to an embodiment.
Figure 34B:
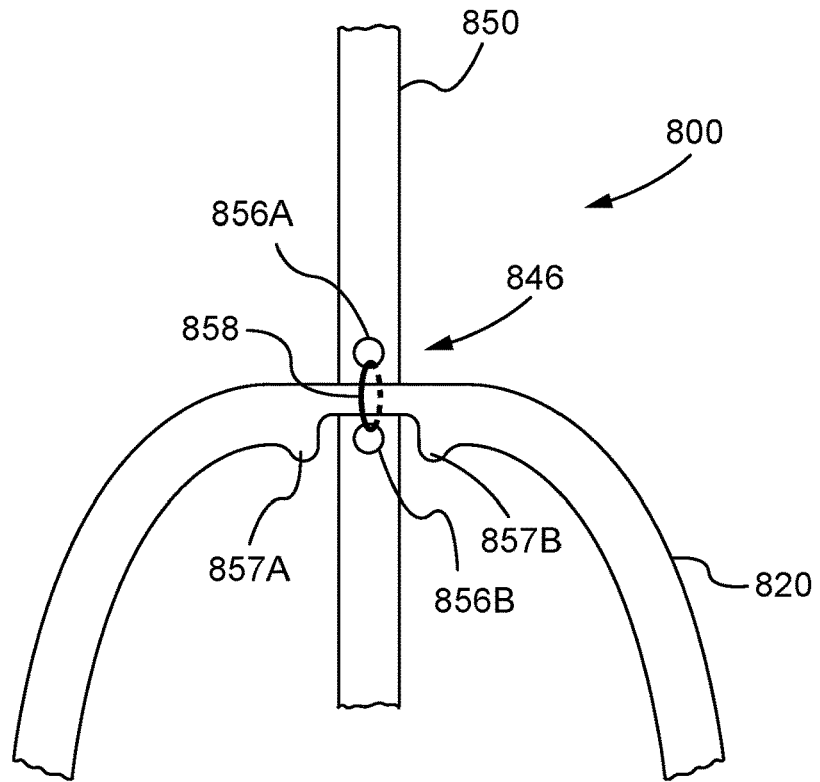
FIG. 34B is a side view of the portion of the prosthetic heart valve of FIG. 34A showing the coupling joint and the outer frame in a second configuration.

FIGS. 34A and 34B illustrate a portion of an outer frame 820 and a portion of an inner frame 850 of a prosthetic heart valve 800, according to an embodiment. The outer frame 820 is coupled to the inner frame 820 at a coupling joint 846 such that the outer frame 820 can be moved (e.g., rotated, pivoted) between a first configuration relative to the inner frame 850, as shown in FIG. 34A, and a second configuration relative to the inner frame 850, as shown in FIG. 34B, in which the outer frame 820 is inverted relative to the inner frame 850. In this embodiment, the coupling joint 846 includes holes 856A and 856B defined by the inner frame 850 and a suture 858 that is threaded or wrapped through the holes 856A and 856B. More specifically, a portion of the outer frame 820 is disposed against a portion of the inner frame 850 and the suture 858 is wrapped around the portion of the outer frame 820 and through the holes 856A and 856B. One or more sutures 858 can be used and/or the suture(s) 858 can be wrapped multiple times around the portion of the outer frame 820 and through the holes 856A and 856B. The suture 858 can be made of any suitable material, including shape memory polymers, polyester, tissue, and/or the like. In some embodiments (not shown), an interface layer of Nitinol or other suitable material can be disposed between the outer frame 820 and the inner frame 850 to prevent abrasive contact. Such an interface material is described with respect to valve 1100.

As also illustrated in FIGS. 34A and 34B, the outer frame 820 includes protrusions 857A, 857B formed thereon. The protrusions 857A, 857B are sized and located such that, after the outer frame 820 and the inner frame 850 are coupled with the suture 858, the protrusion 857A is located on one side of the suture 858, and the protrusion 857B is located on the opposite side of the suture 858. In this manner, the outer frame 820 has limited lateral mobility with respect to the inner frame 850 due to the suture 858 being constrained between the protrusions 857A, 857B.

In some embodiments, the position of the protrusions 857A, 857B can be manipulated to affect the desired lateral mobility of the outer frame 820. In some embodiments, while the holes 856A, 856B are illustrated as positioned to have a distance between them that is greater than the diameter/width of the outer frame 820, in some embodiments, the outer frame 820 can have a greater diameter/width than the distance between the holes 856A, 856B. In other words, the outer frame 820 overlaps a portion of the holes 856A, 856B.

Figure 35:
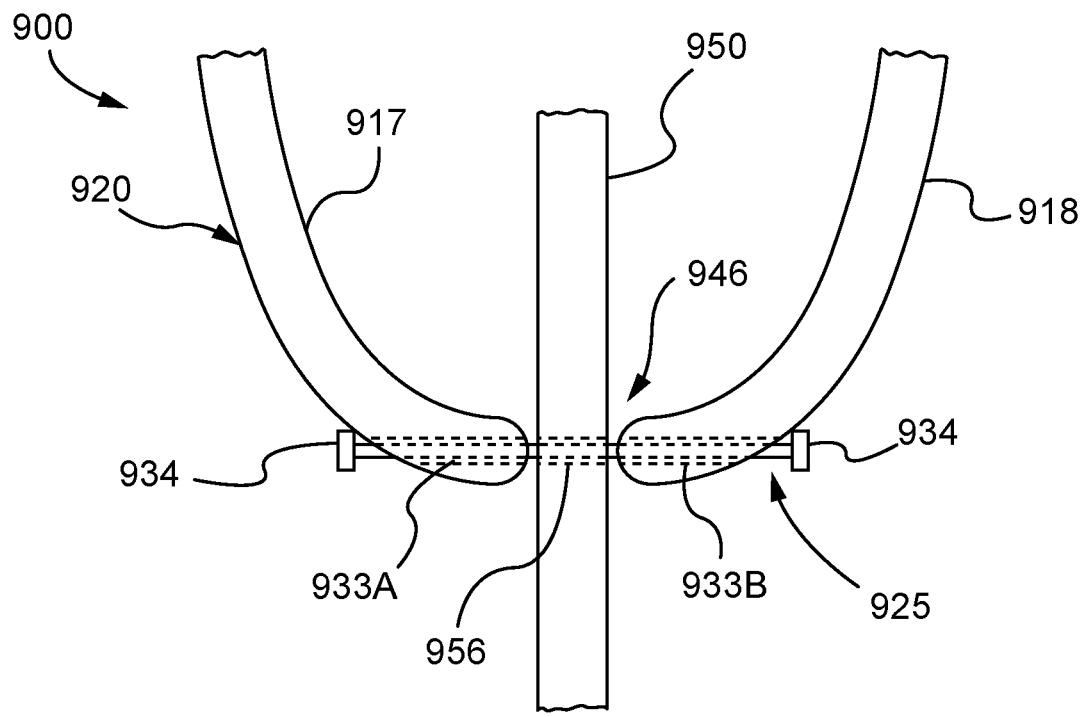
FIG. 35 is a side view of a portion of a prosthetic heart valve, showing a coupling portion that includes a pin joint, according to an embodiment.

FIG. 35 illustrates a portion of an outer frame 920 and a portion of an inner frame 950 of a prosthetic heart valve 900, according to another embodiment. The outer frame 920 is coupled to the inner frame 920 at a coupling joint 946 such that the outer frame 920 can be moved (e.g., rotated, pivoted) between a first configuration relative to the inner frame 950, as shown in FIG. 35, and a second configuration relative to the inner frame 850 (not shown), in which the outer frame 920 is inverted relative to the inner frame 950. In this embodiment, the coupling joint 946 includes a pin assembly 925 that can be received through through-holes 933A and 933B defined by frame portions 917 and 918, respectively, of outer frame 920 and through a corresponding through-hole 956 defined by the inner frame 950.

The pin 925 includes stops 934 disposed on the ends to prevent the pin 925 from being removed. One or both of the stops 934 can be removably coupled to the ends of the pin 925. For example, the stops 934 can be coupled to the pin 925 in any suitable manner including, but not limited to, threaded attachment, compression fit, adhesive (including pressure sensitive adhesives) and/or the like. The diameter/width of the pin 925 is less than the diameter/width of the through-hole 956 and the diameter/width of the through-holes 933A and 933B, and the diameter/width of the stops 934 is greater than the diameter/width of the through-hole 956 and the diameter/width of through-holes 933A, 933B. In this manner, the stops 934 can restrict lateral movement between the outer frame 920 and the inner frame 950, but permit the relative rotation of the outer frame 920 about an axis defined by the length of the pin 925.

In some embodiments, the pin 925 can be made of any suitable rigid material, such as metal. In other embodiments, the pin 925 can be made of any suitable flexible material, such as a polymer. In some embodiments (not shown), sutures are employed instead of the pin assembly 958 to restrict lateral movement between the outer frame 920 and the inner frame 950.

Figure 36:
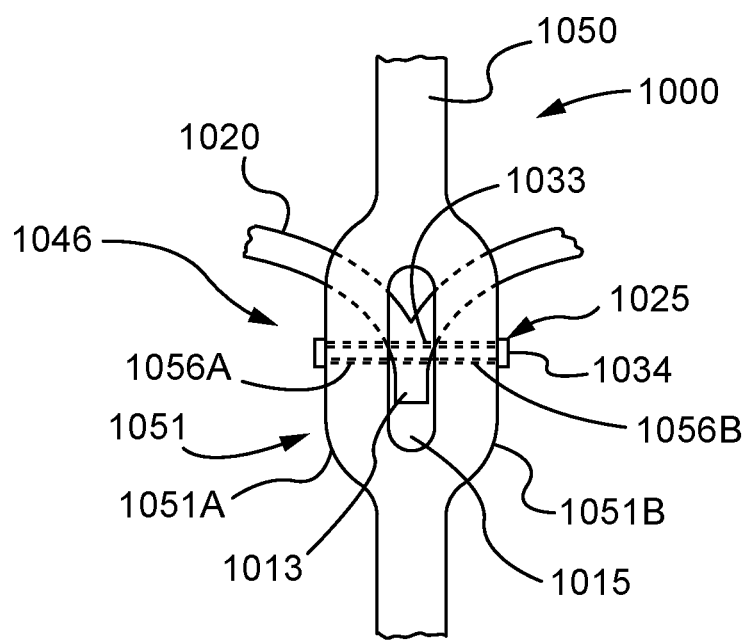
FIG. 36 is a side view of a portion of a prosthetic heart valve, showing a coupling portion that includes a pin joint, according to another embodiment.

FIG. 36 illustrates a portion of an outer frame 1020 and a portion of an inner frame 1050 of a prosthetic heart valve 1000, according to an embodiment. The outer frame 1020 is coupled to the inner frame 1050 at a coupling joint 1046 such that the outer frame 1020 can be moved (e.g., rotated, pivoted) between a first configuration relative to the inner frame 1050, as shown in FIG. 36, and a second configuration relative to the inner frame 1050 (not shown), in which the outer frame 1020 is inverted relative to the inner frame 1050. The coupling joint 1046 is described in detail below.

In this embodiment, the inner frame 1050 includes a loop structure 1051 that includes arms 1051A, 1051B that define an opening 1015 between the arms 1051A, 1051B. The loop structure 1051 also includes through-holes 1056A, 1056B defined by arms 1051A, 1051B, respectively.

The outer frame 1020 includes a stub portion 1013 sized to be disposable within the opening 1015 of the inner frame 1050 and defines a through-hole 1033 configured to be substantially aligned with the through-holes 1056A, 1056B of inner frame 1050.

To couple the outer frame 1020 to the inner frame 1050, a pin 1025 is inserted through the through-hole 1056A, the through-hole 1033 and the through-hole 1056B. Similar to the pin 925, and as illustrated in FIG. 36, the pin 1025 can include stops 1034 on ends thereof to prevent the pin 1025 from being removed. The pin 1025 and the stops 1034 can be constructed the same as or similar to the pin 925 and stops 934 described above. The diameter/width of the pin(s) 1025 is less than the diameter/width of the through-holes 1056A, 1056B and the diameter/width of the through-hole 1033, while the diameter/width of the stops 1034 is greater than the diameter/width of the through-holes 1056A, 1056B and the diameter/width of the through-hole 1033. In this manner, the pin 1025 can restrict lateral movement between the outer frame 1020 and the inner frame 1050, but permit the relative rotation of the outer frame 1020 about an axis defined by the length of the pin 1025.

Figure 37:
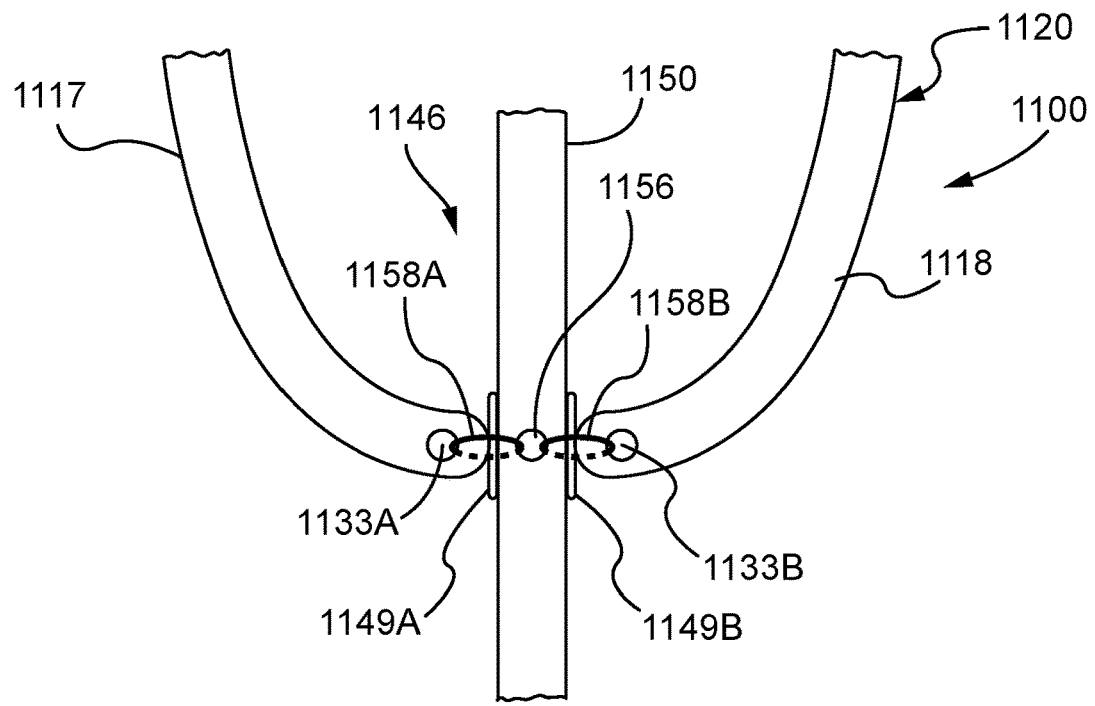
FIG. 37 is a side view of a portion of a prosthetic heart valve, showing a coupling portion that includes a suture hinge mechanism, according to an embodiment.

FIG. 37 illustrates a portion of an outer frame 1120 and a portion of an inner frame 1150 of a prosthetic heart valve 1100, according to an embodiment. The outer frame 1120 is coupled to the inner frame 1120 at a coupling joint 1146 such that the outer frame 1120 can be moved (e.g., rotated, pivoted) between a first configuration relative to the inner frame 1150, as shown in FIG. 37, and a second configuration (not shown) relative to the inner frame 1150, in which the outer frame 1120 is inverted relative to the inner frame 1010. In this embodiment, the coupling joint 1146 includes sutures attached to the inner frame 1150 and to the outer frame 1120 via holes defined in each as described in more detail below.

More specifically, the inner frame 1150 defines an opening 1156. The outer frame 1150 includes frame portions 1117 and 1118 disposed on each side of the inner frame 1150. The frame portions 1117 and 1118 each define a hole 1133A and 1133B, respectively.

As shown in FIG. 37, a suture portion 1158A is threaded or looped through the opening 1133A and the opening 1156 and a suture portion 1158B is threaded or looped through the opening 1133B and the opening 1156. The suture portions 1158A, 1158B can be tied or otherwise secured in position. The suture portions 1158A, 1158B thus secure the frame portions 1117 and 1118 to the inner frame 1150, while allowing motion of the frame portions 1117 and 1118 relative to the inner frame 1150 to move the outer frame 1120 between the first configuration and the second inverted configuration. The sutures 1158A, 1158B provide for a hinge-like effect. It is understood that while sutures 1158A, 1158B are shown to be independent of each other, any suitable suture pattern can be employed, such as the use of a single suture running through the opening 1156 and the openings 1133A, 1133B, a suture running between the openings 1133A and 1133B, combinations thereof, and/or the like. Furthermore, each of the suture portions 1158A and 1158B can include one or more suture strands and/or one or more wraps of the suture portion through the openings.

FIG. 37 also illustrates interface members 1149A, 1149B that can be disposed between the inner frame 1150 and the frame portions 1117 and 1118, respectively, of outer frame 1120. The interface members 1149A, 1149B are sized and located to substantially prevent abrasive contact between the inner frame 1150 and the outer frame 1120, and/or to substantially prevent slippage of the outer frame 1120. In some embodiments (not shown), the interface members 1149A, 1149B can be continuous with each other, and can encircle the inner frame 1150, save for openings consistent with the opening 1156. The interface members 1149A, 1149B can be formed of any suitable material, such as, for example, polyester.

Figure 38:
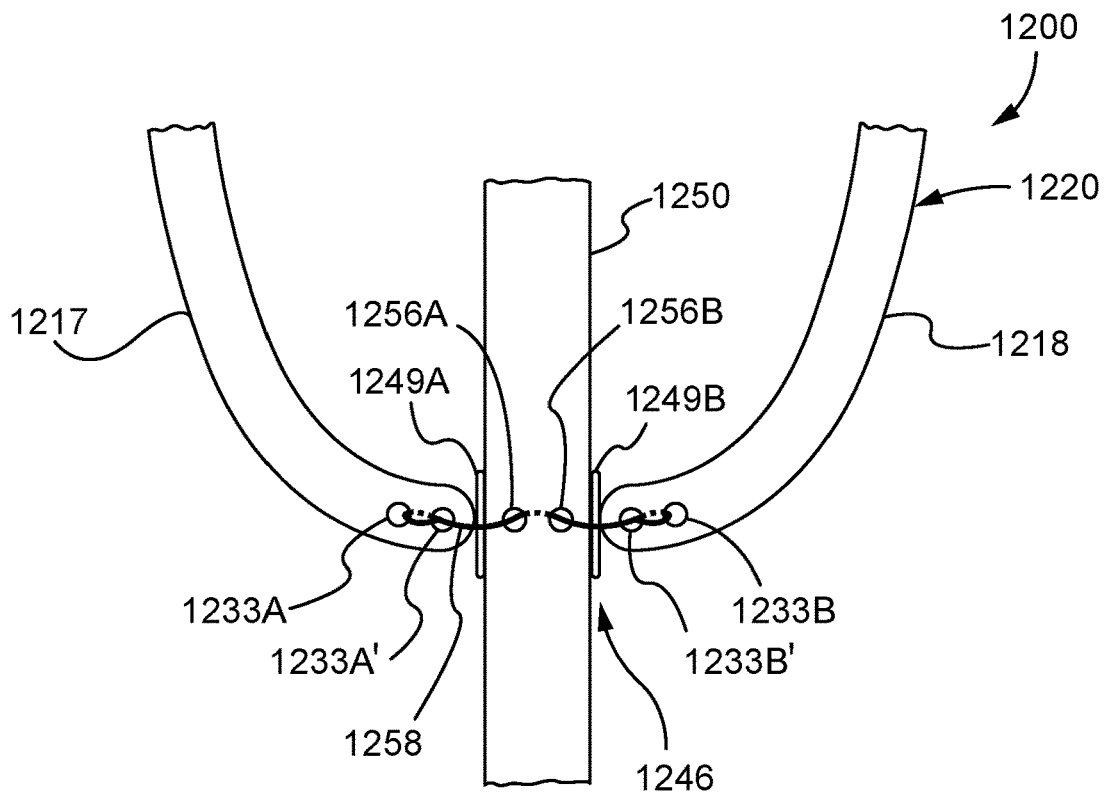
FIG. 38 is a side view of a portion of a prosthetic heart valve, showing a coupling portion that includes a suture hinge mechanism, according to another embodiment.

FIG. 38 illustrates a portion of an outer frame 1220 and a portion of an inner frame 1250 of a prosthetic heart valve 1200, according to an embodiment. The outer frame 1220 is coupled to the inner frame 1250 via coupling joints 1246. This embodiment is similar to the previous embodiment in that the coupling portion 1246 includes sutures attached to holes in the outer frame 1220 and holes in the inner frame 1250.

More specifically, the inner frame 1250 defines a pair of openings 1256A and 1256B. The outer frame 1250 includes frame portions 1217 and 1218 disposed on each side of the inner frame 1250. The frame portion 1217 defines a pair of openings 1233A and 1233A' and the frame portion 1218 defines a pair of openings 1233B and 1233B'. In this embodiment, a suture portion 1258 is threaded or looped through the openings 1233A, 1133A' then a portion of the suture 1258 is inserted through a front side of the opening 1256A, back through the opening 1256B, into the opening 1233B and looped through the opening 1233B'. The suture 1258 can be tied or otherwise secured in position.

The suture 1258 thus secures the frame portions 1217 and 1218 to the inner frame 1250, while allowing motion of the frame portions 1217 and 1218 relative to the inner frame 1250 to move (e.g., rotate, pivot) the outer frame 1220 between a first configuration (as shown in FIG. 38) and a second inverted configuration (not shown). The single suture 1258 through openings 1256A and 1256B may help reduce binding during movement of the outer frame 1220. Although a single suture 1258 is shown, it should be understood that the suture 1258 can include one or more strands of suture material. In addition, any suitable suture pattern can alternatively be employed and the suture 1258 one or more wraps of the suture through the openings. Also shown in FIG. 38, interface members 1249A and 1249B can be included to prevent abrasive contact between the inner frame 1250 and the outer frame 1220. The interface members 1249A, 1249B can be the same as the interface members 1149A, 1149B described above.

Figure 39:
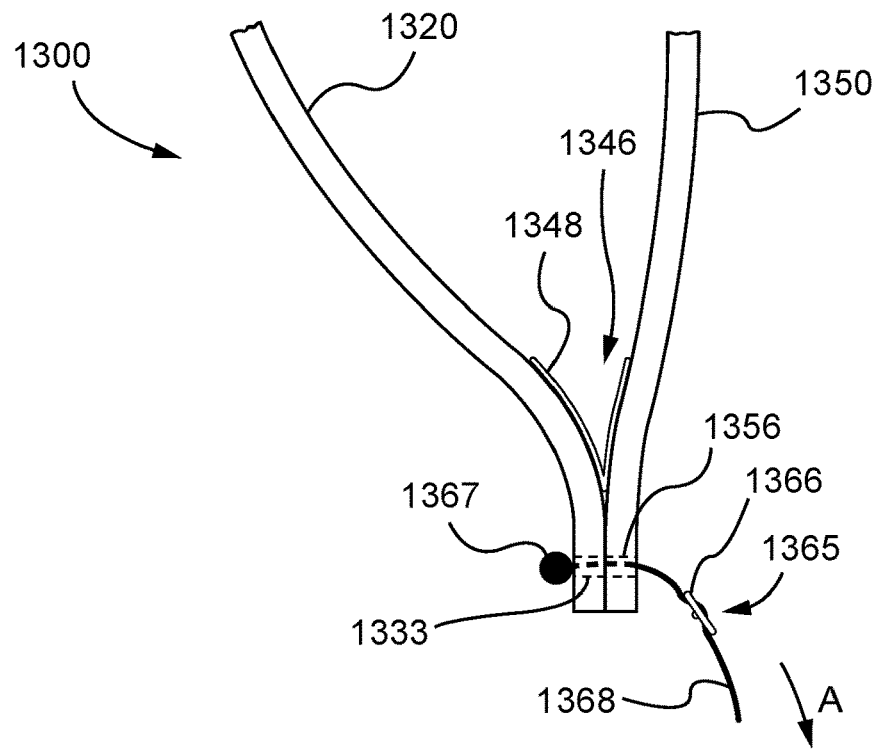
FIG. 39 is a side view of a portion of a prosthetic heart valve, showing a coupling portion that includes a movable joint and tether mechanism, according to an embodiment.

FIG. 39 illustrates a portion of an outer frame 1320 and a portion of an inner frame 1350 of a prosthetic heart valve 1300, according to another embodiment. The outer frame 1320 is coupled to the inner frame 1350 via coupling joints 1346. In this embodiment, the coupling joint 1346 includes a hinge member 1348 and a tether assembly 1365 as described in more detail below.

The hinge member 1348 can be the same as or similar to the hinge member 648 described above for valve 600. The hinge member 1348 can be flexible to allow the outer frame 1320 to move relative to the inner frame 1350 between the first configuration and the second inverted configuration. In some embodiments, the hinge member 1348 can limit the plane of motion of the outer frame 1320 with respect to the inner frame 1350. The hinge member 1348 can function, for example, as a living hinge.

As shown in FIG. 39, the tether assembly includes a tether 1368, a stop member 1367 and an optional clip 1366. The tether 1368 can be received through a through-hole 1356 defined by the inner frame 1350 and a through-hole 1333 defined by the outer frame 1320. Similar to as described above with respect to the suture 753 for valve 700 (FIG. 33A), the stop member 1367 can be disposed on an end of the tether 1368 and the clip 1368 can be slidably coupled to the tether 1368. The stop member 1367 can be for example, a knot formed on the end of the tether 1368, or any other suitable stop member with a size/diameter larger than the through-holes, 1356 and 1333. The clip 1366 can be configured to be slidable along the tether 1368, yet have sufficient friction to maintain a desired position along the tether 1368. In some cases, a clip 1366 may not be desired. For example, when the clip 1366 is disposed toward the apex side of the valve, as shown in FIG. 39, unidirectional forces on the tether 1368 can be sufficient to maintain the stop member 1367 against the outer side portion of the outer frame 1320. Thus, the clip member 1366 can optionally be excluded.

The tether 1368 can be, for example, a flexible member similar to the tether 290 described above for valve 200. The tether 1368 can be formed with any suitable material such as, for example, a braided string/thread. The stop member 1367 is configured to be disposed outside the through-hole 1356 and the through-hole 1333, on an outer side of the outer frame 1320. The clip 1366 is disposed on an outer side of the inner frame 1350 and can be configured to be slidable along the tether 1368, yet have sufficient friction to maintain its position along the tether 1368. Thus, the inner frame 1350 and the outer frame 1320 can be disposed between the stop member 1367 and the clip 1366.

In use, the tether 1368 can be pulled in a direction of arrow A such that the stop member 1367 is pulled against the outer side of the outer frame 1320, and the clip 1366 can be slid up against the outer side of the inner frame 1350. Thus, although the hinge member 1348 can couple the inner frame 1350 to the outer frame 1320 in a similar manner as described for valve 600, the tether 1368 can be used to provide further securement without interfering with the ability of the outer frame 1320 to rotate or pivot about the hinge member 1348. In addition, the tether 1368 can be used in place of the proximal struts of the valve 1300 (see, e.g., struts 243A in FIGS. 6 and 8).

In some embodiments, the tether assembly 1365 can be used alone to couple the inner frame 1350 to the outer frame 1320, without the hinge member 1348. In such an embodiment, as described for valve 700 with respect to FIGS. 33A and 33B, the outer frame 1320 and inner frame 1350 can be delivered prior to being securely coupled together. For example, the outer frame 1320 and the inner frame 1350 can be loosely coupled via the tether assembly 1365 and be loaded into a delivery sheath (not shown) with the outer frame inverted upon itself and disposed distal of the inner frame 1350. A distal end portion of the delivery sheath can be disposed within the left atrium and the outer frame 1320 can be moved outside of the delivery sheath and into the left atrium. Upon being moved outside of the delivery sheath, the outer frame 1320 can revert and assume a biased expanded configuration. The inner frame 1350 can be moved into a nested position within the outer frame 1320 and the tether 1368 can be pulled such that the stop member 1367 is pulled against the outer side of the outer frame 1320 and the clip 1366 can be slid toward the outer side of the inner frame 1350 to secure the inner frame 1350 to the outer frame 1320.

Figure 40:
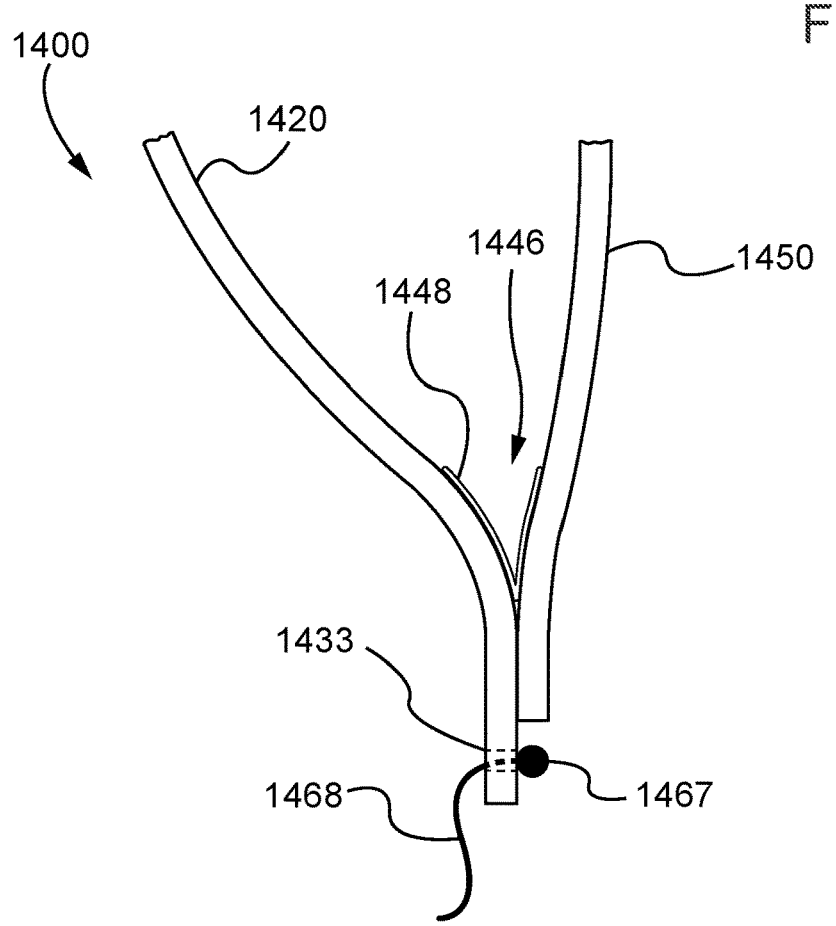
FIG. 40 is a side view of a portion of a prosthetic heart valve, showing a coupling portion that includes a movable joint and tether mechanism, according to another embodiment.

FIG. 40 illustrates a portion of an outer frame 1420 and a portion of an inner frame 1450 of a prosthetic heart valve 1400, according to some embodiments. In this embodiment, the outer frame 1420 is coupled to the inner frame 1450 via a coupling joint 1446 that includes a hinge member 1448 that can be the same as or similar to and function the same as or similar to the hinge member 648 of valve 600. The valve 1400 also includes a tether assembly 1465 that includes a tether 1468 and a stop member 1467. As shown in FIG. 40, in this embodiment, the tether 1468 is disposed through only a through-hole 1433 defined by the outer frame 1420. Thus, the tether assembly 1468 in this embodiment serves only to replace the proximal struts of the valve 1400.

FIGS. 41A-41K illustrate a portion of a prosthetic heart valve 1500, according to an embodiment. The prosthetic heart valve 1500 (also referred to as "prosthetic valve" or "valve") includes an inner frame assembly 1540 having an inner frame 1550, and an outer frame assembly 1510 having an outer frame 1520 (see FIGS. 41G-41I). The outer frame 1520 is coupled to the inner frame 1550 via a coupling joint 1546 (see FIGS. 41G-41I). In this embodiment, the coupling joint 1546 includes sutures wound about the inner frame 1550 and the outer frame 1520 as described in more detail below.

Figure 42A:
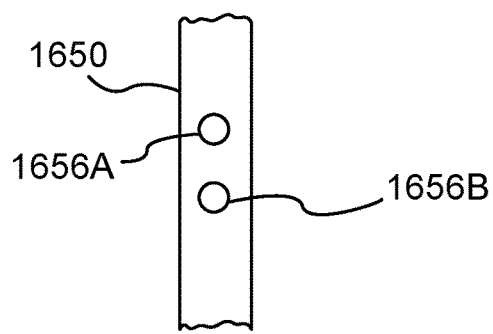
FIG. 42A is a front view of a portion of an inner frame of a prosthetic heart valve, according to another embodiment.
Figure 42B:
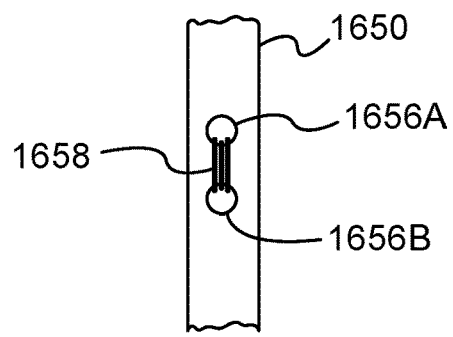
FIGS. 42B and 42C area a front view and a side view, respectively, of the portion of the inner frame of FIG. 42A shown with a suture coupled thereto.
Figure 42C:
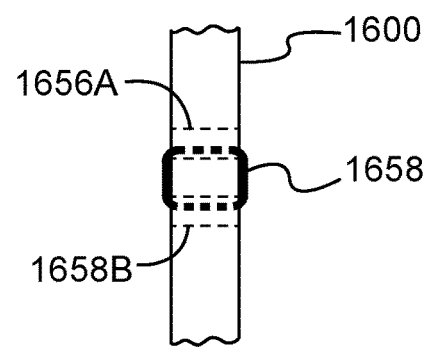

As shown in FIGS. 41B and 41C, which are detail side and front views, respectively, of encircled area A in FIG. 41A, frame portions of the inner frame 1550 define a pair of openings 1556A and 1556B. Each of the through-holes 1556A, 1556B is generally in a half-circle shape, although other shapes are within the scope of the disclosure. For example, FIGS. 42A-42C illustrate an example embodiment of an inner frame 1650 having through-holes 1656A, 1656B that are generally round. As shown in FIGS. 42B and 42C, a suture 1658 can be wound about the inner frame 1650 through through-holes 1656A and 1656B in a similar manner as described below for valve 1500.

Figure 41D:
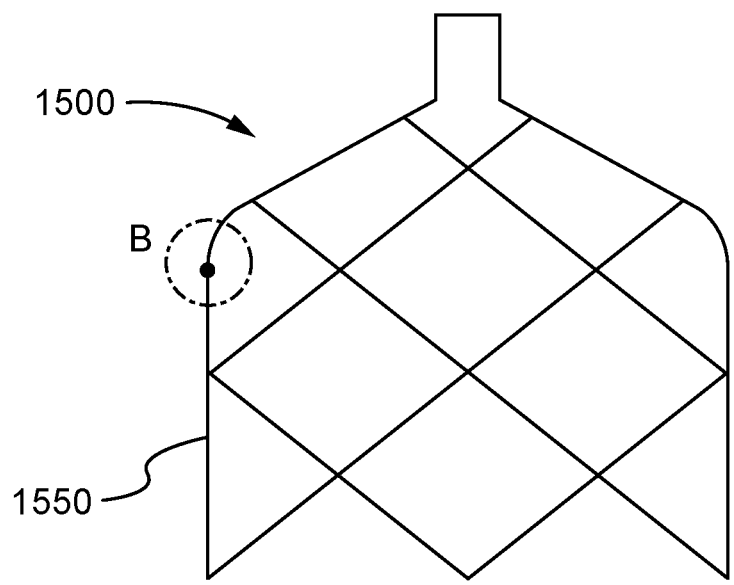
FIG. 41D is a side view of the inner frame of the prosthetic heart valve of FIG. 41A.
Figure 41E:
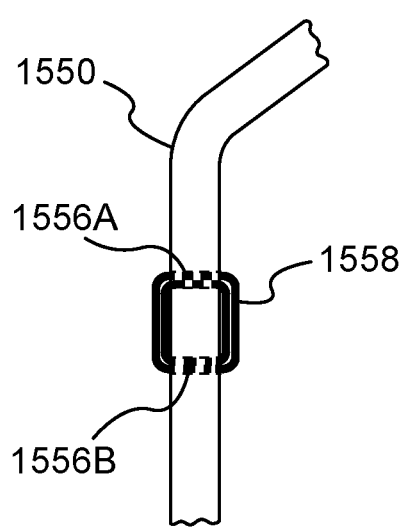
FIGS. 41E and 41F are a side view and a front view, respectively, of encircled portion B in FIG. 41D, illustrating a portion of suture attached to the inner frame.
Figure 41F:
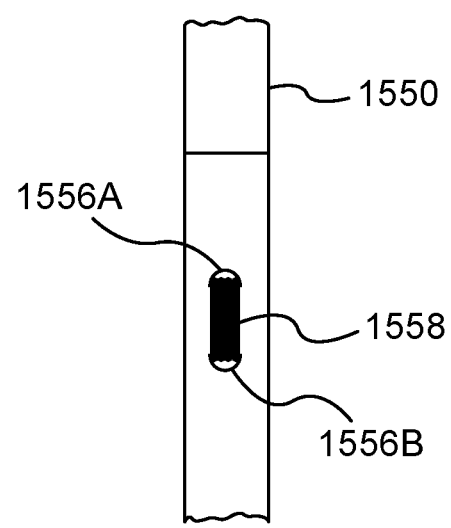

As shown in FIGS. 41E and 41F, a portion of suture 1558 is wound through the through-holes 1556A, 1556B and around a portion of the inner frame 1550 disposed between the through-holes 1556A, 1556B. The half-circle shape of the through-holes 1556A, 1556B provides a relatively flat surface such that when the suture 1558 is wound about the portion of the inner frame 1550, a relatively flat platform is provided for interfacing with additional sutures used to attach the outer frame 1550 to the inner frame 1550 (see FIGS. 40G-40I, described in detail later).

Figure 41G:
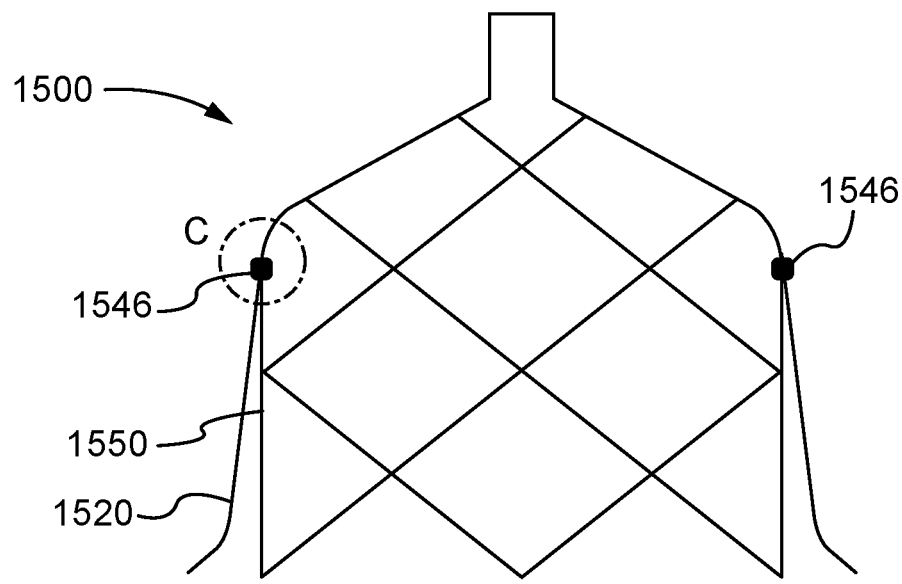
FIG. 41G is a side view of the inner frame of FIG. 41A coupled to an outer frame of the prosthetic heart valve.
Figures 41H, 41I:
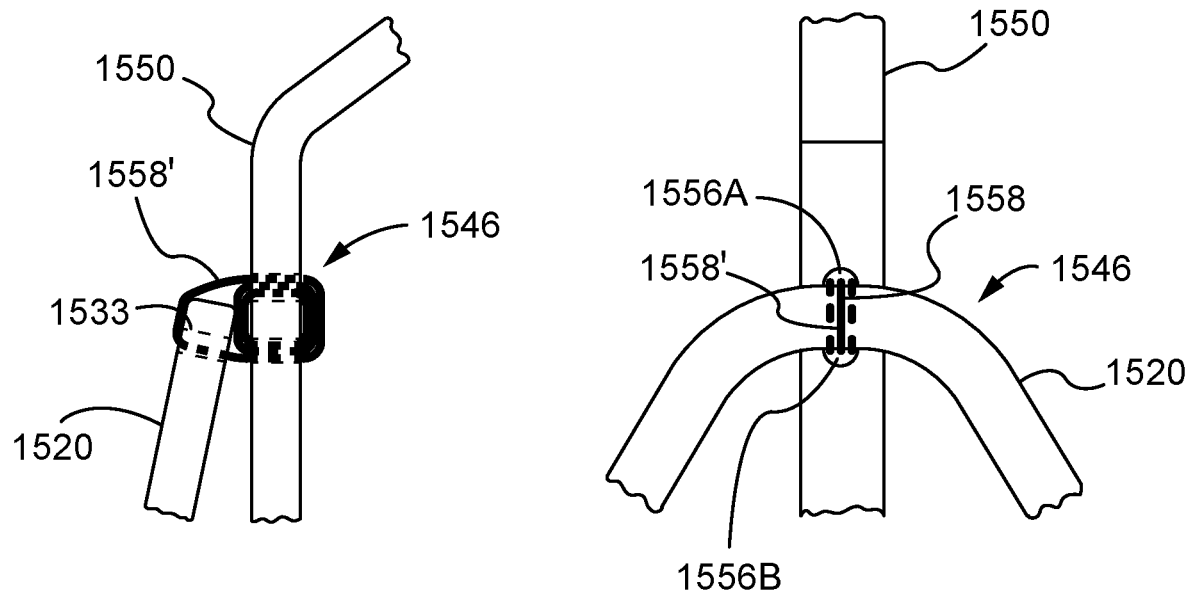
FIGS. 41H and 41I are a side view and a front view, respectively, of encircled portion C in FIG. 41G, illustrating a portion of suture coupling the outer frame to the inner frame.

Referring to FIGS. 41G-41I, which illustrate the outer frame 1520 coupled to the inner frame 1550, the frame members of the outer frame 1520 define a through-hole 1533 through which a second suture 1558' is received. More specifically, the second suture 1558' is wound through the through-hole 1533, around an end of the outer frame 1520 and then wound through the through-holes 1556A and 1556B of the inner frame 1550, as best shown in FIG. 41H. The second suture 1558' can be wound to form multiple layers of windings that run through the through the 1533, and the through-holes 1556A, 1556B. Thus the suture 1558' is disposed over portions of the suture 1558 that is wound about the inner frame 1550 within the through-holes 1556A, 1556B, providing frictional, non-sliding contact. The end portion of the outer frame 1520 abuts the portion of the suture 1558 disposed on an exterior surface of the inner frame 1550 as shown in FIG. 41H. In this manner, the suture 1558 prevents abrasive contact between the outer frame 1520 and the inner frame 1550, while permitting the outer frame 1520 to move (e.g., pivot, rotate) between the first configuration and the second inverted configuration relative to the inner frame 1550. The suture 1558 and/or the suture 1558' can independently be made of any suitable material including, but not limited to, nylon, polyester, polyvinylidene fluoride (PVDF), polypropylene, combinations thereof, and/or the like.

Figure 43:
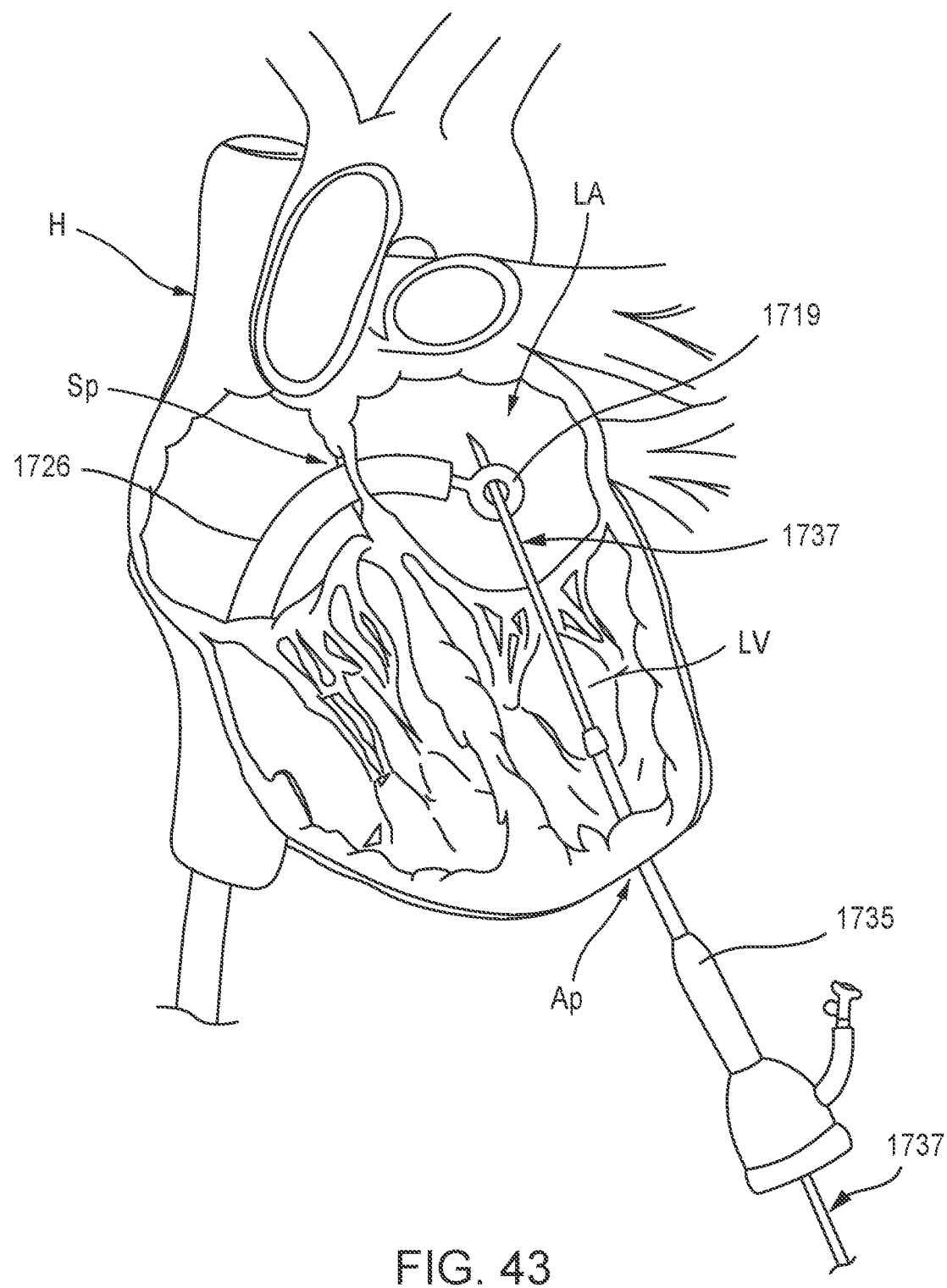
FIGS. 43-48 are each a cross-sectional illustration of a heart with devices used during various stages in a procedure to transfemorally deliver and deploy a prosthetic mitral valve.
Figure 44:
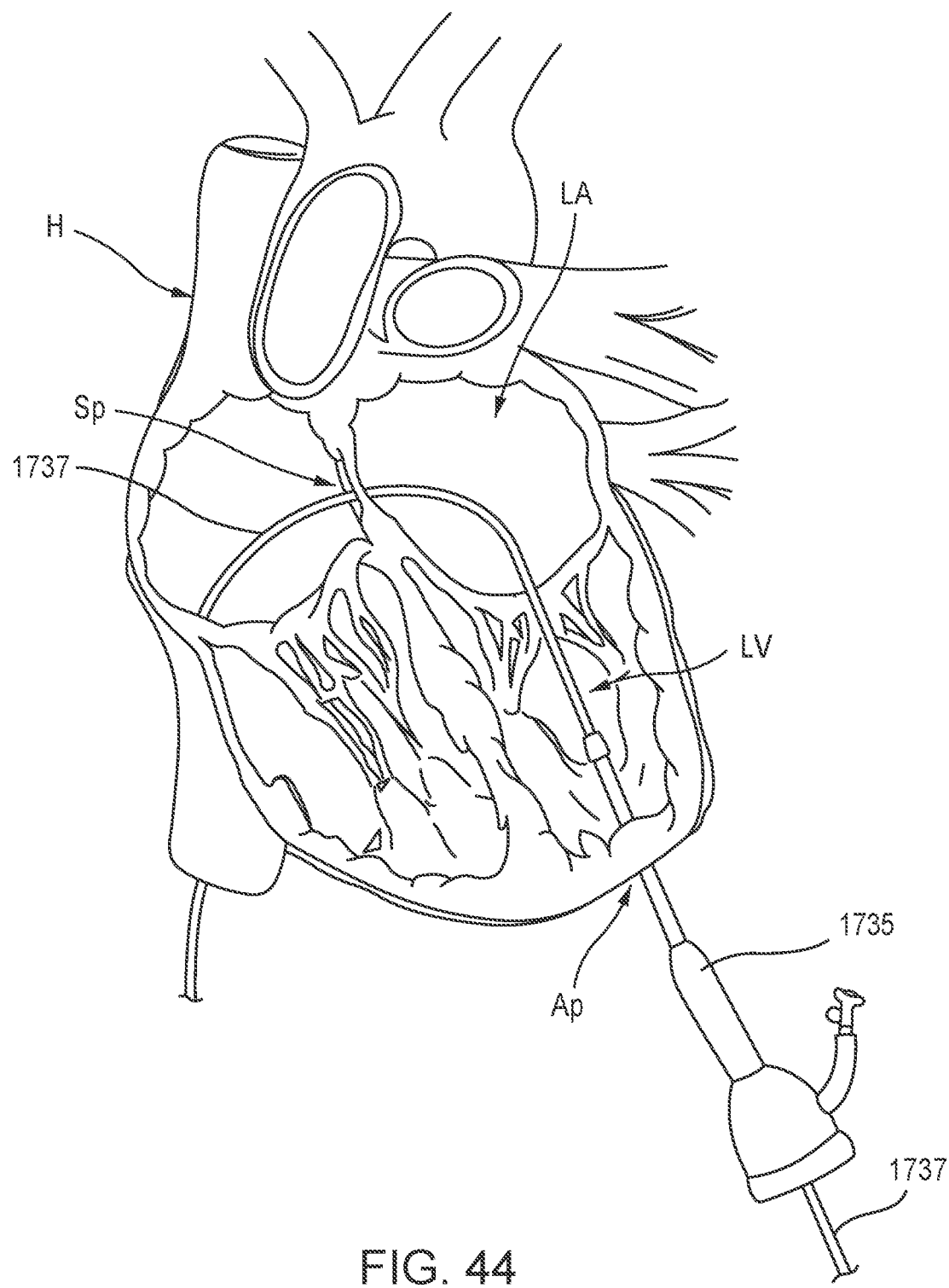

FIGS. 43-48 illustrate an alternative method of delivering a prosthetic valve within an annulus of a heart via a transfemoral delivery approach. As shown in FIG. 43, a procedural catheter 1735 is inserted through an apical puncture (e.g., a 5F apical puncture) in a ventricular wall at the apex Ap of the heart H. A guide wire 1737 is inserted through a lumen (not shown) of the procedural catheter 1735 and extended through the left ventricle LV, through a mitral valve gap and into the left atrium LA. A delivery sheath 1726 is introduced through a femoral vein puncture and extended through the inferior vena cava, into the right atrium, and then through a transseptal puncture of the septum Sp of the heart H, and into the left atrium LA of the heart H. A snare device 1719 is movably disposed within the delivery sheath 1726 and used to grab or snare a distal end portion of the guide wire 1737, as shown in FIG. 43. The snare device 1719 can be used to pull the guide wire 1737 through the delivery sheath 1726 such that the distal end portion of the guide wire 1737 extends outside the femoral vein and a proximal end of the guide wire 1737 is disposed through the ventricular wall at the apex Ap of the heart H, as shown in FIG. 44. Although not shown in FIGS. 43 and 44, the procedural catheter 1735 is disposed outside the patient's body, the distal end of the guide wire 1737 extends outside the femoral vein and outside the patient's body, and the proximal end of the guide wire 1737 extends outside the apex Ap and outside the patient's body. Although the above described snare process describes delivering the guide wire 1737 to the left atrium of the heart and then snaring the guide wire 1737 using the snare device 1719, in alternative embodiments, the guide wire 1737 can be delivered to the left ventricle LV and the snare device 1719 and delivery sheath 1726 can be inserted through the mitral annulus and into the left ventricle LV to grab or snare the guide wire 1737 as described above.

Figure 45:
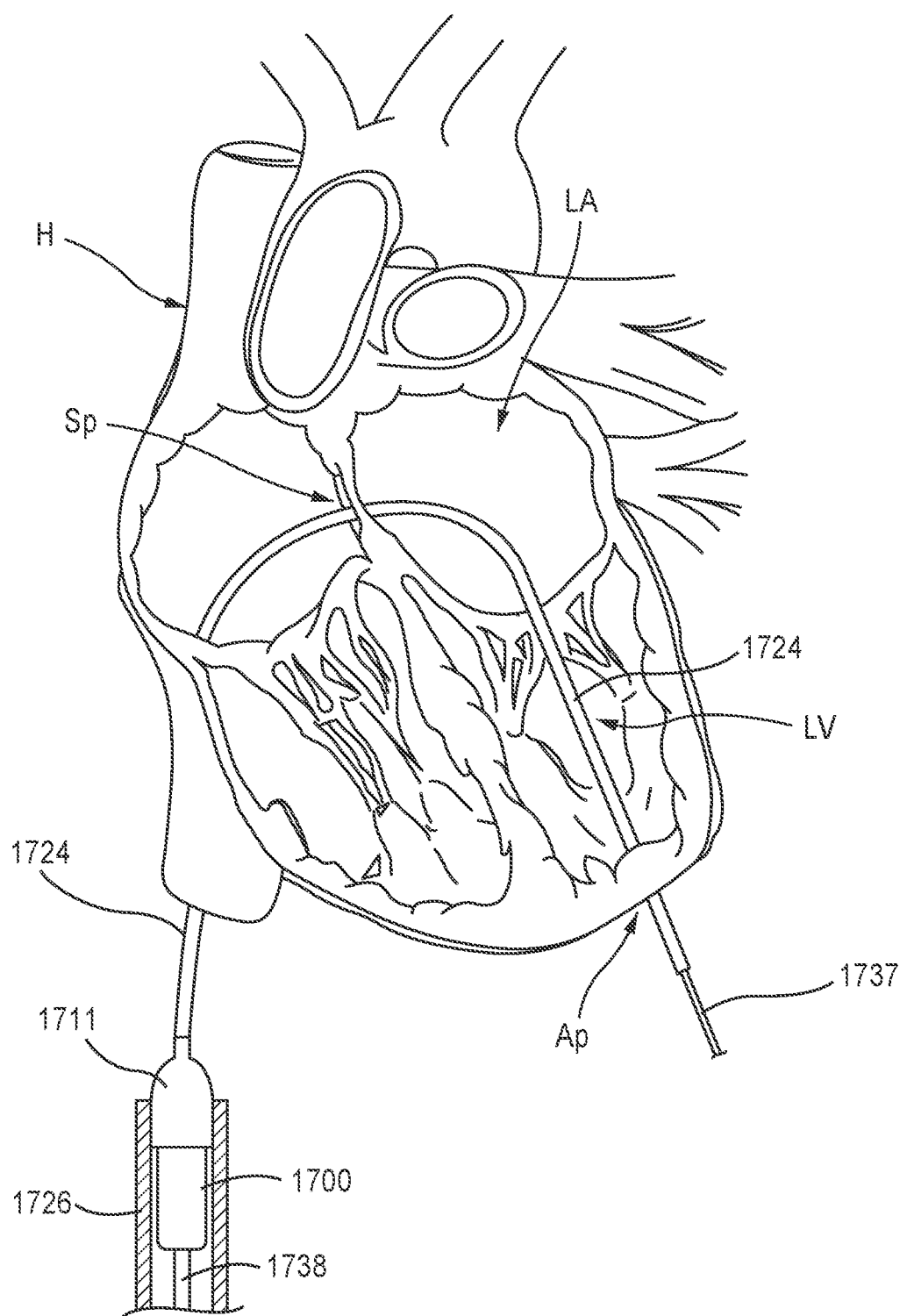

After the guide wire 1737 has been extended between the apex Ap and the access site to the femoral vein, the delivery sheath 1726 can be removed. A leader tube 1724 is loaded over the guide wire 1737 starting outside the heart (and outside the procedural catheter 1735) and exiting the femoral vein at the femoral puncture site as shown in FIG. 45. As shown in FIG. 45, the leader tube 1724 includes a balloon dilator member 1711 that is inserted into a distal end of the delivery sheath 1726 and disposed partially over a distal end portion of the prosthetic valve 1700. For example, the balloon dilator member 1711 can have a collapsed or uninflated configuration (not shown) for delivery over the guide wire 1737 and can then be inflated or otherwise moved to an expanded configuration as shown in FIG. 45. Also shown in FIG. 45, a pusher 1738 is disposed within the lumen of the delivery sheath 1726 and can be used to move or push the prosthetic valve 1700 into the left atrium LA, as described in more detail below. With the leader tube 1724 disposed between the femoral puncture site and the apex of the heart, the guide wire 1737 can be removed. Although not shown in FIGS. 45-47, the procedural catheter 1735 remains inserted into the left ventricle LV of the heart as shown in FIGS. 43 and 44.

The prosthetic valve 1700 can be configured the same as or similar to the prosthetic valves described herein. The prosthetic valve 1700 (shown schematically within the delivery sheath 1726 in FIG. 45) can be disposed in an inverted configuration within the delivery sheath 1726 to reduce the overall outer perimeter of the prosthetic valve 1700. A tether 1736 is coupled to a distal end portion of the prosthetic valve 1700 (see FIGS. 47 and 48). The tether 1736 can be threaded through the leader tube 1724 prior to the leader tube 1724 being disposed within the distal end of the delivery sheath 1726. For example, as previously described, the tether 1736 can include a valve leader member (not shown). The valve leader member can have a tapered distal end to aid in the insertion and maneuvering of the valve leader member through the leader tube 1724. The valve leader member can be attached at a proximal end portion of the tether 1736, which is attached to the valve 1700. The tether 1736 can be formed, for example, as a braided rope or cord. The tether 1736 can be threaded through the leader tube 1724 with the valve leader member extended out the apex of the proximal end of the leader tube 1724 outside the apex of the heart. Thus, the tether 1736 extends between the apex Ap and the femoral puncture site where it is coupled to the valve 1700.

Figure 46:
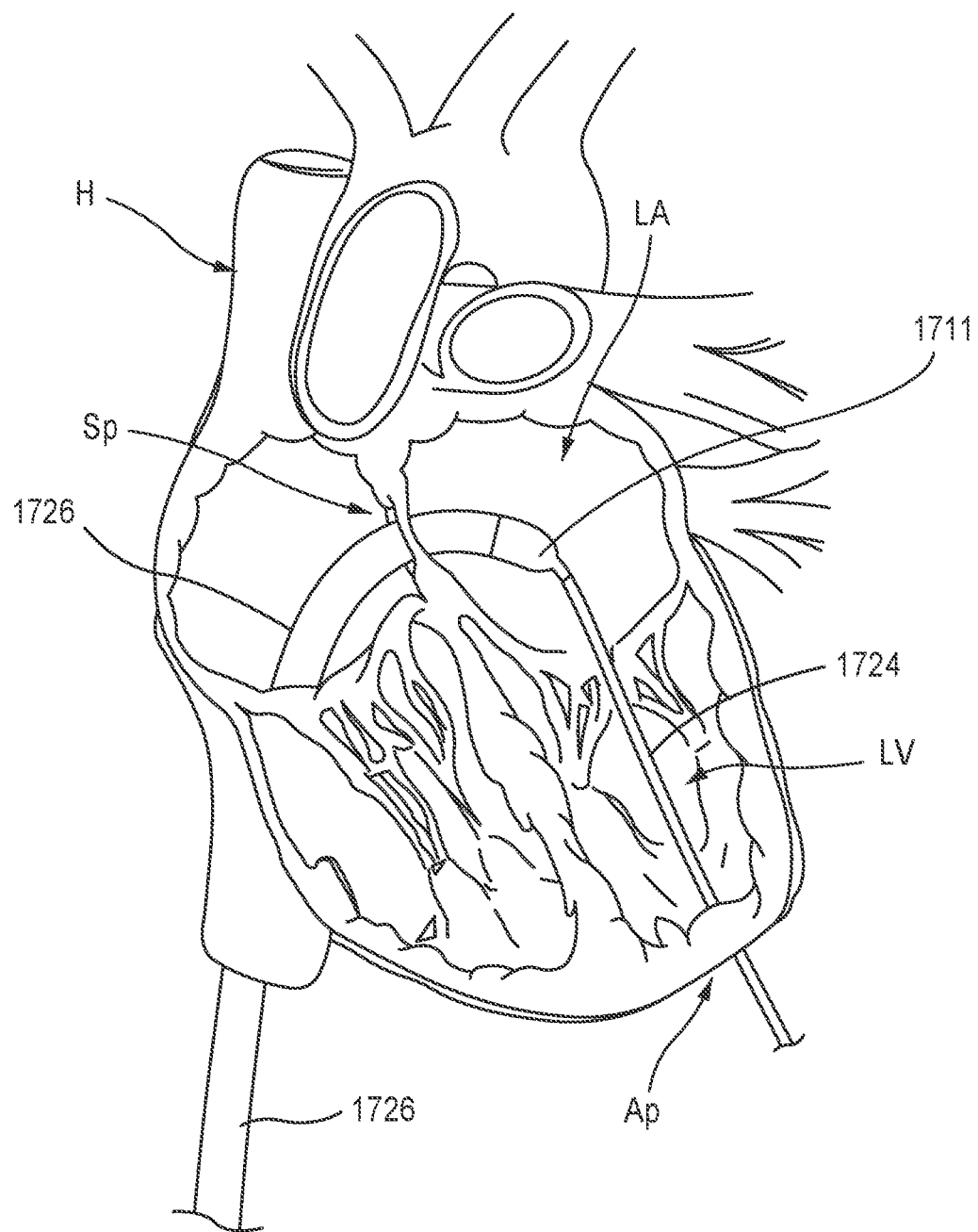

The delivery sheath 1726 can then be inserted through the femoral puncture site and moved through the femoral vein, through the inferior vena cava, into the right atrium, and then through the septum Sp until a distal end portion of the delivery sheath 1726 (with the valve 1700) is disposed within the left atrium LA, as shown in FIG. 46. The dilator balloon member 1711 can provide a smooth lead-in to assist in maneuvering the distal end of the delivery sheath 1726 through the femoral vein and within the heart. Although the delivery sheath 1726 is used to deliver both the snare device 1719 and the valve 1700, in other embodiments, a different delivery sheath can be used to deliver the snare device 1719 than is used to deliver the valve 1700.

Figure 47:
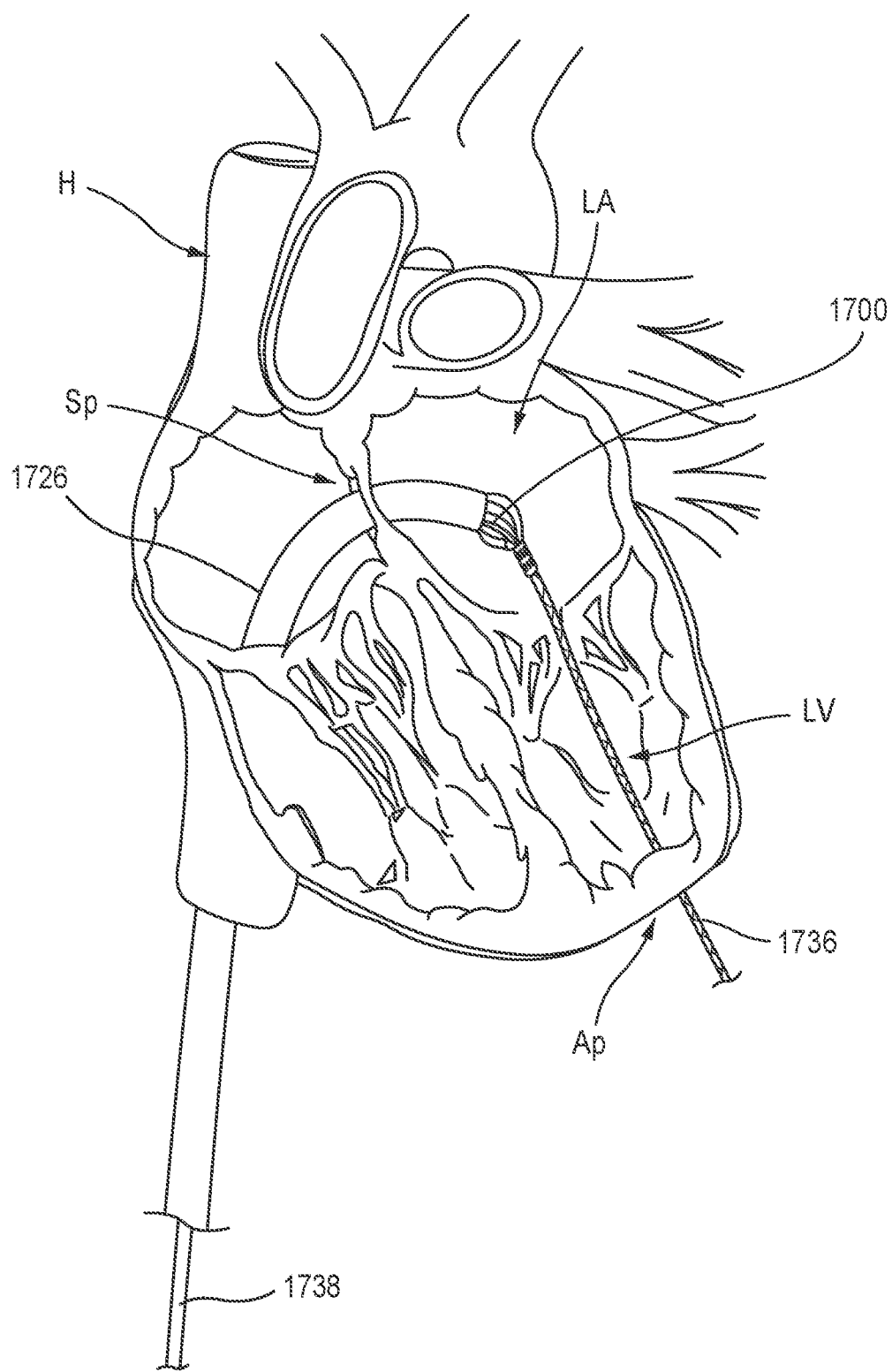

With the distal end of the delivery sheath 1726 within the left atrium LA, the leader tube 1724 can be removed through the apex Ap, leaving the tether 1736 extended between the valve 1700 and outside the apex Ap of the heart (see FIG. 47). For example, the balloon dilator member 1711 can be moved back to a collapsed configuration for removal through the procedural catheter 1735. The procedural catheter 1735 can then also be removed. The pusher 1738 can be used to push or move the valve 1700 out the distal end of the delivery sheath 1726 and within the left atrium LA of the heart as shown in FIG. 47. As the valve exits the distal end of the delivery sheath 1726 the valve 1700 can revert and return to its original undeformed shape as described above, for example, for valve 200. For example, the valve 1700 can be formed with a shape-memory material and can have a biased undeformed shape and can be manipulated and/or deformed (e.g., compressed and/or expanded) and, when released, return to its original undeformed shape. The valve can be, for example, a valve constructed the same as or similar to, and function in the same or similar manner as, the prosthetic heart valve 200, described above.

As shown in FIG. 47, the tether 1736 extends from the valve 1700 through the apical puncture and outside the patient's body. As the delivery sheath 2026 is advanced, the tether 1736 can optionally be pulled at the apex end to help move the delivery sheath 1726, with the valve 200 disposed therein, through the femoral vein, through the septal puncture and into the left atrium LA. The valve 1700 can then be fully deployed within the left atrium LA, as shown in FIG. 48, by using the pusher 1738 described above and/or by pulling the apex end portion of the tether 1736 until the valve 1700 is pulled out of the lumen of the delivery sheath 1726 and disposed within the left atrium LA.

In some embodiments, the pusher 1738 can also be used to aid in positioning the valve 1700 in a desired radial orientation within the left atrium LA. For example, the pusher device 1738 can define an internal lumen (not shown) that can be placed over an inner frame portion of the valve 1700 to hold the inner frame portion in a small diameter, which can help enable the valve 1700 to be positioned in a desired radial orientation and be seated within the annulus of the mitral valve. Further examples of such a valve assist device are described below with reference to FIGS. 49-51.

Figure 48:
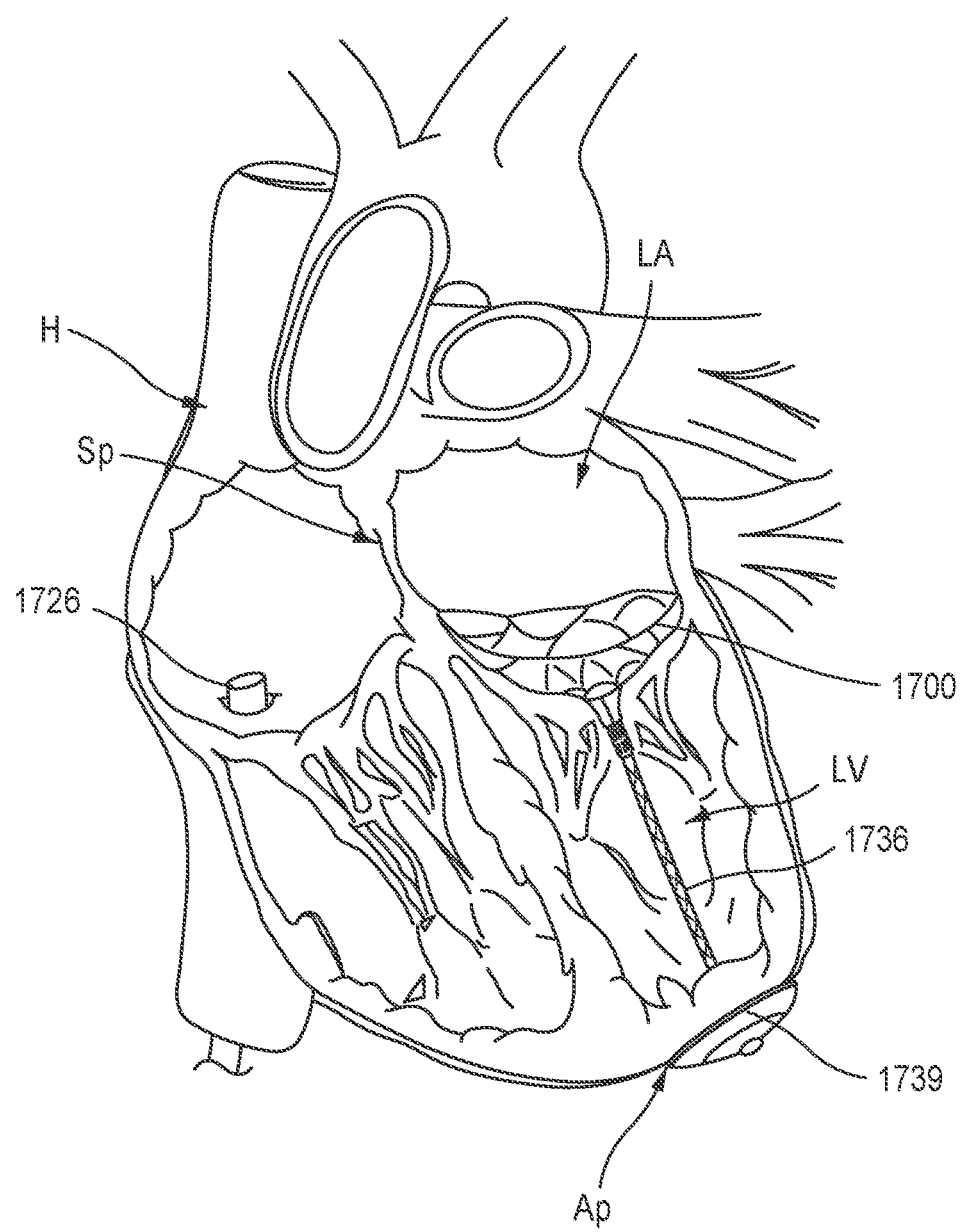

As shown in FIG. 48, as the valve 1700 is deployed within the left atrium LA, the valve 1700 is allowed to assume its biased expanded or deployed configuration. The delivery sheath 1726 can then be removed from the patient and the valve 1700 can be positioned and tensioned using the tether

1736 to obtain the desired or optimal location in the native mitral annulus and minimize perivalvular leaks. An epicardial pad device 1739 (as described above) can be used to secure the tether 1736 and valve 1700 in position within the mitral annulus. In some embodiments, rather than securing the prosthetic mitral valve with a tether and epicardial pad, the prosthetic mitral valve can be secured with clips or other coupling methods to a portion(s) of the mitral valve apparatus and/or the ventricular wall of the heart.

Figure 49:
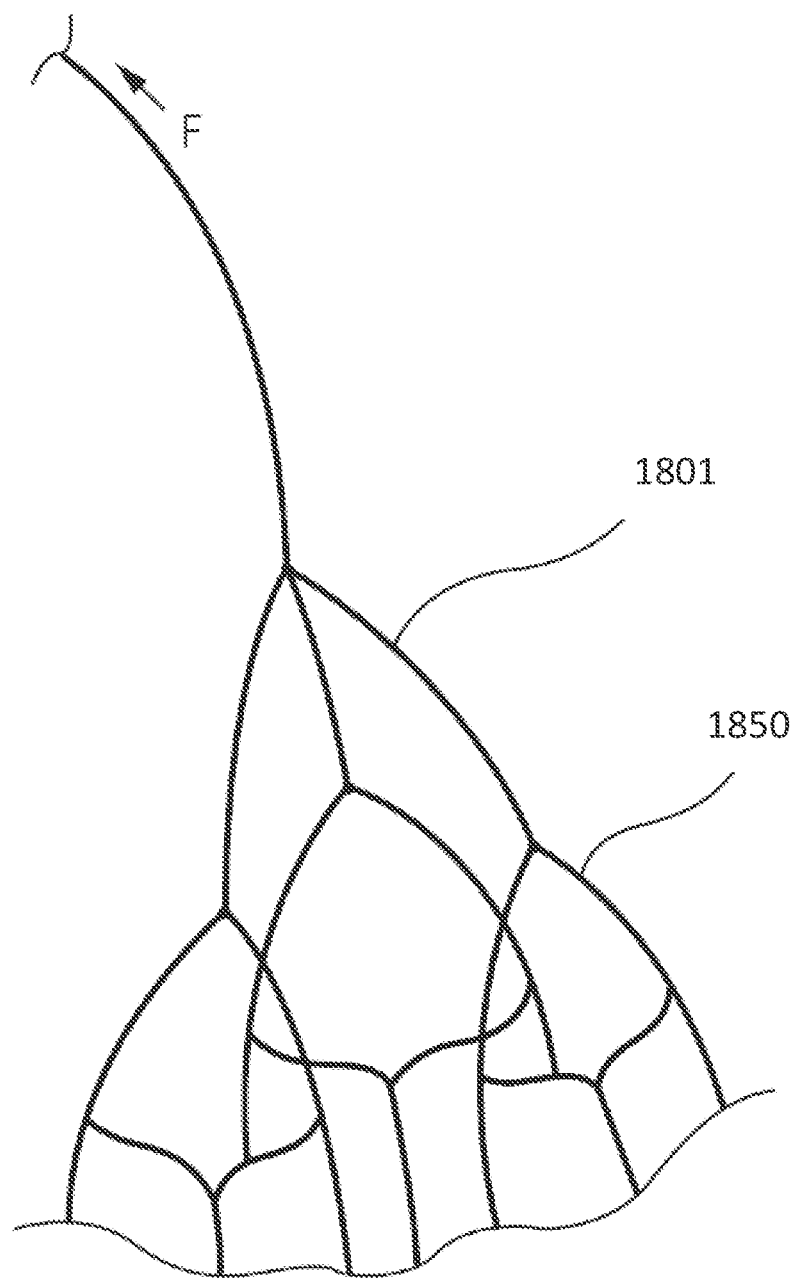
FIG. 49 is a cross-sectional illustration of a heart with a portion of a delivery sheath shown after deploying a prosthetic mitral valve with the assistance of a wire assist structure, according to an embodiment.
Figure 50:
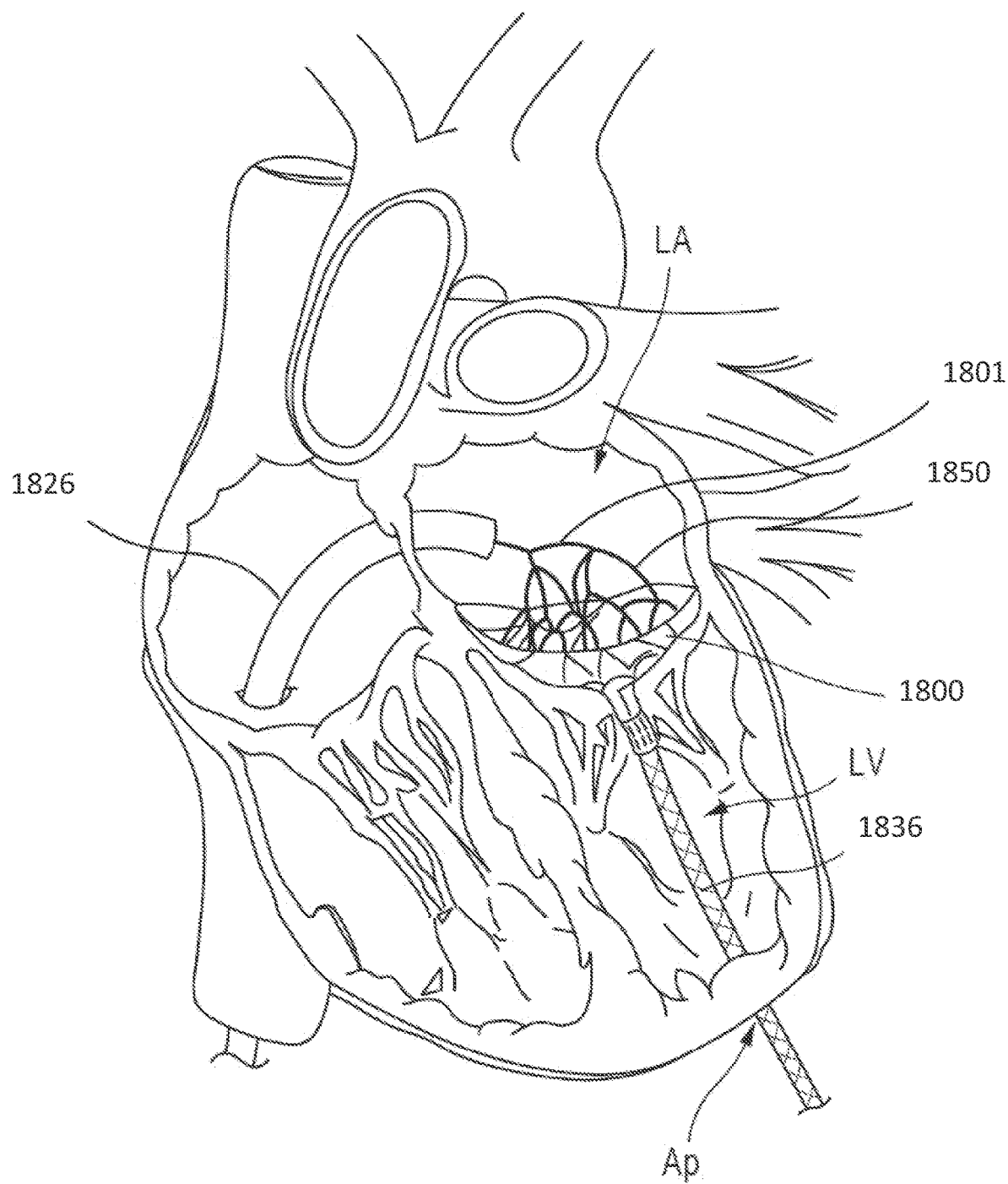
FIG. 50 is a perspective view of the wire assist structure of FIG. 49 coupled to a portion of a prosthetic mitral valve, according to an embodiment.

FIGS. 49 and 50 illustrate an optional wire assist structure that can be used during a procedure to deliver a prosthetic heart valve, for example, transfemorally as described above for previous embodiments. A wire assist structure 1801 can be releasably coupled to a valve 1800 as shown in FIG. 49. The valve 1800 can be constructed the same as or similar to, and function the same as or similar to, the valves described above for previous embodiments. For example, the valve 1800 can include an outer frame 1820 and an inner frame 1850. The wire assist structure 1801 can be releasably coupled to the inner frame 1850 as shown in FIGS. 49 and 50. For example, releasable connectors (not shown) can be used to couple the wire assist structure 1801 to the inner frame 1850.

In use, the wire assist structure 1801 can be movably disposed within a delivery sheath 1826 used to deliver the valve 1800 to the heart. The wire assist structure 1801 can hold the inner frame 1850 and provide positioning control of the valve 1800 (i.e., clocking and advancement) while the outer frame 1850 of the valve 1800 is fully expanded, which allows the valve 1800 to be functioning during the positioning phase. When the valve 1800 is in the desired final position, the wire assist structure 1801 can be released from the inner frame 1850 and removed with the delivery sheath 1826.

Figure 51:
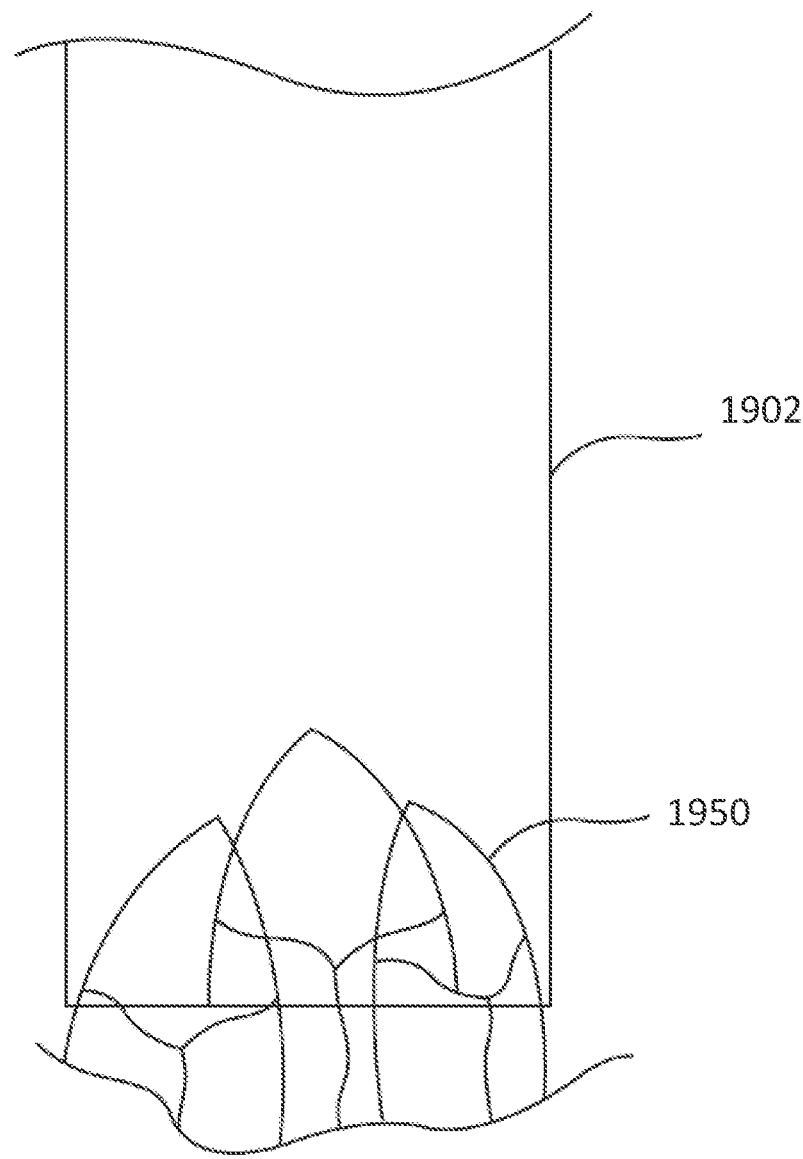
FIG. 51 is a perspective view of an assist member according to another embodiment and coupled to a portion of a prosthetic mitral valve, according to an embodiment.

FIG. 51 illustrates another optional assist member that can be used during a procedure to deliver a prosthetic heart valve transfemorally. An assist member 1902 can be in the form of a tubular member defining a lumen with a diameter sized to receive at least a portion of the inner frame 1950 of a valve 1900. The valve 1900 can be constructed the same as or similar to, and function the same as or similar to, the valves described above for previous embodiments. For example, the valve 1900 can include an outer frame (not shown) and the inner frame 1950 as described above for previous embodiments.

In use, the assist member 1902 can be movably disposed within a delivery sheath (not shown) used to deliver the valve 1900 and be disposed over at least a portion of the inner valve assembly (e.g., inner frame 1950). As with the wire assist structure 1801, the assist member 1902 can hold the inner frame 1950 in a small compact configuration and allow for positioning control of the valve 1900 (i.e., clocking and advancement) while the outer frame of the valve 1900 is being expanded. This can in some cases allow the valve 1900 to be functioning (or at least partially functioning) during the positioning phase of the valve 1900. With the inner frame 1950 held in a compact or small diameter form factor, the valve 1900 can be more easily positioned to help seal the annulus with the outer frame (not shown) of the valve 1900. When the valve 1900 is in the desired final position, the assist member 1902 can be removed.

Figure 52:
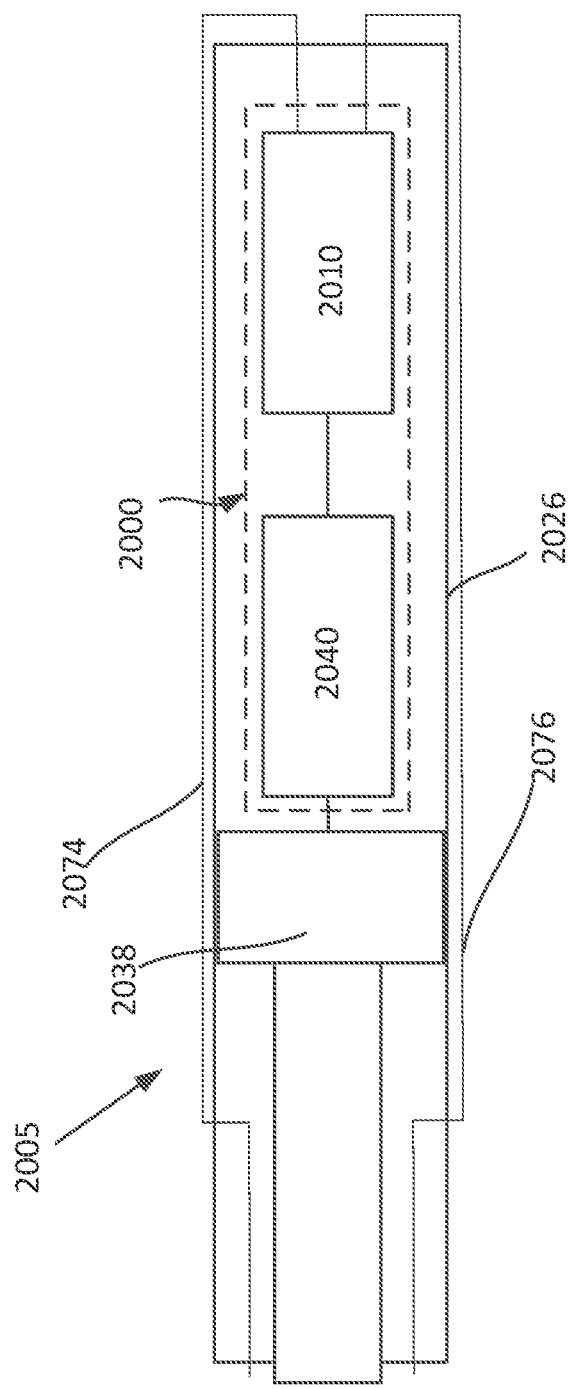
FIG. 52 is a schematic illustration of a delivery device and prosthetic heart valve, according to an embodiment.

FIG. 52 is a schematic illustration of delivery system that can be used to deliver and deploy a prosthetic heart valve within a heart of patient with, for example, a transvascular approach. In this embodiment, a delivery system 2005 includes a delivery sheath 2026, a valve holder 2038 (also referred to as a "pusher"), and one or more actuation wires 2074 and 2076. In this schematic illustration, only two actuation wires are illustrated, but in other embodiments, only one actuation wire or more than two actuation wires can be used.

The delivery sheath 2026 can be used to deliver a valve 2000 that includes an inner valve assembly 2040 including an inner frame (not labeled in FIG. 52) and an outer valve assembly 2010 including an outer frame (not labeled in FIG. 52). The valve 2000 can be constructed the same as or similar to, and function the same as or similar to, for example, the prosthetic valves described herein (e.g., valves 100, 200, 300, 400, etc.) and can be moved between a deployed or expanded configuration and a delivery configuration in which the outer frame is disposed in an inverted position relative to the inner frame as described above. As shown in FIG. 52, the valve 2000 can be disposed within a lumen of the delivery sheath 2026 when the valve is in the delivery configuration (i.e., the outer frame is inverted relative to the inner frame). The valve holder 2038 is coupled to the inner valve assembly 2040 and the actuation wires are coupled to the outer fame assembly 2010. The valve holder 2038 can be releasably coupled to the inner frame assembly 2040 with couplers, as described in more detail below with reference to FIGS. 53-58C.

The actuation wires 2074 and 2076 can be coupled to the outer fame of the outer valve assembly 2010 with a variety of different coupling methods. For example, the outer frame 2010 can include loops (as described in more detail below with reference to specific embodiments (see, e.g., FIG. 57)) through which the actuation wires 2074 and 2076 can be received or threaded. The number of loops on the outer frame can vary and the number of loops through which each actuation wire is connected can vary. For example, in some embodiments, the outer frame includes 12 loops and a first actuation wire is threaded through 6 of the loops and a second actuation wire is threaded through 6 of the loops. In other embodiments, the outer frame can include 12 loops and there can be 4 actuation wires, each coupled to 3 of the loops. In some embodiments, a single actuation wire is coupled through all of the loops of the outer frame.

The delivery sheath 2026 can be used to deliver the valve 2000 to the left atrium of the heart as described above for previous embodiments. When the distal end of the delivery sheath 2026 is disposed within the left atrium, the valve 2000 is moved out of the lumen of the delivery sheath 2026 using the actuation wires 2074, 2076 to assist in pulling the valve 2000 out of the delivery sheath 2026. In some case, the valve holder 2038 can also be used to push the valve 2000 out of the delivery sheath 2026. More specifically, the actuation wires 2074 and 2076 can extend from the outer valve assembly 2010 out a distal end of the delivery sheath and extend proximally. In some embodiments, the actuation wires 2074, 2076 extend proximally outside the delivery sheath 2126, then pass back into the lumen of the delivery sheath 2026 through side apertures or holes (not shown) and then out a proximal end of the delivery sheath 2026. Thus, a user (e.g., physician) can pull the proximal end portions of the actuation wires 2074 and 2076 to in turn pull the outer frame assembly 2010 out of the distal end of the delivery sheath 2026. In some embodiments, the actuation wires 2074, 2076 extend proximally from the outer valve assembly 2010, back through the distal end of the delivery sheath 2026 and within the lumen of the delivery sheath, and then out a proximal end of the delivery sheath 2026. Various different embodiments and configurations are described in more detail below.

As the outer frame assembly 2010 exits the delivery sheath 2026 it will still be in an inverted configuration relative to the inner frame assembly 2040. After the outer frame assembly 2010 is at least partially outside of the lumen of the delivery sheath 2026, the outer frame assembly 2010 can begin to revert to its expanded or deployed configuration (not shown in FIG. 52). In this embodiment, however, the actuation wires 2074 and 2076 can function to selectively (e.g., by an operator) assist and/or control the expansion, deployment and/or articulation of the valve 2000 as the valve 2000 is delivered to the heart. In this manner, in use, the proximal end portions of the actuation wires 2074, 2076 can be pulled distally to manipulate the outer frame assembly 2010 to assist and control the transition of the outer frame assembly 2010 from its inverted configuration relative to the inner frame assembly 2040 to its expanded or deployed configuration (not shown). In some embodiments, the actuation wires 2074, 2076 can be manually grasped by a user to pull the actuation wires proximally. In some embodiments, the actuation wires 2074, 2076 can be operatively coupled to the delivery system 2005 such that the user does not have to manually handle the actuation wires. For example, the actuation wires can be coupled to a delivery sheath and/or to a handle assembly (not shown) of the delivery system 2005. Various embodiments of a delivery system are described in more detail below.

FIGS. 53-56 illustrate a delivery system 2105 and method for delivering and deploying a prosthetic heart valve 2100 into a heart. The prosthetic heart valve 2100 (also referred to herein as "valve") can be constructed the same as or similar to, and function the same as or similar to, any of the valves described herein. Thus, some details regarding the valve 2100 are not described herein.

Figure 53:
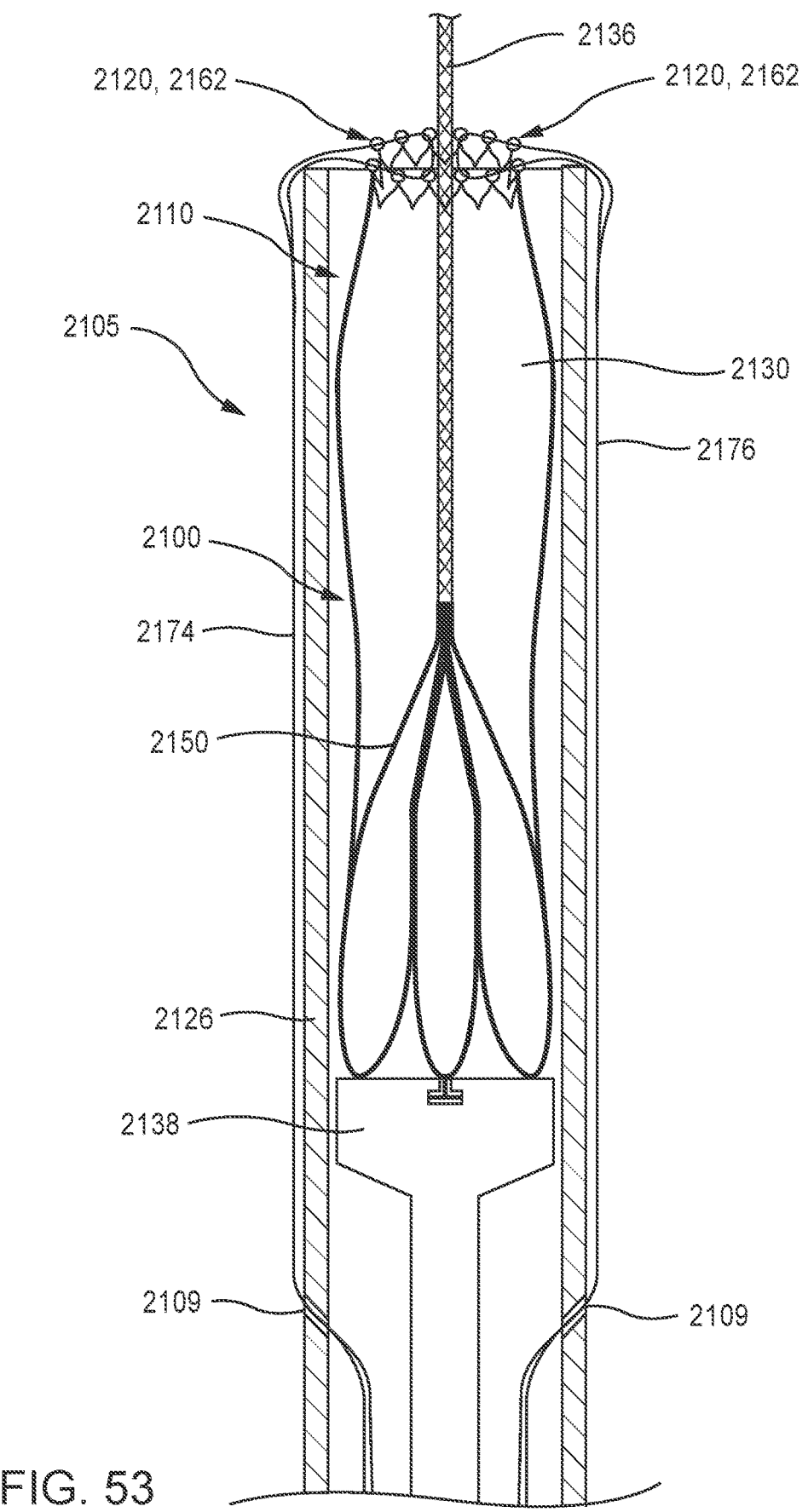
FIGS. 53-56 are progressional cross-sectional side views of a prosthetic valve being reconfigured and reoriented, and emerging from a lumen of a portion of a delivery sheath, according to an embodiment.

As shown in FIG. 53, the valve 2100 has an outer valve assembly 2110 with an outer frame 2120, an inner valve assembly 2140 with an inner frame 2150, and a tether 2136 coupled to the inner frame 2150. As described above for previous embodiments (e.g., valve 100, 200, 300 etc.), the outer frame 2120 and the inner frame 2150 of valve the 2100 can each be formed with a shape-memory material and have a biased, expanded or deployed configuration. The valve 2100 can also include an outer covering 2130. The outer frame 2120 and the inner frame 2150 can be moved to a collapsed or undeployed configuration for delivery of the valve 2100 to the heart in which the outer frame 2120 is in an inverted configuration relative to the inner frame 2150. In this example method of preparing the valve 2100 for delivery to the heart, the outer frame 2120 of the valve 2100 is first disposed in the prolapsed or inverted configuration as shown in FIG. 53. Specifically, the elastic or superelastic structure of outer frame 2120 of valve 2100 allows the outer frame 2120 to be disposed in the prolapsed or inverted configuration relative to the inner frame 2150.

To dispose the outer frame 2120 in its inverted configuration, the outer frame 2120 is folded or inverted distally such that the outer frame 2120 is pointed away from the inner frame 2150. With the outer frame 2120 in the inverted configuration, the valve 2100 can be placed within a lumen of a delivery sheath 2126 as shown in FIG. 53 for delivery of the valve 2100 to the left atrium of the heart. As discussed above, by disposing the outer frame 2120 of the valve 2100 in the inverted configuration, the valve 2100 can be collapsed into a smaller overall diameter, i.e., placed in a smaller diameter delivery sheath, than would be possible if the valve 2100 were collapsed radially when the inner frame 2150 and the outer frame 2120 are disposed concentric to one another. Said another way, when the two frames (i.e., the inner frame 2150 and the outer frame 2120) are concentric, the outer frame 2120 must be collapsed around the inner frame 2150, whereas in the inverted configuration, the two frames are coaxial but not concentric, such that the outer frame 2120 can be collapsed without needing to accommodate the inner frame 2150 nested inside it.

Figure 58B:
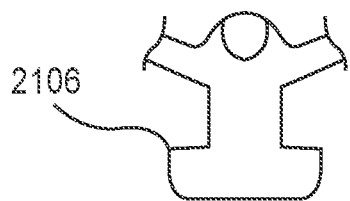
FIG. 58B is a side view of an attachment member of the prosthetic valve of FIG. 58A.
Figure 58A:
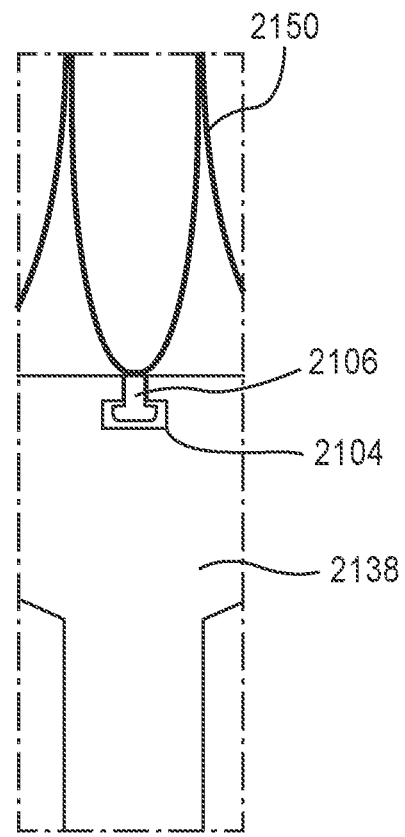
FIG. 58A is a side view of a portion of the prosthetic valve of FIG. 53 shown within a within a delivery sheath and coupled to a valve holder.
Figure 58C:
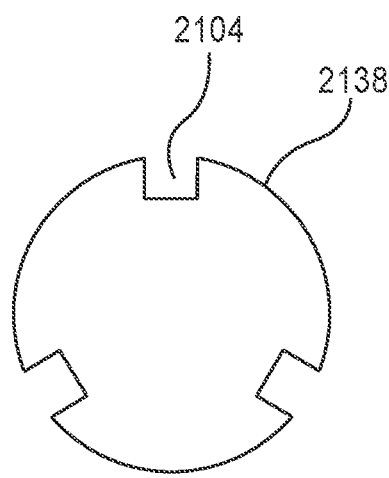
FIG. 58C is an end view of the valve holder of FIG. 58A.

In this embodiment, a valve holder 2138 (also referred to as a "pusher") is coupled to the inner frame 2150. In this manner, the valve holder 2138 can be used to hold the valve 2100 to aid in the control and manipulation of the valve 2100 as it is being deployed within a heart. In addition, the valve holder 2138 can limit radial expansion of the inner frame 2150 as the valve 2100 is moved within the lumen of the delivery sheath 2126 and during deployment. In this embodiment, the valve holder 2138 is coupled to the inner frame 2150 via couplers 2106 that are attached to the inner frame 2150 and that can be releasably received within corresponding recesses 2104 defined in the valve holder 2138 as best shown in FIGS. 58A-58C. In this embodiment, the couplers 2106 are in the form of a T-bar or hammer shape. It should be understood that couplers with other configurations and shapes can be used.

As shown in FIG. 58A, the couplers 2106 are received within the recesses 2104 and the valve 2100 and the valve holder 2138 can be disposed within the lumen of the delivery sheath 2126. The inner diameter of the delivery sheath 2126 can be sized such that when the valve holder 2138 and valve 2100 are disposed therein, the couplers 2106 are unable to exit the recesses 2104. In other words, the inner walls of the delivery sheath 2126 maintain the couplers 2106 within the recesses 2104. When the valve 2100 is moved outside of the delivery sheath 2126, the couplers 2106 will be able to freely exit the recesses 2104 releasing the inner frame 2150 from the valve holder 2138.

In alternative embodiments, the valve holder 2138 can be removably coupled to the valve 2100 (e.g., the inner frame 2150 of the valve 2100) via wires or sutures that can be cut after delivery of the valve 2100 to the heart. In some cases, the valve holder 2138 can be decoupled from the valve 2100 when the valve is still disposed within the delivery sheath 2126, while in other instances the valve holder 2138 can be decoupled from the valve 2100 after the valve 2100 exits the delivery sheath 2126 within the heart.

Although not shown, in other embodiments, the valve holder can contact and push the valve 2100 towards the distal end portion of the delivery sheath 2126, as described for previous embodiments, without securing the inner frame 2150 to the valve holder 2138. In such embodiments, in some instances, radial expansion of the inner frame 2150 can be restricted by the delivery sheath 2126 when the inner frame 2150 is disposed therein.

As with the embodiment of FIG. 52, in this embodiment a first actuation wire 2174 and a second actuation wire 2176 are coupled to the outer valve assembly 2110. More specifically, the outer frame 2120 of the outer valve assembly 2110 includes loops 2162 through which the first and second actuation wires 2174 and 2176 can be threaded or received therethrough. In this embodiment, the outer frame 2120 includes 12 loops 2162. The actuation wire 2174 is threaded through 6 of the loops 2162 and the actuation wire 2176 is threaded through 6 of the loops 2162. In other embodiments, there can be a different number of loops disposed on the outer frame 2120 and there can be more than two actuation wires or a single actuation wires. Further, each actuation wire can be threaded or received through a different number of loops than shown for this embodiment.

When the valve 2100 is disposed within the lumen of the delivery sheath 2126 as shown in FIG. 53, the actuation wires 2174 and 2176 extend out the distal end of the delivery sheath 2126, along the outside of the delivery sheath 2126, back through side apertures 2109 defined by the delivery sheath 2126, within the lumen of the delivery sheath 2126 and the two end portions of each of the actuation wires extend out a proximal end of the delivery sheath 2126. A user (e.g., physician) can grasp (directly, or via a control device, not shown) the end portions of the actuation wires 2174, 2176 to manipulate and control movement of the valve 2100 during deployment within a heart as described in more detail below. As described previously, in some embodiments, the actuation wires 2174, 2176 can be operatively coupled to the delivery system such that the user does not have to manually handle the actuation wires. For example, the actuation wires can be coupled to a delivery sheath and/or to a handle assembly (not shown) of the delivery system 2105.

Figure 54:
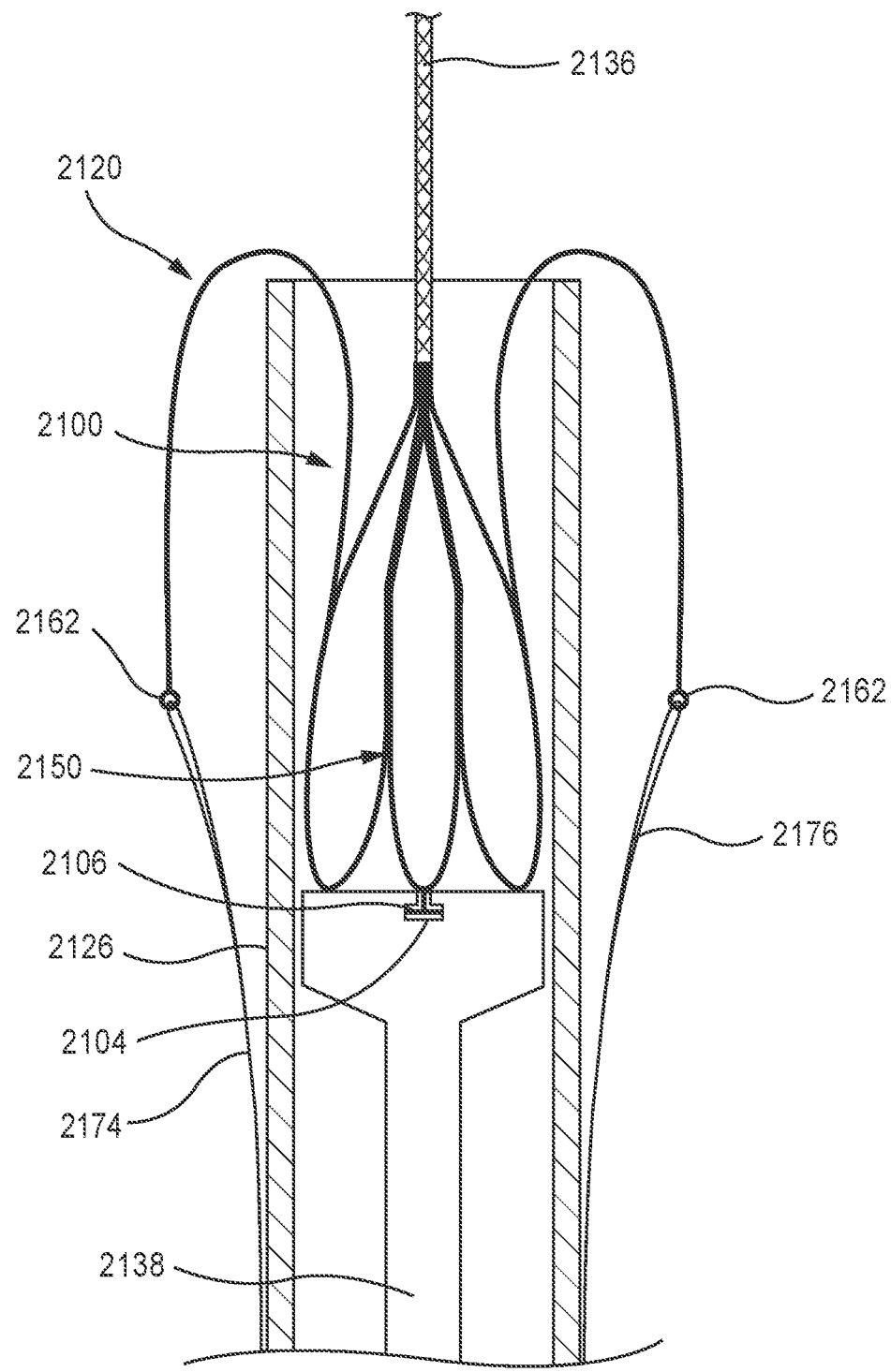
Figure 55:
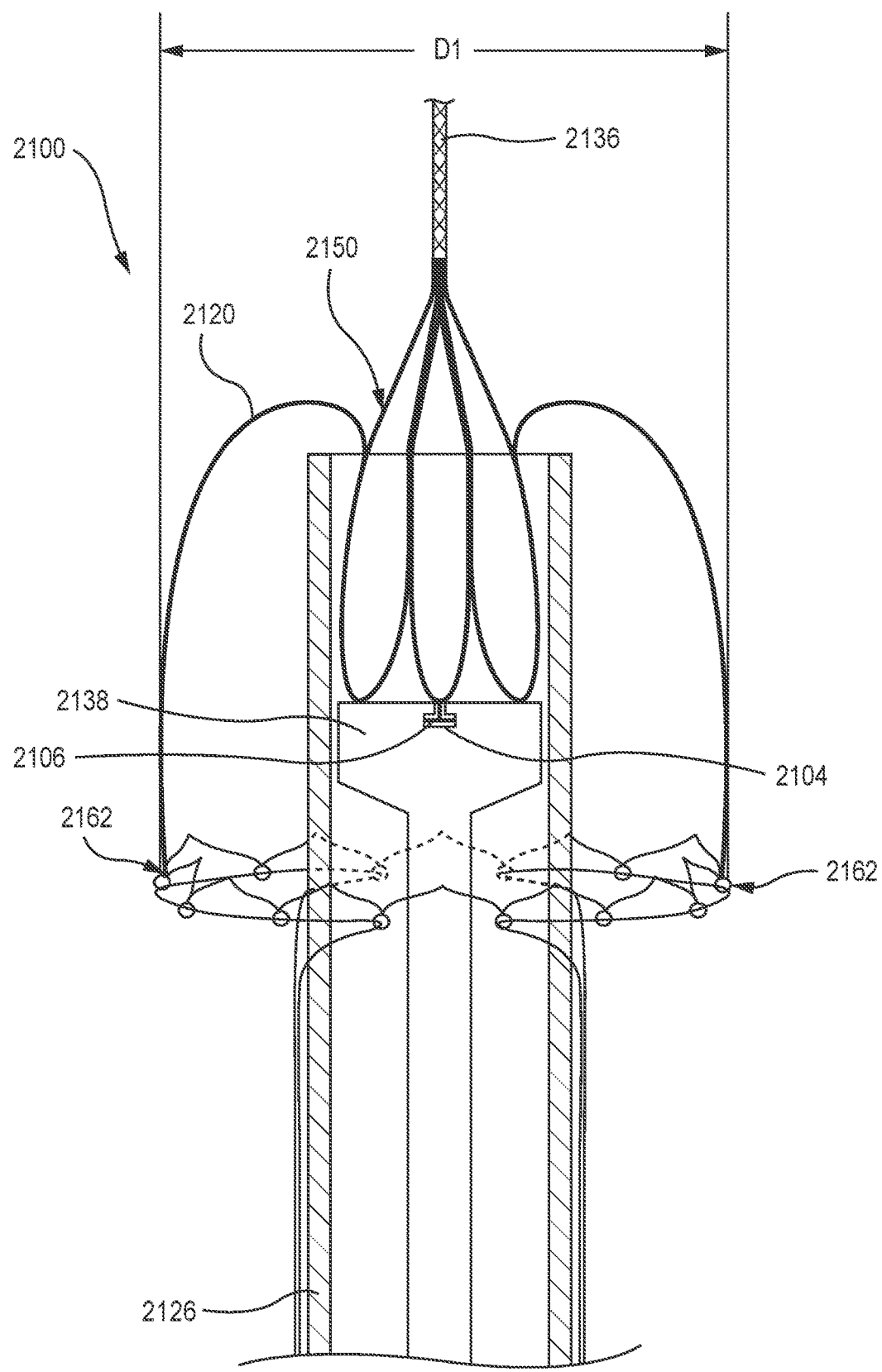
Figure 56:
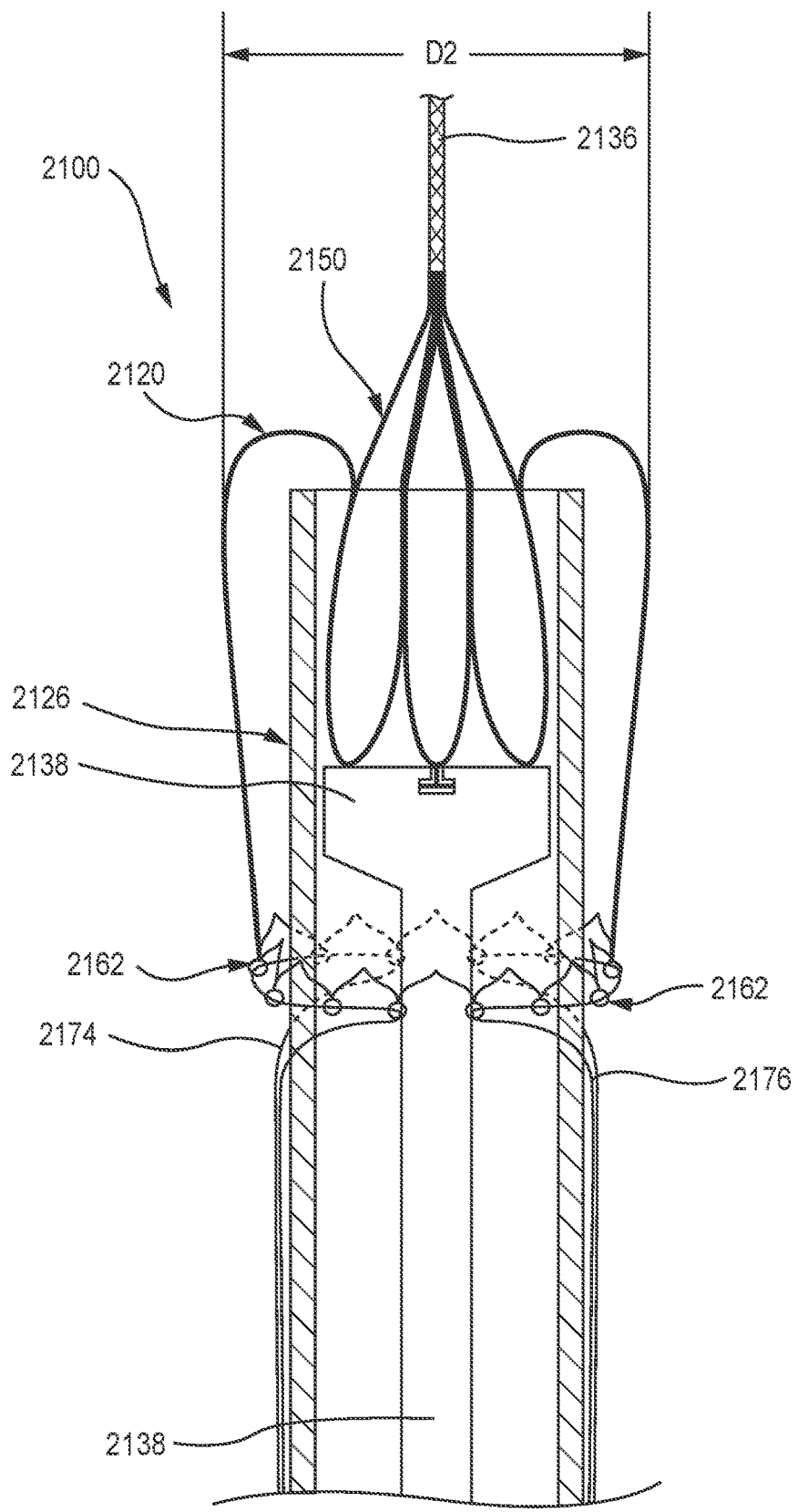
Figure 57:
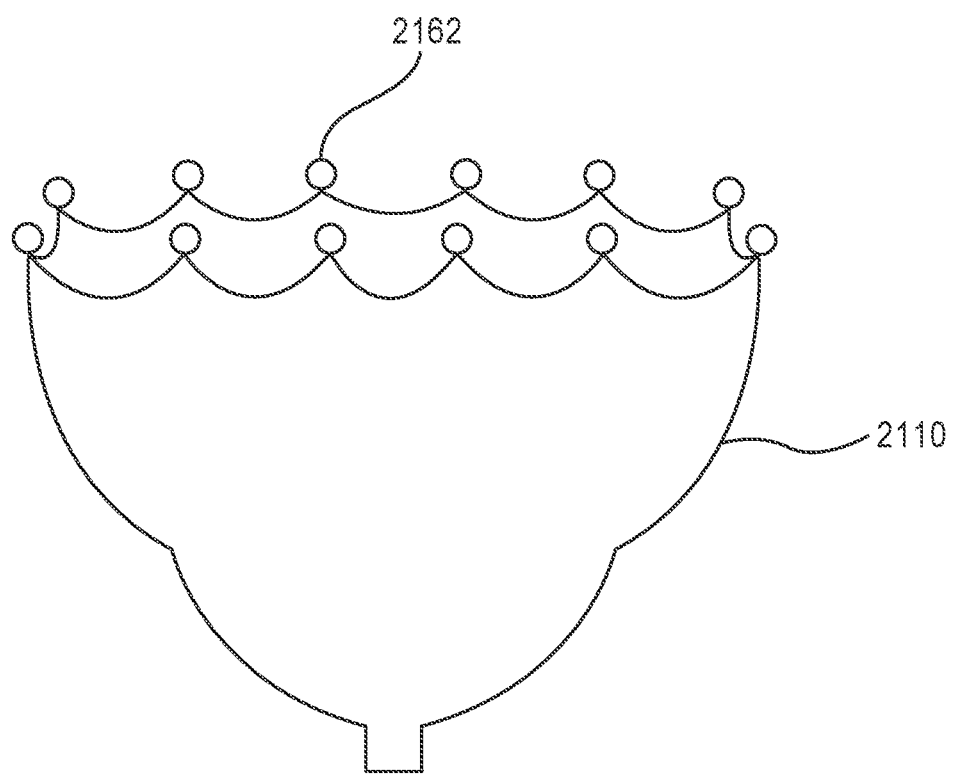
FIG. 57 is a perspective view of the outer frame assembly of the prosthetic valve of FIGS. 53-56.

The procedure to deliver the valve 2100 to the heart can be the same as or similar to any of the procedures described herein or in '572 PCT Application incorporated by reference above. For example, the valve 2100 can be delivered to the left atrium of the heart in the same or similar manner as described above with reference to FIGS. 43-48. With the distal end portion of the delivery sheath 2126 disposed within the left atrium of the heart, the valve 2100 can be deployed outside of the delivery sheath 2126. In this embodiment, to deploy the valve 2100, the user can pull proximally on the actuation wires 2174 and 2176 to pull the outer frame 2120 out of the delivery sheath in a controlled manner and such that the reversion of the outer frame 2120 from its inverted configuration relative to the inner frame 2150 can be controlled. In some cases, the tether 2136 coupled to the valve 2100 can be used to help pull the valve 2100 out of the lumen of the delivery sheath 2126. Alternatively, or in addition to, the valve holder 2138 can be used to push the valve 2100 distally out of the delivery sheath 2126. Thus, the valve 2100 can be moved outside of the delivery sheath 2126 by pushing with the valve holder 2138, pulling with the tether 2136, and/or pulling on the actuation wires 2174 and 2176. As the valve 2100 exits the lumen of the delivery sheath 2126, the outer frame 2120 exits first in its inverted configuration as shown in the progression of FIGS. 53-56. When the outer frame 2120 is at least partially outside of the lumen of the delivery sheath 2126, the outer frame 2120 can begin to revert to its expanded or deployed configuration, as shown in the progression of FIGS. 54-56, which can be similar to the progression described above with respect to FIGS. 15-21 and valve 300. In this embodiment, however, as shown in FIGS. 53-56, the actuation wires 2174 and 2176 can be used to selectively (e.g., by an operator) assist and/or control expansion, deployment and/or articulation of the valve 2100 as the valve 2100 is delivered to the heart. As shown in the progression of FIGS. 54-56, as the outer frame 2120 is moved outside of the lumen of the delivery sheath 2126 using the actuation wires 2174 and 2176, the outer frame 2120 can be transitioned from its inverted configuration to its expanded configuration as shown in FIG. 55.

In addition, in some instances, the actuation wires 2174 and 2176 can assist in the articulation and placement of the valve 2100 into its destination (e.g., a native annulus of an atrioventricular valve of a heart). For example, as shown in FIG. 56, the actuation wires 2174 and 2176 can also be used to constrain, collapse, or otherwise bias the valve 2100 (e.g., radially compress the outer frame 2120 of the valve 2100) after the valve 2100 exits the delivery sheath 2126 and is in its reverted, expanded or partially expanded configuration. In this manner, the actuation wires 2174 and 2176 can be used to move or urge the valve 2100 to a smaller configuration (i.e., smaller than its fully deployed, unbiased configuration). This may be desirable, for example, to reposition the valve 2100 within the heart before fully deploying the valve 2100. This is best shown by the sequence between FIG. 55 and FIG. 56.

As shown in FIG. 55, when the outer frame 2120 of the valve 2100 is disposed in its non-inverted and at least partially expanded configuration, the valve 2100 has a diameter D1. As shown in FIG. 56, when the outer frame 2120 of the valve 2100 is then moved to a compressed or restrained configuration, the valve 2100 has a diameter D2. As shown, D1 is greater than D2.

When the valve 2100 is positioned in a desired location within the heart, the actuation wires 2174 and 2176 can be released such that the outer fame 2120 can then move to its expanded configuration. The inner frame 2150 of the valve 2100 can then be moved distally out of the delivery sheath 2129 by moving the valve holder 2138 distally and/or by pulling on the tether 2136. When the valve holder 2138 is outside of the delivery sheath 2126 a sufficient distance to clear the recesses 2104, the couplers 2106 on the inner frame 2150 can freely be moved out of the recesses 2104, decoupling the inner frame 2150 from the valve holder 2138.

The actuation wires 2174 and 2176 can be decoupled from the outer frame 2120 either before or after deploying the inner frame 2150. For example, in this embodiment, to decouple the actuation wires 2174 and 2176 from the outer frame 2120, one end of each of the actuation wires 2174, 2176 can be pulled proximally, which will pull the opposite end of the actuation wires 2174 and 2176 out through the loops 2162. In alternative embodiments, where the actuation wires are tied or otherwise attached to the outer frame, the actuators can be cut, for example, to release the outer frame from the actuation wires.

Further, the actuation wires 2174 and 2176 can be decoupled from the outer frame 2120 at any suitable sequence or time period within the procedure. For example, in some instances, the actuation wires 2174 and 2176 can be released after the valve 2100 has at least partially exited the delivery sheath 2126 but before the valve 2100 is seated within the native annulus of the atrioventricular valve. In other instances, for example, the actuation wires 2174 and 2176 can be released after the valve 2100 has at least partially exited the delivery sheath 2126 and after the valve 2100 is seated within the native annulus of the atrioventricular valve.

Figure 59:
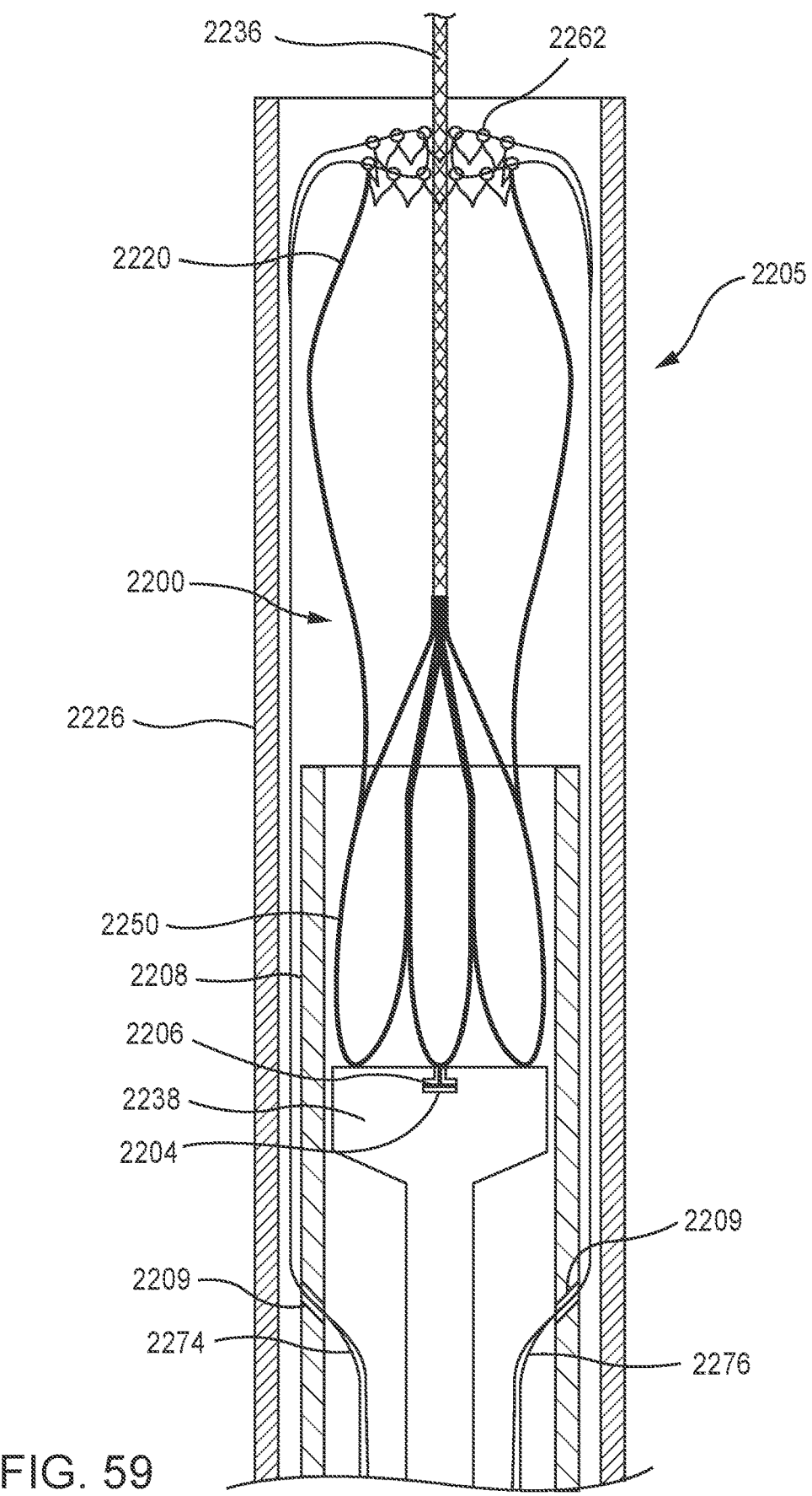
FIG. 59 is a cross-sectional side view of a prosthetic valve in an inverted configuration inside of a delivery sheath, according to an embodiment.

FIG. 59 illustrates another embodiment of a delivery system 2205 that can be used to deliver and deploy a prosthetic heart valve 2200 (also referred to herein as "valve") within a heart in a procedure similar to or the same as the procedures described above with respect to previous embodiments. Thus, some details regarding the valve 2200 and procedures performed therewith are not described herein. It should be understood that for features and functions not specifically discussed, those features and functions can be the same as or similar to the valves described above. The valve 2200 can be constructed the same as or similar to, and function the same as or similar to any of the valves described herein. For example, the valve 2200 includes an outer valve assembly 2210 that has an outer frame 2220, an inner valve assembly 2240 that has an inner frame 2250, and a tether 2236 coupled to the inner valve assembly 2240.

As with previous embodiments, the valve 2200 can be moved from a biased expanded configuration to an inverted configuration for delivery of the valve 2200 to the heart. More specifically, to place the valve 2200 in the inverted configuration, the outer frame 2220 can be moved to an inverted configuration relative to the inner frame 2250. In this embodiment, the valve 2200 is placed at least partially within a lumen of an inner sheath 2208 when the valve 2200 is in the inverted configuration, and disposed near a distal end of the inner sheath 2208. A valve holder 2238 is also disposed within the lumen of the inner sheath 2208. The inner frame 2250 can be releasably coupled to the valve holder 2238 with couplers 2206 in the same or similar manner as described above for valve 2100. Similarly, the outer frame 2220 includes loops 2262 through which actuation wires 2274 and 2276 can be threaded through in the same or similar manner as described above for valve 2100. The inner sheath 2208 is movably disposed within an outer delivery sheath 2226. As shown in FIG. 59, a portion of the valve 2200 is disposed outside of the inner sheath 2208 and within the lumen of the outer delivery sheath 2226. In some cases, the entire valve can be disposed within the lumen of the inner sheath 2208 prior to performing the procedure to deploy the valve.

In this embodiment, the inner sheath 2208 defines side apertures 2209 through which the actuation wires 2274 and 2276 can pass through. More specifically, as shown in FIG. 59, when the valve 2200 is disposed within the lumen of the inner sheath 2208, the actuation wires 2274 and 2276 extend proximally from the outer frame 2220, along the outside of the inner sheath 2208 and within the lumen of the outer delivery sheath 2226, back through side apertures 2209 defined by the inner sheath 2208, within the lumen of the inner sheath 2208, and the two end portions of each of the actuation wires 2274 and 2276 extend out a proximal end of the inner sheath 2208. A user (e.g., physician) can grasp the end portions of the actuation wires 2274, 2276 to manipulate and control movement of the valve 2200 during deployment within a heart as described above for valve 2100. As described previously, in some embodiments, the actuation wires 2274, 2276 can be operatively coupled to the delivery system such that the user does not have to manually handle the actuation wires. For example, the actuation wires 2274, 2276 can be coupled to a delivery sheath and/or to a handle assembly (not shown) of the delivery system 2205.

In this embodiment, at least a portion of the actuation wires 2274 and 2276 can be disposed within the interior of the delivery sheath 2226, thus limiting the exposure of the actuation wires 2274 and 2276 to areas external to the delivery sheath 2226 for at least a portion of the delivery and/or deployment of the valve 2200. The proximal end portions of the actuation wires 2274, 2276 can be used by the operator performing the delivery procedure to manipulate and control the deployment of the valve 2200. Although the side apertures 2209 defined by the inner sheath 2208 are shown as disposed at or near the distal end portion of the inner sheath 2208, in other embodiments, side apertures 2209 can be disposed at any suitable location along the length of the inner sheath 2208 (e.g., towards a middle portion or a proximal portion of the management sheath).

In this embodiment, to deliver the valve 2200 to the heart, the distal end of the outer delivery sheath 2226, with the valve 2200, inner sheath 2208 and valve holder 2238 disposed therein, is disposed within the left atrium of the heart. The delivery sheath 2226 can be pulled proximally to expose a portion of the valve 2200 and/or the inner sheath 2208 and valve holder 2238 can be moved distally to move at least the outer frame 2220 of the valve 2200 outside of the delivery sheath 2226. The actuation wires 2274 and 2276 can then be used to pull the distal end portions of the outer frame 2220 (e.g., where the loops 2262 of the outer frame 2220 are disposed) proximally to revert the outer frame to an uninverted configuration relative to the inner frame 2250. In addition, the tether 436 can also be used to help pull at least a portion of the valve 2200 out of the lumen of the inner sheath 2208 and the lumen of the outer delivery sheath 2226 during the delivery of the valve 2200 as discussed above for previous embodiments. Alternatively, or in addition to, the valve holder 2238 can be used to deliver and deploy the valve 2200. Thus, the valve 2200 can be deployed by pushing with the pusher device 480, pulling with the tether 436, or both.

When the outer frame has been reverted, the inner frame 2250 can be moved distally out of the inner sheath 2208 and decoupled from the valve holder 2238 in the same manner as described above for valve 2100. When released from the valve holder 2238, the inner frame 2250 can assume a biased expanded configuration. The actuation wires 2274 and 2276 can also be released from the outer frame 2220 in the same manner as described above for valve 2100. With both the outer frame 2220 and inner frame 2250 disposed within the atrium and in their biased expanded configurations, the valve 2200 can be seated in a desired position within the native annulus of the atrioventricular valve (e.g., the mitral valve).

Figure 60:
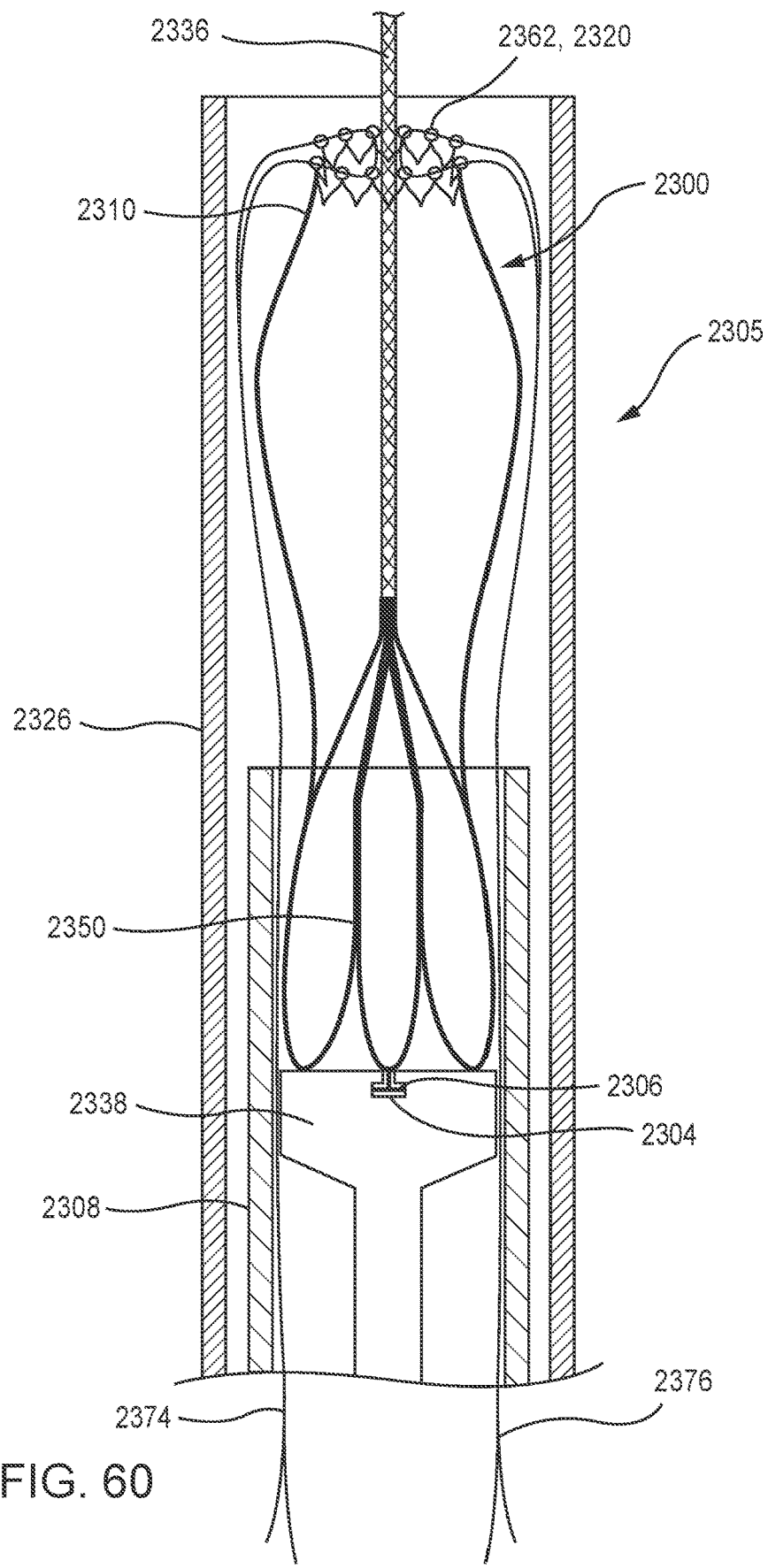
FIG. 60 is a cross-sectional side view of a prosthetic valve in an inverted configuration inside of a delivery sheath, according to an embodiment.

FIG. 60 illustrates another embodiment of a delivery system that can be used to deliver and deploy a prosthetic heart valve 2300 (also referred to as "valve") within a heart in a procedure similar to or the same as the procedures described above with respect to previous embodiments. Thus, some details regarding the valve 2300 and procedures performed therewith are not described with respect to this embodiment. It should be understood that for features and functions not specifically discussed, those features and functions can be the same as or similar to the valves and associated components described above for previous embodiments.

As shown in FIG. 60, the valve 2300 has an outer valve assembly 2310 that has an outer frame 2320, an inner valve assembly 2340 that has an inner frame 2350 and a tether 2336 coupled to the inner valve assembly 2340. As with previous embodiments, the valve 2300 can be moved from a biased expanded configuration to an inverted configuration for delivery of the valve 2300 to a heart. More specifically, to place the valve 2300 in the inverted configuration, the outer frame 2320 can be moved to an inverted configuration relative to the inner frame 2350. In this embodiment, the valve 2300 is placed at least partially within a lumen of an inner sheath 2308 when the valve 2300 is in the inverted configuration, and disposed near a distal end of the inner sheath 2308. A valve holder 2338 is also disposed within the lumen of the inner sheath 2308. The inner frame 2350 can be releasably coupled to the valve holder 2338 with couplers 2306 received within recesses 2304 defined by valve holder 2338 in the same or similar manner as described above for valve 2100. Similarly, the outer frame 2320 includes loops 2362 through which actuation wires 2374 and 2376 can be threaded through in the same or similar manner as described above for valve 2100. The inner sheath 2308 is movably disposed within an outer delivery sheath 2326. As shown in FIG. 60, a portion of the valve 2300 is disposed outside of the inner sheath 2308 and within the lumen of the outer delivery sheath 2326. In some cases, the entire valve can be disposed within the lumen of the inner sheath 2308 prior to performing the procedure to deploy the valve.

In this embodiment, the actuation wires are routed from the outer frame 2320 of the valve 2300, into the lumen of the outer delivery sheath 2326, through a distal end opening of the inner sheath 2308 and into the lumen of the inner sheath 2308. The wire actuators 2374 and 2376 extend proximally along an outer surface of the valve holder 2338, and the two end portions of each of the wire actuators 2374 and 2376 extend out a proximal end of the inner sheath 2308. Thus, a user (e.g., physician) can grasp the end portions of the actuation wires 2374, 2376 to manipulate and control movement of the valve 2300 during deployment within a heart as described above for valves 2100 and 2200. As described above, in some embodiments, the actuation wires 2374, 2376 can be operatively coupled to the delivery system 2305 such that the user does not have to manually handle the actuation wires. For example, the actuation wires 2374, 2376 can be coupled to a delivery sheath and/or to a handle assembly (not shown) of the delivery system 2305. As described for the previous embodiment, with the actuation wires 2374 and 2376 disposed within the interior of the delivery system (e.g., the lumen of the delivery sheath 2326 and lumen of the inner sheath 2308), limits the exposure of the actuation wires 2374, 2376 to areas external to the delivery system 2305 for at least a portion of the delivery and/or deployment of the valve 2300.

Figure 61:
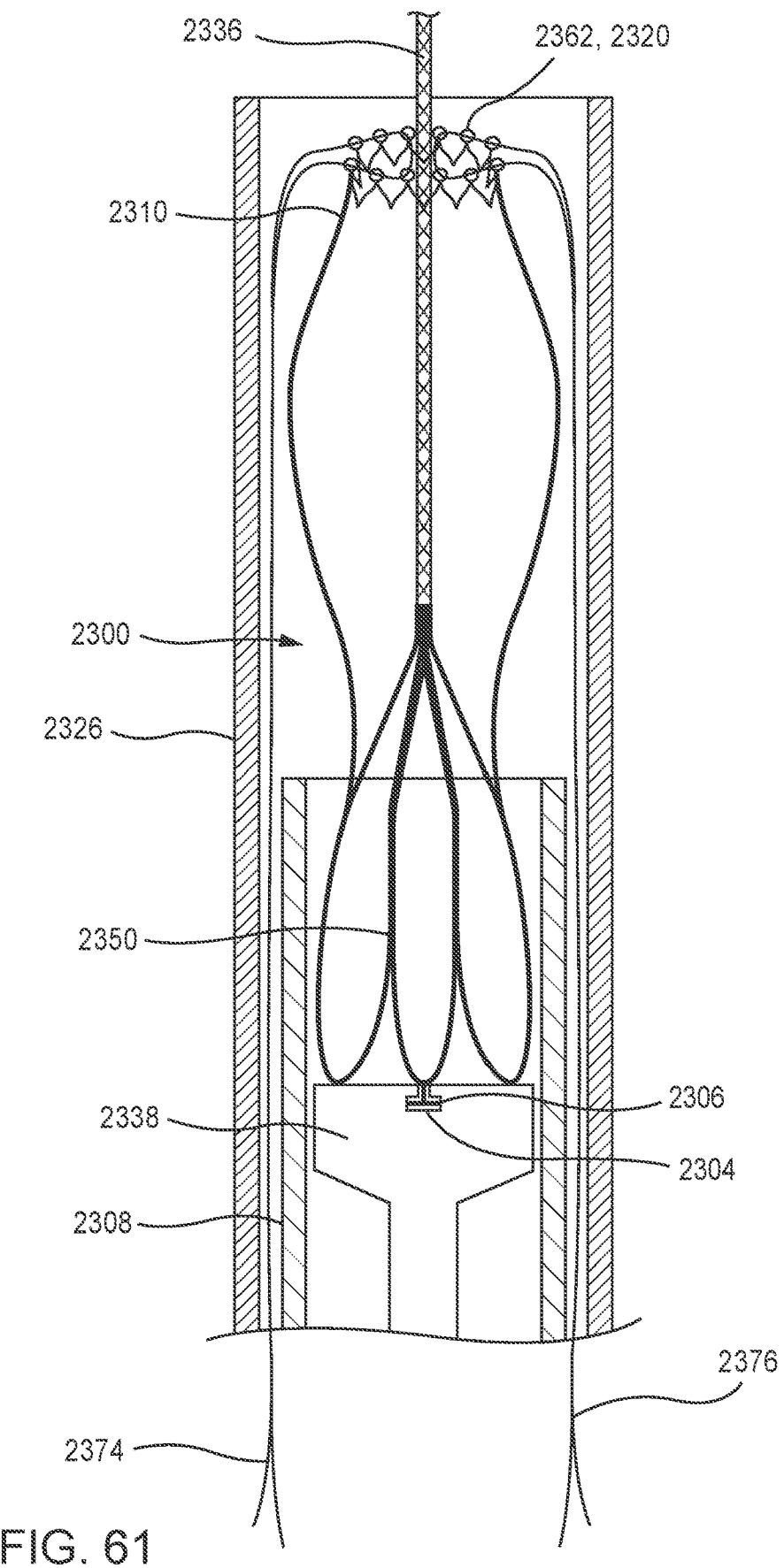
FIG. 61 is a cross-sectional side view of a prosthetic valve in an inverted configuration inside of a delivery sheath, according to an embodiment.

FIG. 61 illustrates a variation of the delivery system 2305 in which the actuation wires 2374 and 2376 are routed or passed between the outer delivery sheath 2326 and the inner sheath 2208 (i.e., through the lumen of the outer delivery sheath 2326 and external to the inner sheath 2308).

The delivery system 2305 (i.e., shown in FIG. 59 and FIG. 60), can be used in a procedure similar to or the same as the procedures described above with respect to valve 2200 to deliver and deploy the valve 2300 within a heart.

Figure 62:
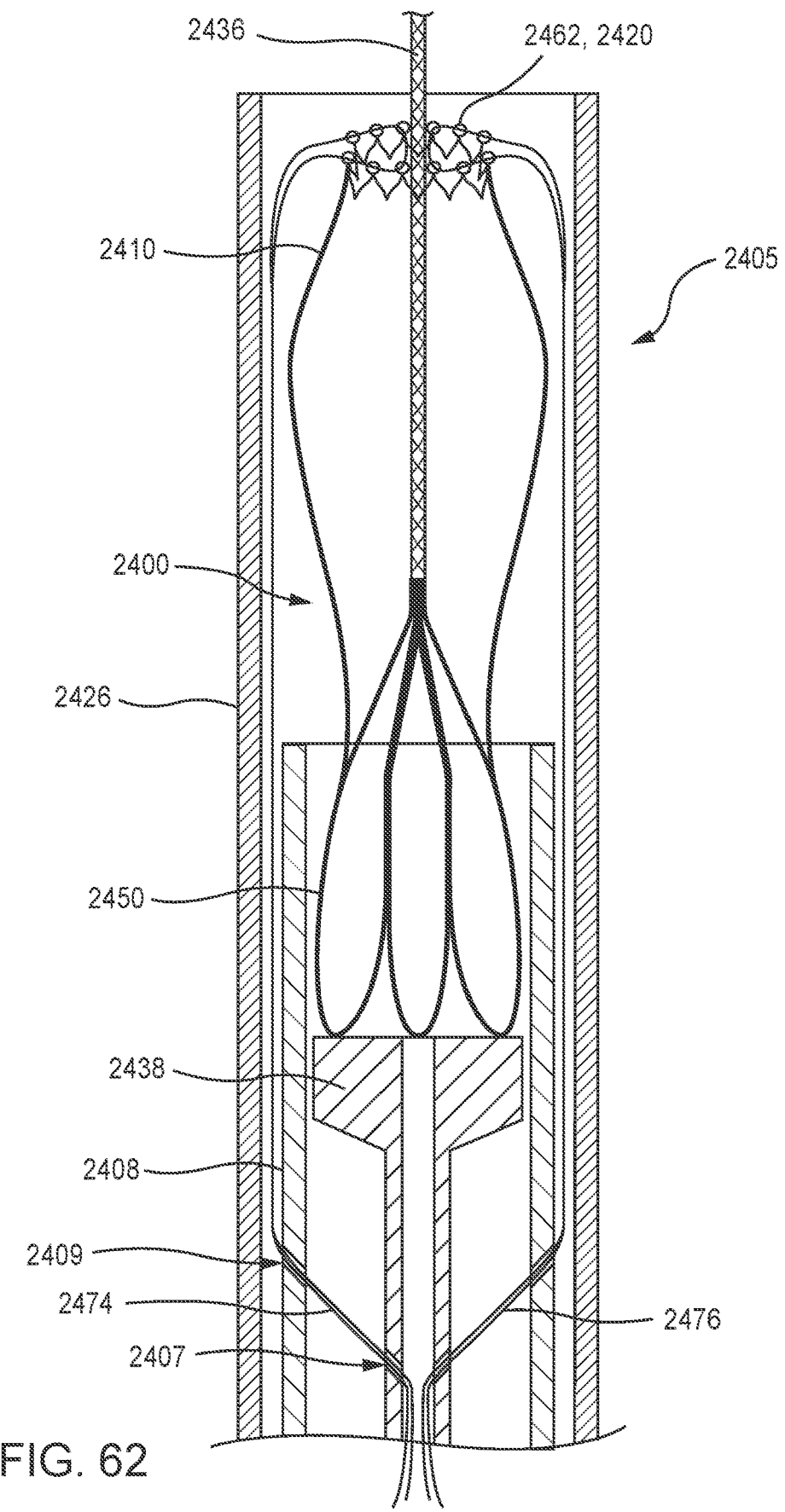
FIG. 62 is a cross-sectional side view of a prosthetic valve in an inverted configuration inside of a delivery sheath, according to an embodiment.

FIG. 62 illustrates another embodiment of a delivery system that can be used to deliver and deploy a prosthetic heart valve 2400. In this embodiment, a procedure similar to or the same as the procedures described above with respect to previous embodiments can be performed to deliver the prosthetic heart valve 2300 (also referred to herein as "valve"). Thus, some details regarding the valve 2400 and procedures performed therewith are not described herein. It should be understood that for features and functions not specifically discussed, those features and functions can be the same as or similar to the valves and associated components described above for previous embodiments.

As shown in FIG. 62, the valve 2400 includes an outer valve assembly 2410 having an outer frame 2420, an inner valve assembly 2440 having an inner frame 2450 and a tether 2436 coupled to the inner valve assembly 2440. As described above for previous embodiment, the outer frame 2420 of the valve 2400 can be moved between a biased expanded configuration and an inverted configuration in which the outer frame 2420 is inverted relative to the inner frame 2450. In this embodiment, with the outer frame 2420 in the inverted configuration, the valve 2400 is placed at least partially within a lumen of an inner sheath 2408, and disposed near a distal end of the inner sheath 2408. A valve holder 2438 is also disposed within the lumen of the inner sheath 2408. The inner frame 2450 is releasably coupled to the valve holder 2438 with couplers 2406 in the same or similar manner as described above for valve 2100. Similarly, the outer frame 2420 includes loops 2462 through which actuation wires 2474 and 2476 can be threaded through in the same or similar manner as described above for valve 2100. The inner sheath 2408 is movably disposed within an outer delivery sheath 2426. As shown in FIG. 62, a portion of the valve 2400 is disposed outside of the inner sheath 2408 and within the lumen of the outer delivery sheath 2426. In some cases, the entire valve can be disposed within the lumen of the inner sheath 2408 prior to performing the procedure to deploy the valve.

In this embodiment, the actuation wires 2474 and 2476 are routed from the outer frame 2420 of the valve 2400, into the lumen of the outer delivery sheath 2426, through side apertures 2409 defined by the inner sheath 2408 and into the lumen of the inner sheath 2408, and then through apertures 2407 defined by the valve holder 2438 and within a lumen defined by the valve holder 2438. The two end portions of each of the actuation wires 2474 and 2476 extend out a proximal end of the lumen of the valve holder 2438. Thus, a user (e.g., physician) can grasp the end portions of the actuation wires 2474, 2476 to manipulate and control movement of the valve 2400 during deployment within a heart as described above for previous embodiments. As described above, in some embodiments, the actuation wires 2474, 2476 can be operatively coupled to the delivery system 2405 such that the user does not have to manually handle the actuation wires. For example, the actuation wires 2474, 2476 can be coupled to a delivery sheath and/or to a handle assembly (not shown) of the delivery system 2405. The delivery system 2405 can be used in a procedure similar to or the same as the procedures described above with respect to valve 2400 to deliver and deploy the valve 2400 within a heart.

In an alternative embodiment (not shown), including a delivery apparatus that includes an outer delivery sheath, an inner sheath and a valve holder, the actuation wires can be routed or passed from a distal end of the valve, through a lumen of the outer delivery sheath, through a distal end opening of the valve holder, and through a lumen of the valve holder. In some embodiments, the actuation wires can be routed from the outer frame of the valve, through side apertures defined by the outer delivery sheath, into the lumen of the delivery sheath, through a distal end opening of the inner sheath and into the lumen of the inner sheath, through side apertures of the valve holder and into the lumen of the valve holder. In other embodiments, various other routing paths for the actuation wires can be defined depending on the particular configuration of the delivery sheath (e.g., with or without side apertures), the inner sheath (e.g., with or without side apertures) and/or the valve holder (with or without a lumen and/or with or without side apertures).

Figure 63:
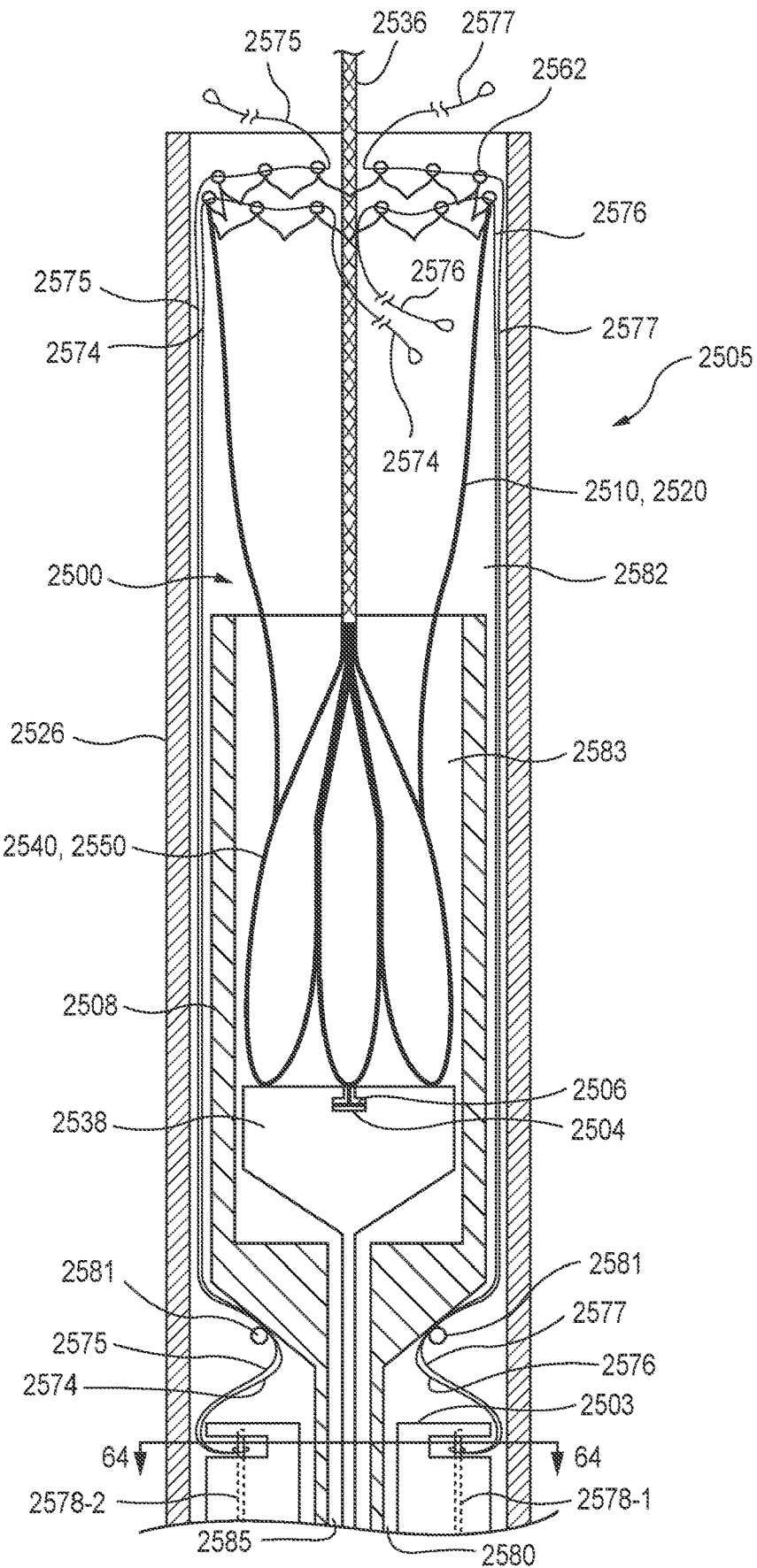
FIG. 63 is a partial cross-sectional side view of a delivery system and prosthetic heart valve, according to an embodiment.

FIGS. 63-71 illustrate a delivery system 2505 for delivering and deploying a prosthetic heart valve, such as, prosthetic heart valve 2500, within a heart, according to another embodiment. The prosthetic heart valve 2500 (also referred to herein as "valve") can be constructed the same as or similar to, and function the same as or similar to any of the valves described herein. Thus, some details regarding the valve 2500 are not described herein. As shown in FIG. 63, the valve 2500 has an outer valve assembly 2510 with an outer frame 2520 and an inner valve assembly 2540 with an inner frame 2550, and a tether 2536 coupled to the inner frame 2550. As described above for previous embodiments (e.g., valve 100, 200, 300 etc.), the outer frame 2520 and the inner frame 2550 of valve the 2500 can each be formed with a shape-memory material and have a biased, expanded or deployed configuration. The outer frame 2520 and the inner frame 2550 can be moved to a collapsed or undeployed configuration for delivery of the valve 2500 to the heart in which the outer frame 2520 is inverted relative to the inner frame 2550. To prepare the valve 2500 for delivery to the heart, the outer frame 2520 of the valve 2500 is first disposed in a prolapsed or inverted configuration as shown in FIG. 63. Specifically, the elastic or superelastic structure of outer frame 2520 of valve 2500 allows the outer frame 2520 to be disposed in the prolapsed or inverted configuration relative to the inner frame 2550 as described above, for example with respect to valve 100.

For example, to dispose the outer frame 2520 in its inverted configuration relative to the inner frame 2550, the outer frame 2520 is folded or inverted distally such that the outer frame 2520 is pointed away from the inner frame 2550. With the outer frame 2120 in the inverted configuration, the valve 2500 can be placed within a lumen of the delivery system 2505 as shown in FIG. 63 for delivery of the valve 2500 to the left atrium of the heart. As discussed above, by disposing the outer frame 2520 of the valve 2500 in the inverted configuration, the valve 2500 can be collapsed into a smaller overall diameter, i.e., placed in a smaller diameter delivery sheath, than would be possible if the valve 2500 were collapsed radially when the inner frame 2550 and the outer frame 2520 are disposed concentric to one another.

In this embodiment, the delivery system 2505 includes an outer delivery sheath 2526, an inner sheath 2508, a valve holder 2538 (also referred to as a "pusher") and a multi-lumen elongate tube member 2503 (also referred to as "tube" or "tube member" or "multi-lumen elongate member"). As shown in FIGS. 63 and 68-70, the tube member 2503 is movably disposed within a lumen 2582 defined by the outer delivery sheath 2526. The inner sheath 2508 is movably disposed within the lumen 2582 and within a lumen 2580 defined by the tube member 2503. The valve holder 2538 is movably disposed within a first lumen 2583 and a second lumen 2585 defined by the inner sheath 2508 that are in fluid communication with each other.

To deploy the valve 2500 within a heart, the outer frame 2520 of the valve 2500 is first moved or placed in its inverted configuration relative to the inner frame 2550. As shown in FIG. 63, a portion of the valve 2500 is placed within the lumen 2582 of the outer sheath and a portion of the valve 2500 is placed within the lumen 2583 of the inner sheath 2508. As described above for previous embodiments, when the valve 2500 is placed within the delivery system (e.g., outer sheath 2526 and inner sheath 2508) the valve 2500 can be compressed or collapsed to a smaller configuration (e.g., a smaller outer perimeter).

The inner frame 2550 can be releasably coupled to the valve holder 2538 via couplers 2506 that are received within corresponding recesses 2504 defined by the valve holder 2538 in the same manner as described above for delivery system 2105 (see, e.g., FIGS. 58A-58C). In this manner, the valve holder 2538 can be used to hold the valve 2500 to aid in the control and manipulation of the valve 2500 as it is being deployed within a heart. In addition, the valve holder 2538 can limit radial expansion of the inner frame 2550 as the valve 2500 is moved within the lumen of the delivery sheath 2526 and during deployment outside of the delivery sheath 2526. As described above for valve 2100, an inner diameter 2582 of the inner sheath 2508 can be sized such that when the valve holder 2538 and valve 2500 are disposed therein, the couplers 2506 are unable to exit the recesses 2504. In other words, the inner walls of the inner sheath 2508 maintain the couplers 2506 within the recesses 2504. When the valve 2500 is moved outside of the inner sheath 2508, the couplers 2506 will be able to freely exit the recesses 2504, releasing the inner frame 2550 from the valve holder 2538.

In alternative embodiments, the valve holder 2538 can be removably coupled to the valve 2500 (e.g., the inner frame 2550 of the valve 2500) via wires or sutures that can be cut after delivery of the valve 2500 to the heart. In some cases, the valve holder 2538 can be decoupled from the valve 2500 when the valve is still disposed within the outer delivery sheath 2526, while in other instances the valve holder 2538 can be decoupled from the valve 2500 after the valve 2500 exits the delivery sheath 2526 within the heart.

Although not shown, in other embodiments, the valve holder 2538 can merely contact and push the valve 2500 during deployment, as described for previous embodiments, without securing the inner frame 2550 to the valve holder 2538. In such embodiments, in some instances, radial expansion of the inner frame 2550 can be restricted by the inner sheath 2508 when the inner frame 2550 is disposed therein.

In this embodiment a first actuation wire 2576, a second actuation wire 2574, a third actuation wire 2576 and a fourth actuation wire 2577 are each coupled to the outer valve assembly 2510. More specifically, the outer frame 250 of the outer valve assembly 2510 includes loops 2562 through which the actuation wires 2574-2577 can be threaded or received therethrough. In this embodiment, the outer frame 2520 includes 12 loops 2562 and each actuation wire 2574-2577 is threaded through 3 of the loops 2562. In other embodiments, there can be a different number of loops disposed on the outer frame 2520 and there can be a different number of actuators. Further, each actuation wire can be threaded or received through a different number of loops than shown for this embodiment.

When the valve 2500 is disposed within the delivery system 2505 as shown, for example, in FIG. 63, the actuation wires 2574-2577 each extend from the outer frame 2520 proximally within the lumen 2582 of the outer sheath and along an outside wall of the inner sheath 2508, are tucked or placed behind one or more seals 2581 or other holding device, and pinned by an elongate pinning member 2578-1, 2578-2, 2578-3, 2578-4 (collectively referred to as pinning members 2578) to the tube member 2503. The seal 2581 can be configured such that the actuation wires 2574-2577 can slide relative to the seal 2581 during actuation and deployment of the valve 2500 as described in more detail below.

As shown in FIGS. 63 and 68-70, a first end of the actuation wire 2574 and a first end of the actuation wire 2575 are pinned by a pinning member 2578-2, and a first end of the actuation wire 2576 and a first end of the actuation wire 2577 are pinned by a pinning member 2578-1. A second end of the actuation wire 2574 and a second end of the actuation wire 2576 are pinned by a pinning member 2578-4 (not shown in the partial cross-sectional views of FIGS. 63 and 68-70), and a second end of the actuation wire 2575 and a second end of the actuation wire 2577 are pinned by a pinning member 2578-3 (not shown in the partial cross-sectional views of FIGS. 63 and 68-70). The second ends of the actuation wires are shown detached in FIGS. 63 and 68-70 for ease of illustration.

Figure 64:
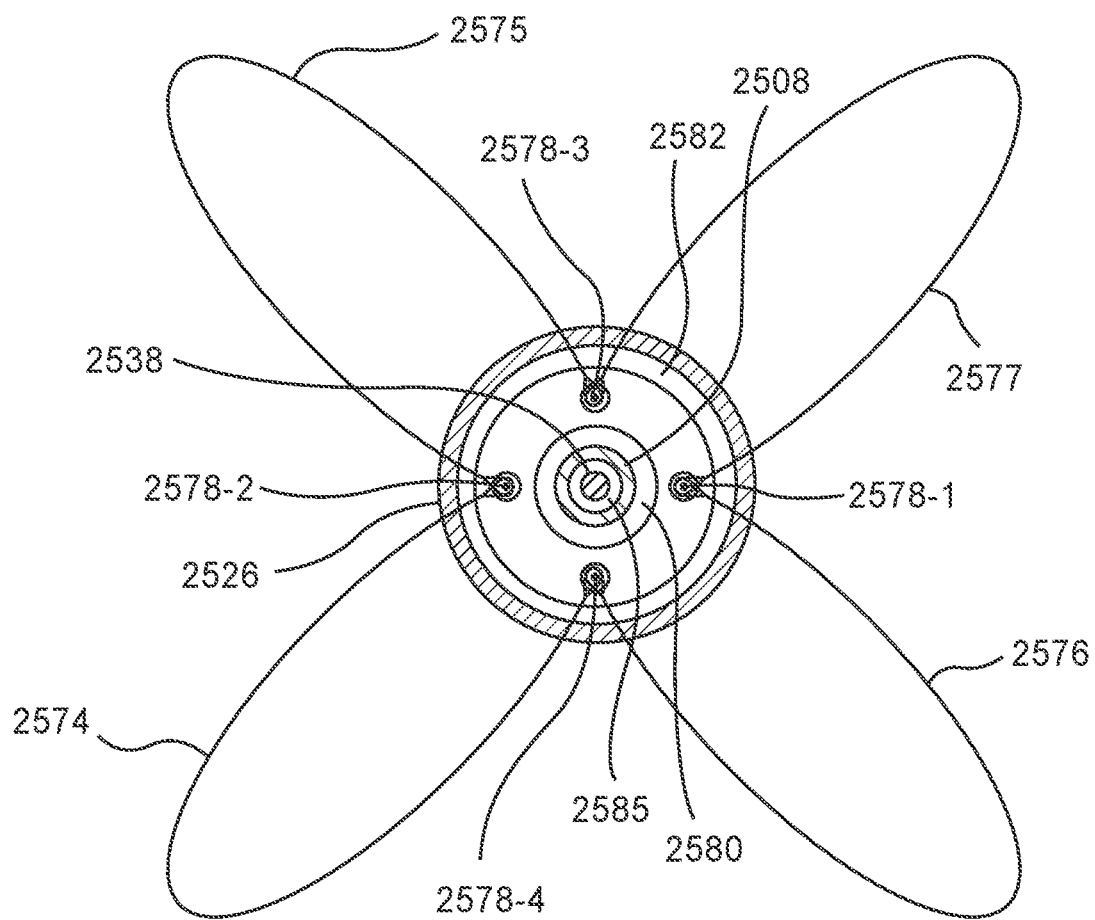
FIG. 64 is a cross-sectional view taken along line 64-64 in FIG. 63 showing the actuation wires coupled to a tube member of the delivery system.

FIG. 64 is a cross-sectional view taken along line 64-64 in FIG. 63 and illustrates the pinning of the actuation wires 2574-2577. The actuation wires 2574-2577 are shown unattached to the outer frame for illustration purposes. FIG. 67A illustrates the actuation wire 2574 and is representative of the other actuation wires 2575-2577. FIGS. 67B, 67B and 67C illustrate alternative embodiments for the actuation wires labeled 2574',2574" and 2574'". As shown in FIG. 67A, the actuation wires 2574-2577 each include a loop on both ends of the actuation wire, which is pinned by the pinning members 2578. In FIG. 67B, the pinning members can pin the smaller loop on one end of the actuation wire 2574' and the end of the larger loop on the opposite end of the actuation wire 2574'. In FIG. 67C, the actuation wire 2475" is in the form of a closed loop and each end of the loop can be pinned by a pinning member. In FIG. 67D, the actuation wire 2574''' includes two elongate loops and a center smaller loop. In this embodiment, the actuation wire 2574''' can be pinned by three pinning members, a first pinning member can pin an end of one of the larger loops, a second pinning member can pin an end of the other larger loop, and the small loop can be pinned by a third pinning member. In each of the embodiments of FIGS. 67B-67D, a double layer of the actuation wire would be passed or threaded through the loops of the outer frame of the valve. Other alternative configurations can also be used.

As shown in FIGS. 65 and 66A, the multi-lumen tube member 2503 defines four pinning member lumens 2579-1, 2579-2, 2579-3, 2579-4 (collectively referred to as pinning member lumens 2579). The end portions of the actuation wires 2574-2577 are placed within the circumferential recess or groove 2584 defined by the tube member 2503, where the pinning members 2578 are received through the loops on the ends of the actuation wires 2574-2577, pinning the actuation wires 2574-2577 to the tube member 2503. Thus, during deployment of the valve 2500 within a heart, a user (e.g., physician) can use the tube member 2503, to which the actuation wires 2574-2577 are coupled, to control and/or manipulate movement of the valve 2500 as described in more detail below.

Figure 66B:
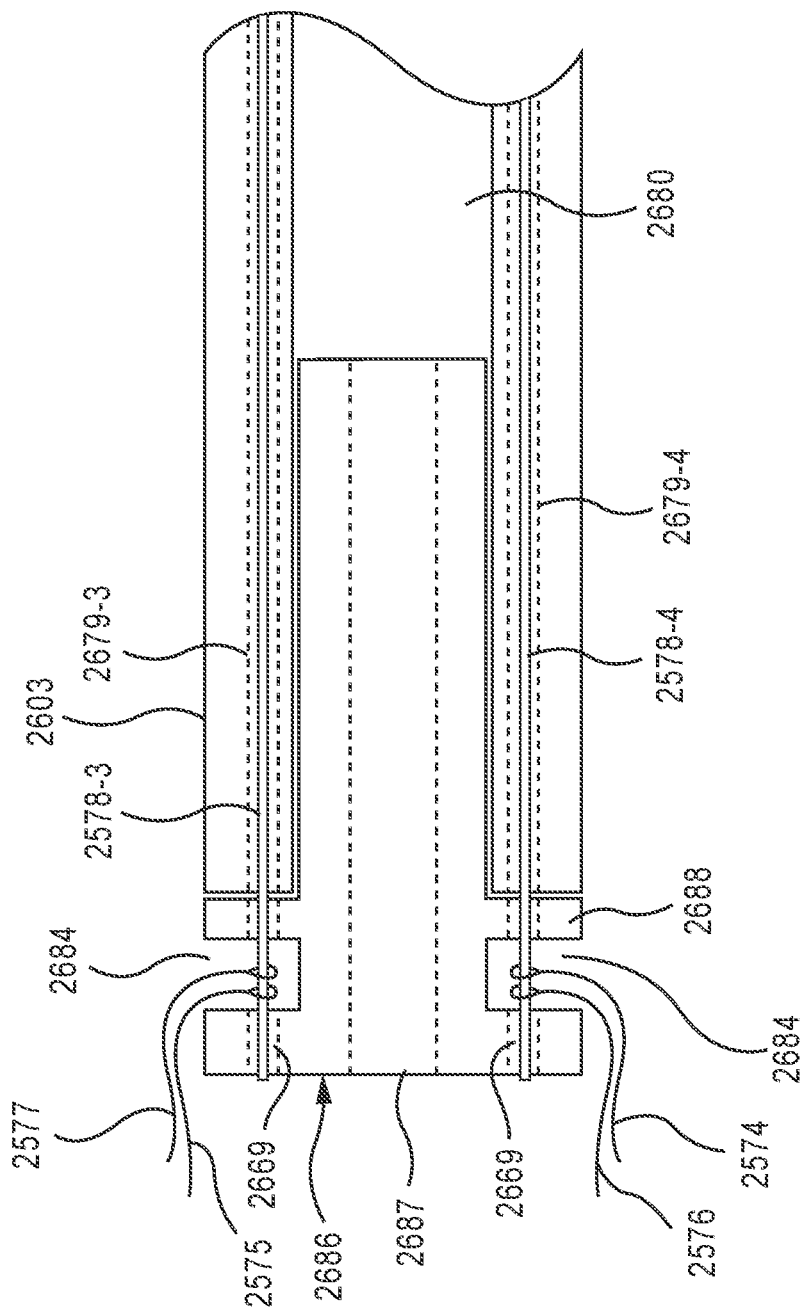
FIG. 66B is a side view of a portion of a multi-lumen tube member according to another embodiment and a distal retention element according to an embodiment.
Figure 66C:
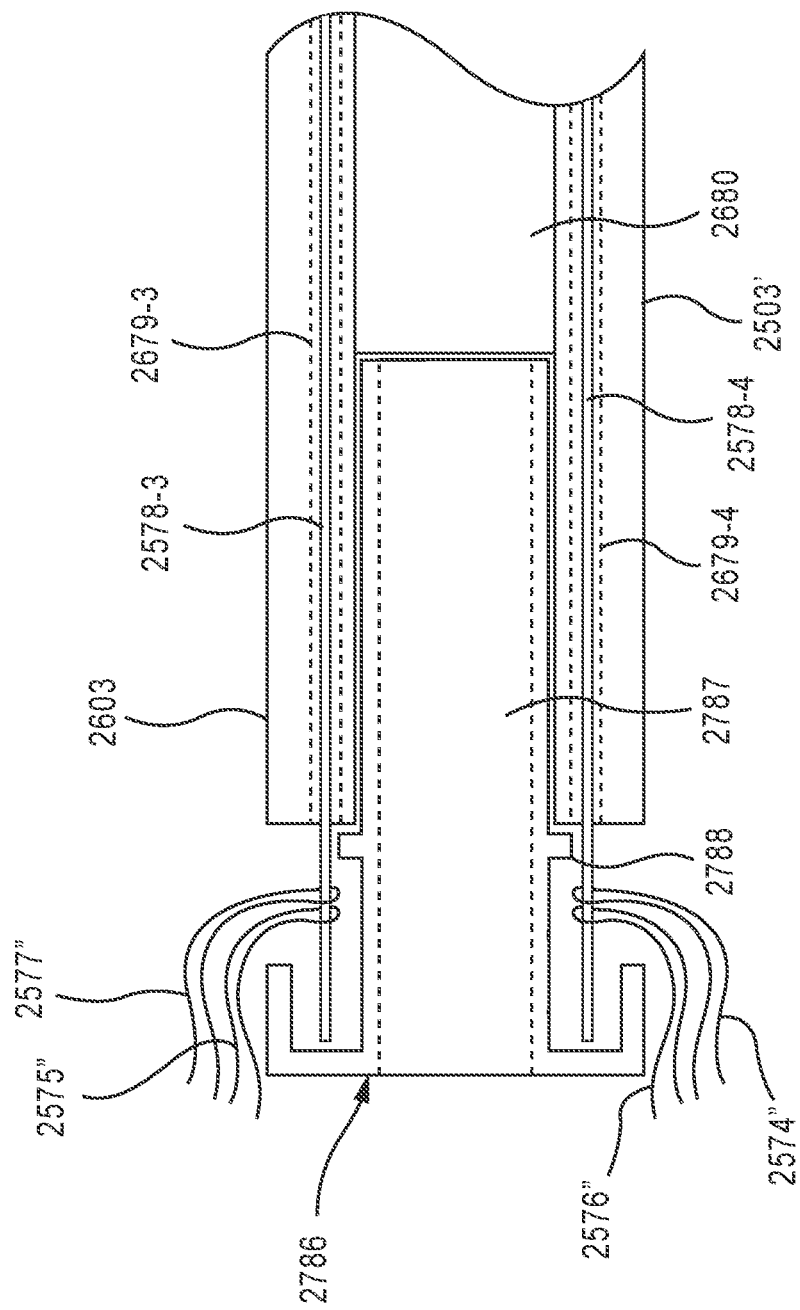
FIG. 66C view of a portion of the multi-lumen tube member of FIG. 66B and a distal retention element, according to another embodiment.

FIGS. 66B and 66C, illustrate an alternative embodiment of a multi-lumen tube member 2603 that can be used with a distal retention element 2686 as shown in FIG. 66B, or a distal retention element 2786 as shown in FIG. 66C. The distal retention elements 2686 and 2786 can be disposed abutting a distal end of the multi-lumen tube member 2603 and can define at least in part a recess area to receive the loop ends of the actuation wires, and can provide increased overall strength and durability to the multi-lumen tube member 2603 during delivery and deployment of the prosthetic valve. The distal retention element 2686, 2786 can be formed with the same or a different material as the multi-lumen tube member 2603. In some embodiments, in may be desirable for the distal retention element 2686, 2786 to be formed of a material having greater strength characteristics than the multi-lumen tube member 2603. For example, the distal retention element 2686, 2786 can be formed with a metal or rigid plastic.

As shown in FIGS. 66B and 66C, the multi-lumen tube member 2603 (also referred to herein as "tube member") can define a center lumen 2680 and multiple pinning member lumens, including pinning member lumens 2679-3 and 2679-4 (collectively referred to as 2679) shown in FIGS. 66B and 66C that can receive therein pinning members, such as pinning members 2578-3 and 2578-4, respectively. Although not show, the tube member 2603 can also define pinning member lumens that can receive pinning members 2578-1 and 2578-2 as shown for tube member 2503 in FIG. 65.

As shown in FIG. 66B, the distal retention element 2686 can be received within the lumen 2680 and can define a lumen 2687 through which the valve holder 2538 can be slidably received. Although not shown, the distal retention element 2686 can be coupled to the tube member 2603 using various different coupling methods. For example, in some embodiments, the distal retention element 2686 can be bonded to the tube member 2603. In some embodiments the distal retention element 2686 can include a feature(s), such as barbs, that allow it to be inserted into the tube member 2603, but not removed. In some embodiments the distal retention element 2686 can include notches that interlock with a corresponding feature o the tube member 2603 and/or the tube member 2603 can be reflowed or molded over the retention element 2686. Various other coupling methods and/or combinations of securement strategies could be used to couple the distal retention element 2686 to the tube member 2603. In some embodiments, the distal retention element 2686 can extend proximally within the lumen 2680 of the tube member 2603 and be coupled at a proximal end portion of the tube member 2603.

The distal retention element 2686 also defines pinning member lumens 2669 that align with the pinning member lumens 2679 of the multi-lumen tube member 2603 such that the pinning members 2578 can be received therein. A proximal shoulder 2688 can be disposed abutting a distal end of the multi-lumen tube member 2603. The distal retention element 2686 also defines a circumferential recess area 2684 defined between the proximal shoulder 2688 and a distal end portion of the distal retention element 2686. As shown in FIG. 66B, the loop ends of the actuation wires 2574-2577 can be received within the recess area 2684 and pinned by the pinning members 2578 as described above for multi-lumen tube member 2503.

FIG. 66C illustrates a distal retention element 2786 disposed abutting the distal end of the multi-lumen tube member 2603. As with the previous embodiment, the distal retention element 2786 can be received within the lumen 2680 and can define a lumen 2787 through which the valve holder 2538 can be slidably received. The distal retention element 2786 can be coupled to the tube member 2603 in the same manner as described above for distal retention element 2686. The distal retention element 2786 also includes a proximal shoulder 2788 configured to abut the distal end of the multi-lumen tube member 2603. The distal retention element 2786 also defines a circumferential recess area 2784 that can receive the loop ends of actuation wires 2574"-2577", which can be pinned by the pinning members 2578 (2578-3 and 2578-4 shown in FIG. 66C). In this example, the actuation wires are configured as a closed loop as shown for actuation wire 2574" in FIG. 67C.

Figure 68:
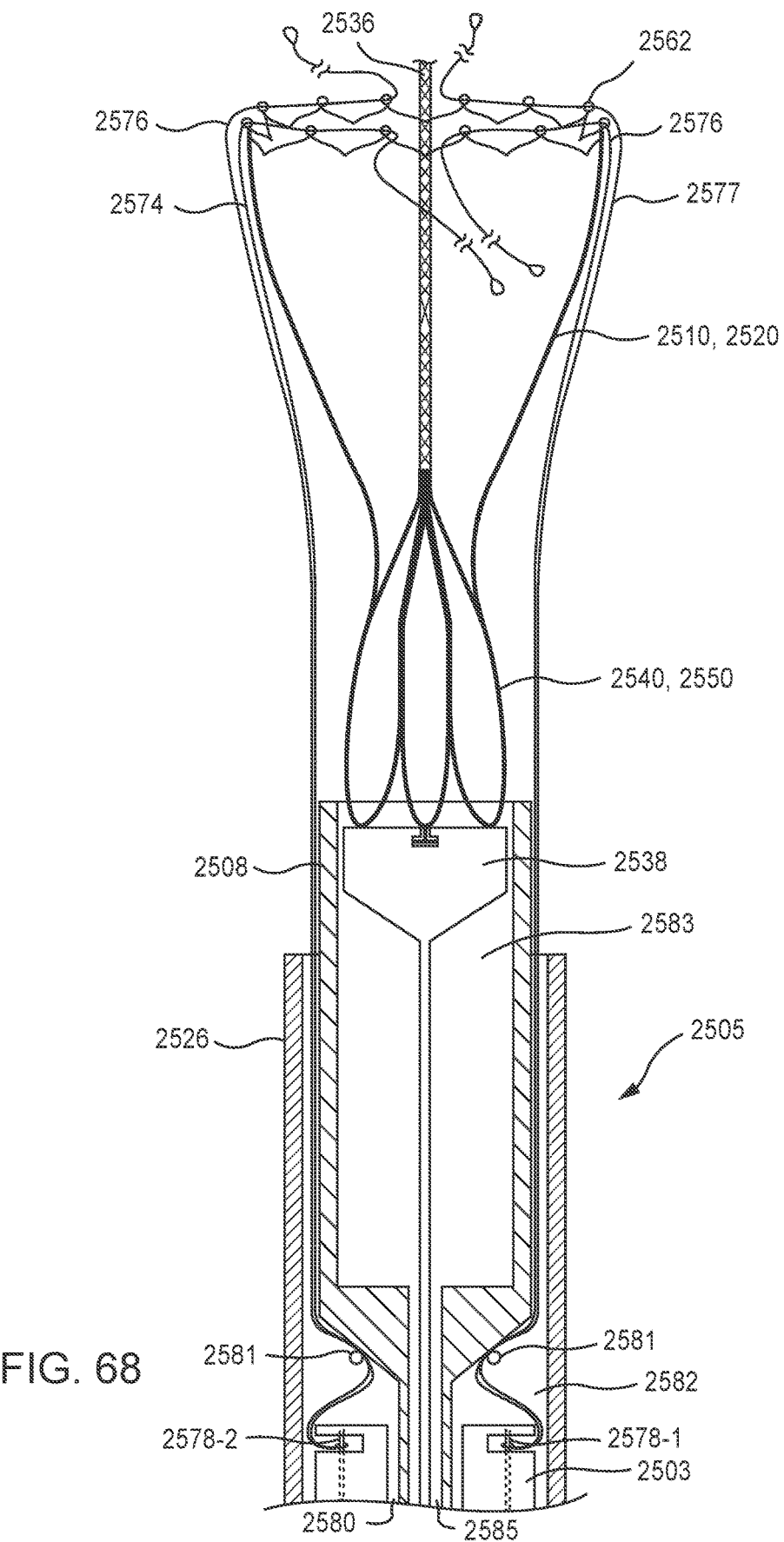
FIG. 68 is a partial cross-sectional side view of the delivery system and prosthetic heart valve of FIG. 63, shown in a first partially deployed configuration.

The procedure to deliver the valve 2500 to the heart can be the same as or similar to any of the procedures described herein or in '572 PCT Application incorporated by reference above. For example, the valve 2500, disposed within the delivery system 2505 in an inverted configuration, can be delivered to the left atrium of the heart in the same or similar manner as described above with reference to FIGS. 43-48. With the distal end portion of the delivery sheath 2526 disposed within the left atrium of the heart, the valve 2500 can be deployed outside of the delivery sheath 2526. For example, as shown in FIG. 68, the inner sheath 2508, valve holder 2538 and tube member 2503 can be moved distally relative to the outer sheath 2526, moving or pushing the valve 2500 outside the lumen 2582 of the outer sheath 2526. In addition, or alternatively, the outer sheath 2526 can be moved or pulled proximally, leaving at least a portion of the valve 2500 disposed within the heart. In some cases, the tether 2536 coupled to the valve 2500 can be used to help pull the valve 2500 out of the lumen of the outer sheath 2526.

Figure 69:
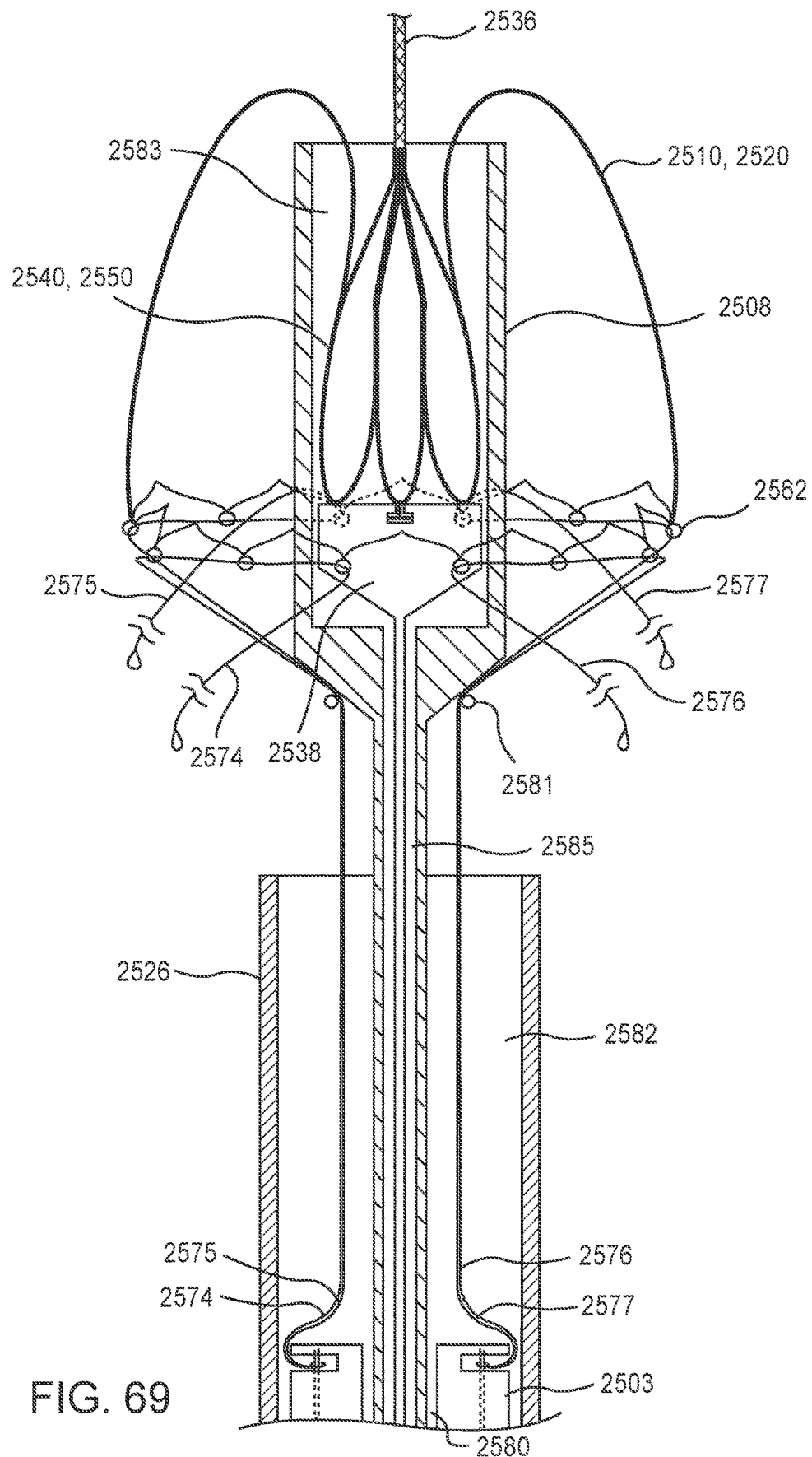
FIG. 69 is a partial cross-sectional side view of the delivery system and prosthetic heart valve of FIG. 63, shown in a second partially deployed configuration.

As described above for previous embodiments, as the outer frame 2520 becomes unconstrained by the outer sheath 2526, the outer frame 2520 can begin to revert to its expanded or uninverted configuration. The actuation wires 2575-2577 can be used to control the reversion of the outer frame 2520. More specifically, the tube member 2503 can be pulled proximally such that the actuation wires (pinned to the tube member 2503) pull the distally disposed portion of the outer frame 2520 proximally (as shown in FIG. 69) in a controlled manner and such that the reversion of the outer frame 2520 from its inverted configuration relative to the inner frame 2550 can be controlled.

Figure 70:
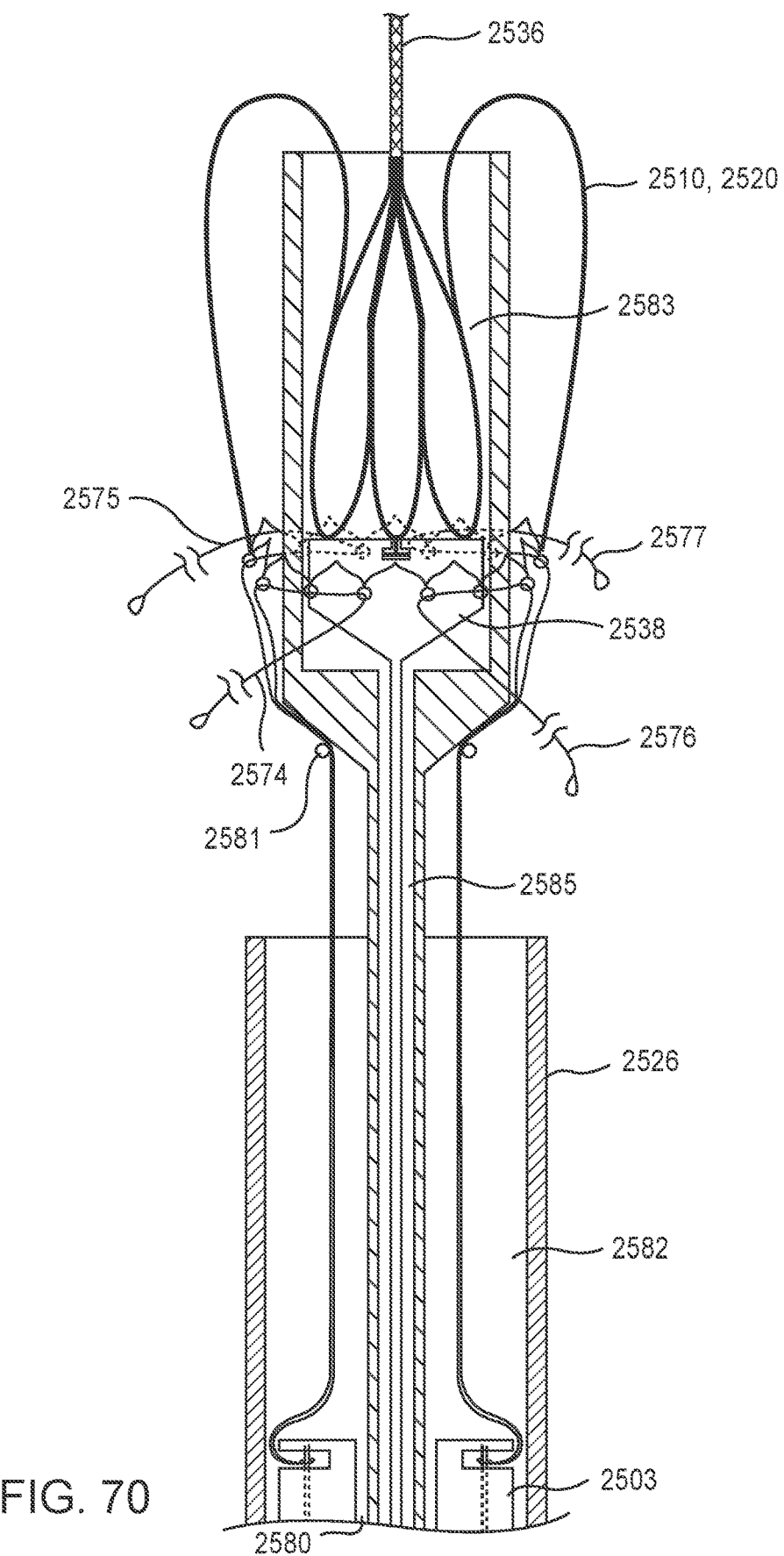
FIG. 70 is a partial cross-sectional side view of the delivery system and prosthetic heart valve of FIG. 63, shown in a third partially deployed configuration.

In addition, in some instances, the actuation wires 2574-2577 can assist in the articulation and placement of the valve 2500 into its destination (e.g., a native annulus of an atrioventricular valve of a heart). For example, as shown in FIG. 70, the actuation wires 2574-2577 can also be used to constrain, collapse, or otherwise move the valve 2500 (e.g., radially compress the outer frame 2520 of the valve 2500) after the valve 2500 exits the outer sheath 2526 and is in its reverted, expanded or partially expanded configuration. More specifically, in this embodiment, the tube member 2503 with the actuation wires 2574-2577 pinned thereto, can be manipulated by a user to move or urge the outer frame to a more compressed configuration (as shown in FIG. 70) by pulling or moving the tube member 2503 proximally. This may be desirable, for example, to reposition the valve 2500 within the heart before fully deploying the valve 2500.

Referring back to FIG. 69, when the outer frame 2520 of the valve 2500 is disposed in its non-inverted and at least partially expanded configuration, and is in a desired position within the heart, the inner frame 2550 can be deployed. As described above for valve 2100, to decouple the inner frame 2550 from the valve holder 2538, the valve holder 2538 can be moved distally and/or the inner sheath 2508 can be moved proximally such that the valve holder 2538 is disposed outside of the lumen 2583 of the inner sheath 2508. As such, the couplers 2506 can be released from the recesses 2504 releasing or decoupling the inner frame 2550 from the valve holder 2538. In some embodiments, the tether 2536 can be pulled to help move the inner frame 2550 outside of the inner sheath 2508. When the inner frame 2550 is released from the valve holder 2538 and disposed outside the inner sheath 2508, the inner frame 2550 can assume its biased expanded configuration.

Figure 71:
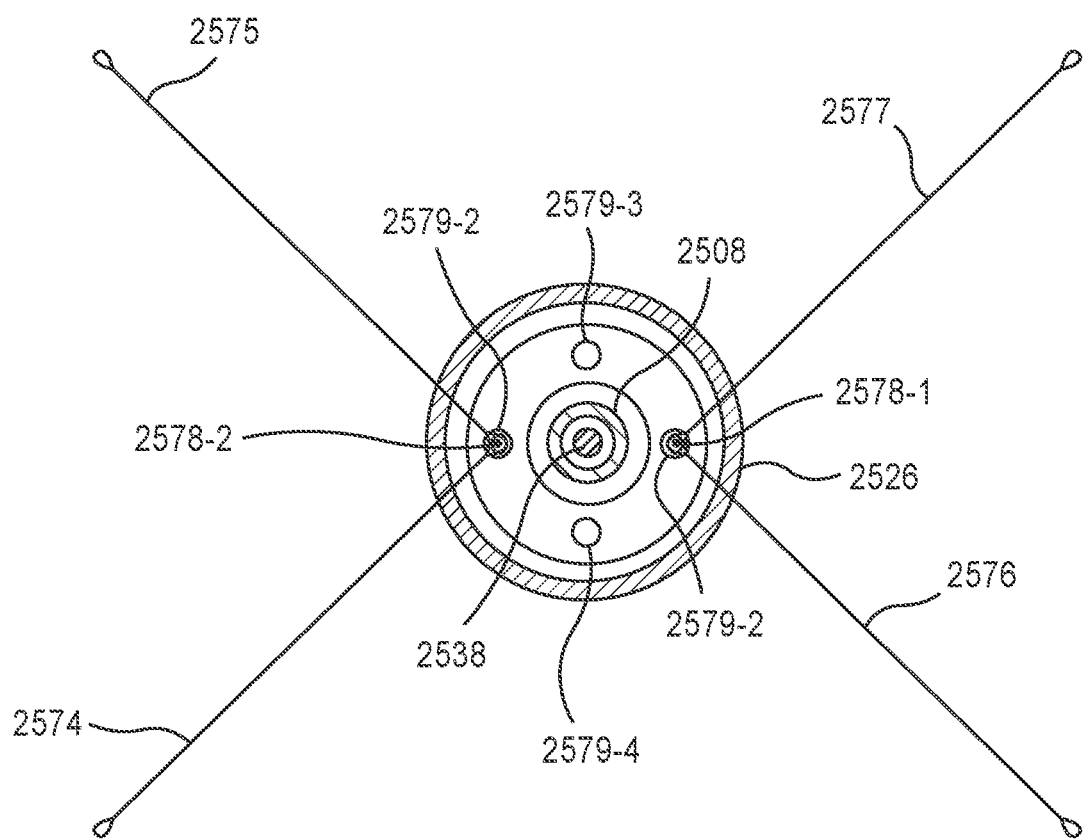
FIG. 71 is a cross-sectional view taken along line A-A in FIG. 63 showing the actuation wires in a partially released position.

The actuation wires 2574-2577 can also be released or decoupled from the outer frame 2520 before or after the inner frame 2550 is released form the valve holder 2538. To decouple the actuation wires 2574-2577 from the outer frame 2520, one end of each of the actuation wires 2574-2577 can be unpinned or decoupled from the tubular member 2503. For example, as shown in FIG. 71, the pinning member 2578-3 (See FIG. 64) can be withdrawn proximally from groove 2584 such that the second end of the actuation wire 2577 and the second end of the actuation wire 2575 are each released or unpinned from the tube member 2503, but remain pinned by pinning members 2578-2 and 2578-1, respectively. Similarly, the pinning member 2578-4 (see FIG. 64) can be withdrawn proximally from groove 2584 such that the second end of the actuation wire 2574 and the second end of actuation wire 2576 can each be released or unpinned from the tube member 2503, but remain pinned by pinning members 2578-2 and 2578-1, respectively. With one end of each of the actuation wires 2575-2577 coupled to the tube member 2503 (via pinning members 2578-1 and 2578-2 in this example), the tube member 2503 can be pulled proximally, which in turn will pull the opposite ends of the actuation wires 2574-2577 out of the loops 2562 of outer frame 2520. Thus with the actuation wires 2574-2577 detached from the outer frame 2520, the outer frame can assume a biased expanded or partially expanded configuration.

Although in the above example, the pinning members 2578-3 and 2578-4 are shown withdrawn to release the ends of the actuation wires 2574-2577, alternatively, the pinning members 2578-1 and 2578-2 can be withdrawn leaving the actuation wires 2574-2577 pinned by pinning members 2578-3 and 2578-4. Further, the actuation wires 2574-2577 can be decoupled from the outer frame 2520 at any suitable sequence or time period within the procedure. For example, in some instances it may be desirable for the actuation wires 2574-2577 to be released after the valve 2500 has at least partially exited the delivery sheath 2526 but before the valve 2500 is seated within the native annulus of the atrioventricular valve. In other instances, for example, the actuation wires 2574-2577 can be released after the valve 2500 has at least partially exited the outer delivery sheath 2526 and after the valve 2500 is seated within the native annulus of the atrioventricular valve.

Figure 72:
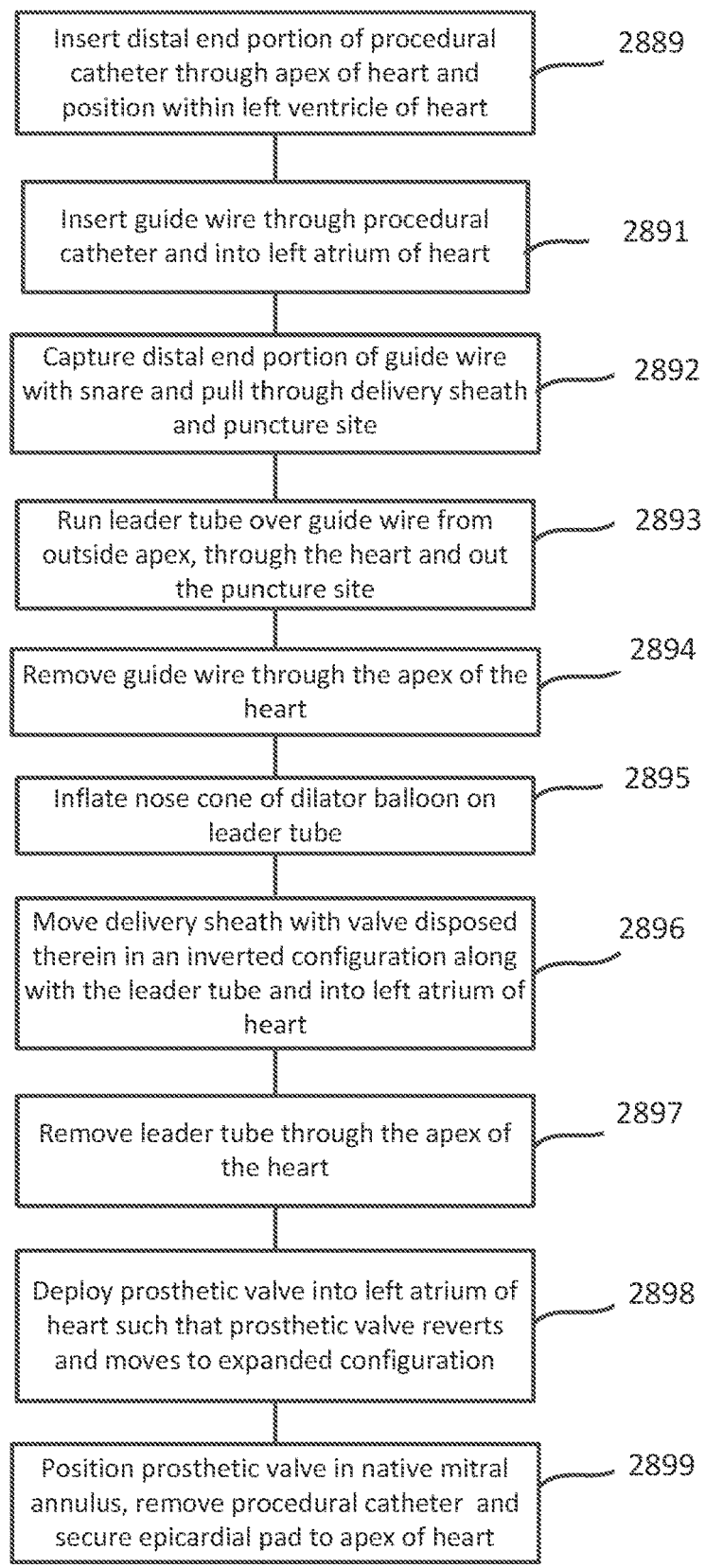
FIG. 72 is a flowchart illustrating a method of delivering and deploying a prosthetic mitral valve within a heart.

FIG. 72 is a flowchart illustrating a method of delivering and deploying a prosthetic mitral valve within a heart. The method includes at 2889, inserting a distal end portion of a procedural catheter through a puncture site at the apex of the heart, and positioning the distal end within the left ventricle of heart. At 2891, a guide wire is inserted through the procedural catheter and a distal end of the guide wire is moved into the left atrium of the heart. At 2892, a distal end portion of the guide wire is captured with a snare and pulled through a delivery sheath. The delivery sheath can be inserted through a puncture site, for example, in the femoral vein as described above with reference to FIGS. 43-48. In some embodiments, the delivery sheath can be inserted through a different puncture site and inserted transatrially (i.e., directly into the left atrium) or transjugularly. At 2893, a leader tube is moved or run over the guide wire from outside the apex, through the heart and out the puncture site. At 2894, the guide wire can be removed through the apex puncture site on the heart. At 2895, the nose cone of a balloon dilator member on the leader tube can be inflated.

At 2896, the delivery sheath with a prosthetic valve disposed therein in an inverted configuration along with the leader tube are moved into the left atrium of the heart. For example, the outer frame of the valve is in an inverted configuration relative to the inner frame of the valve. At 2897, the leader tube can be removed through the apex puncture site of the heart. At 2898, the prosthetic valve is deployed into the left atrium of the heart such that prosthetic valve reverts and assumes a biased expanded configuration. For example, in some embodiments, the outer frame of the valve can be moved to an un-inverted or expanded configuration relative to the inner frame by actuating actuation wires coupled to the outer frame. At 2899, the prosthetic valve is positioned within the native mitral annulus, the procedural catheter can be removed and an epicardial pad is secured to the apex of the heart.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

For example, although not specifically described for each embodiment, any to the embodiments of a delivery system can include a dilator device or member such as balloon dilator member 1711 shown and described with respect to FIGS. 43-48 and the method of delivery of FIG. 72. Further, the prosthetic heart valves described herein can be secured to a heart using an epicardial pad device as described with respect to FIGS. 43-48 and 72.

Further, although not shown, any of the embodiments of a delivery device or system can include a handle or handle assembly to which the various delivery sheaths and components can be operatively coupled and which a user (e.g., physician) can grasp and use to manipulate the delivery device or system.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via the jugular or femoral vein.

What is claimed is:

1. An apparatus, comprising:
    a prosthetic heart valve including an inner frame and an outer frame coupled to the inner frame at a plurality of coupling joints, the plurality of coupling joints configured to allow the outer frame to be moved relative to the inner frame such that the prosthetic valve can be moved between a first configuration and a second configuration, a plurality of prosthetic valve leaflets being coupled to the inner frame and adapted to allow blood to flow from an inflow end of the prosthetic heart valve toward an outflow end of the prosthetic heart valve but to substantially block blood from flowing from the outflow end of the prosthetic heart valve toward the inflow end of the prosthetic heart valve,
    the outer frame having an outer frame coupling portion coupled to the inner frame at the plurality of coupling joints and an outer frame free end portion, the inner frame having an inner frame coupling portion coupled to the outer frame at the plurality of coupling joints and an inner frame free end portion,
    the outer frame free end portion and the inner frame free end portion each opening in the same direction toward the inflow end of the prosthetic heart valve when the prosthetic valve is in the first configuration, the outer frame free end portion and the inner frame free end portion opening in opposite directions when the prosthetic valve is in the second configuration, and
    a delivery sheath configured to receive the prosthetic heart valve in the second configuration,
    wherein the inner frame and the outer frame are each formed of shape memory material so that the inner frame and the outer frame are each compressible and self-expandable,
    wherein upon the prosthetic heart valve transitioning from the second configuration to the first configuration, the outer frame is configured to invert relative to the inner frame and the delivery sheath.

2. The apparatus of claim 1, wherein each coupling joint from the plurality of coupling joints includes a living hinge disposed between the inner frame and the outer frame, the living hinge including a hinge member formed with one of a polymer, a tissue and a superelastic material.

3. The apparatus of claim 2, wherein the hinge member is coupled to the inner frame and coupled to the outer frame with one or more strands of suture.

4. The apparatus of claim 1, wherein each coupling joint from the plurality of coupling joints includes a tab disposed on the inner frame interlocked within a slot defined by the outer frame.

5. The apparatus of claim 1, wherein each coupling joint from the plurality of coupling joints includes at least one strand of suture wrapped through at least one of an opening defined in the inner frame and an opening defined in the outer frame.

6. The apparatus of claim 1, wherein each coupling joint from the plurality of coupling joints includes a pin disposed through an opening defined by the inner frame and an opening defined by the outer frame.

7. The apparatus of claim 6, wherein each coupling joint from the plurality of coupling joints further includes an interface element disposed between the inner frame and the outer frame.

8. The apparatus of claim 1, wherein each coupling joint from the plurality of coupling joints includes at least one tether inserted through at least one opening defined in the inner frame and at least one opening defined in the outer frame.

9. An apparatus, comprising:
    a prosthetic heart valve including an inner frame and an outer frame coupled to the inner frame at a plurality of coupling joints, the plurality of coupling joints configured to allow the outer frame to be moved relative to the inner frame such that the prosthetic valve can be moved between a first configuration and a second configuration, the prosthetic valve including a plurality of prosthetic valve leaflets being coupled to the inner frame and adapted to allow blood to flow from an inflow end of the prosthetic heart valve toward an outflow end of the prosthetic heart valve but to substantially block blood from flowing from the outflow end of the prosthetic heart valve toward the inflow end of the prosthetic heart valve,
    the outer frame having an outer frame coupling portion coupled to the inner frame at the plurality of coupling joints and an outer frame free end portion, the inner frame having an inner frame coupling portion coupled to the outer frame at the plurality of coupling joints, a first end portion and an inner frame free end portion on an opposite end of the inner frame from the first end portion,
    the plurality of coupling joints being disposed between the outer frame free end portion and the first end portion of the inner frame when the prosthetic valve is in the first configuration, the plurality of coupling joints being disposed between the inner frame free end portion and the outer frame free end portion when the prosthetic valve is in the second configuration, the outer frame free end portion and the inner frame free end portion each opening toward the inflow end of the prosthetic heart valve in the first configuration, and
    a delivery sheath configured to receive the prosthetic heart valve in the second configuration,
    wherein the inner frame and the outer frame are each formed of shape memory material so that the inner frame and the outer frame are each compressible and self-expandable, wherein upon the prosthetic heart valve transitioning from the second configuration to the first configuration, the outer frame is configured to invert relative to the inner frame and the delivery sheath.

10. The apparatus of claim 9, wherein each coupling joint from the plurality of coupling joints includes a living hinge disposed between the inner frame and the outer frame, the living hinge including a hinge member formed with one of a polymer, a tissue and a superelastic material.

11. The apparatus of claim 10, wherein the hinge member is coupled to the inner frame and coupled to the outer frame with one or more strands of suture.

12. The apparatus of claim 9, wherein each coupling joint from the plurality of coupling joints includes a tab disposed on the inner frame interlocked within a slot defined by the outer frame.

13. The apparatus of claim 9, wherein each coupling joint from the plurality of coupling joints includes at least one strand of suture wrapped through at least one of an opening defined in the inner frame and an opening defined in the outer frame.

14. The apparatus of claim 9, wherein each coupling joint from the plurality of coupling joints includes a pin disposed through an opening defined by the inner frame and an opening defined by the outer frame.

15. The apparatus of claim 14, wherein each coupling joint from the plurality of coupling joints further includes an interface element disposed between the inner frame and the outer frame.

16. The apparatus of claim 9, wherein each coupling joint from the plurality of coupling joints includes at least one tether inserted through at least one opening defined in the inner frame and at least one opening defined in the outer frame.

17. The apparatus of claim 9, wherein each coupling joint from the plurality of coupling joints includes at least one tether inserted through at least one of an opening defined in the inner frame or an opening defined in the outer frame, and a living hinge member coupled to the inner frame and coupled to the outer frame.

18. The apparatus of claim 9, wherein the outer frame includes a first frame portion and a second frame portion, the first frame portion is coupled to the inner frame at the plurality of coupling joints, the second frame portion is coupled to the first frame portion with a plurality of first outer frame coupling joints, the plurality of first outer frame coupling joints configured to allow the first frame portion to move relative to the second frame portion.

19. The apparatus of claim 18, wherein the outer frame includes a third frame portion, the third frame portion is coupled to the second frame portion at a plurality of second outer frame coupling joints, the plurality of second outer frame coupling joints configured to allow the third frame portion to move relative to the second frame portion.

20. An apparatus, comprising:
a prosthetic heart valve including an inner frame and an outer frame coupled to the inner frame at a plurality of coupling joints, the prosthetic valve being movable between a first configuration and a second configuration, the prosthetic valve including a plurality of prosthetic valve leaflets being coupled to the inner frame and adapted to allow blood to flow from an inflow end of the prosthetic heart valve toward an outflow end of the prosthetic heart valve but to substantially block blood from flowing from the outflow end of the prosthetic heart valve toward the inflow end of the prosthetic heart valve, the plurality of coupling joints configured to allow the outer frame to be moved between a first position relative to the inner frame and a second position relative to the inner frame in which the outer frame is inverted relative to the inner frame, an outer frame free end portion and an inner frame free end portion each opening toward the inflow end of the prosthetic heart valve in the first configuration,
the prosthetic valve being in the first configuration when the outer frame is in the first position,
the prosthetic valve being in the second configuration when the outer frame is in the second position, and
a delivery sheath configured to receive the prosthetic heart valve in the second configuration,
wherein the inner frame and the outer frame are each formed of shape memory material so that the inner frame and the outer frame are each compressible and self-expandable,
wherein upon the prosthetic heart valve transitioning from the second configuration to the first configuration, the outer frame is configured to invert relative to the inner frame and the delivery sheath.

21. The apparatus of claim 20, wherein the prosthetic valve is movable to a third configuration when disposed within a lumen of a delivery sheath while in the second configuration, the prosthetic valve defining a smaller outer perimeter when in the third configuration than in the second configuration and when in the first configuration.

22. The apparatus of claim 20, wherein the inner frame and the outer frame collectively define a first length when the prosthetic valve is in the first configuration and a second length when the prosthetic valve is in the second configuration, the second length being greater than the first length, a length of the inner frame being the same when the prosthetic valve is in the first configuration and when the prosthetic valve is in the second configuration.

23. The apparatus of claim 20, wherein the plurality of coupling joints are configured to allow the outer frame to be rotated relative to the inner frame to move the outer frame between the first position and the second position.

24. The apparatus of claim 20, wherein the plurality of coupling joints are configured to allow the outer frame to be pivotally moved relative to the inner frame to move the outer frame between the first position and the second position.

25. The apparatus of claim 20, wherein the outer frame axially overlaps the inner frame a first portion of the length of the outer frame when the prosthetic valve is in the first configuration, the outer frame axially overlaps the inner frame a second portion of the length of the outer frame when the prosthetic valve is in the second configuration, the first portion being greater than the second portion.

26. An apparatus comprising:
a prosthetic valve including an inner frame and an outer frame coupled to the inner frame at a plurality of coupling joints, the plurality of coupling joints configured to allow the outer frame to be moved relative to the inner frame such that the prosthetic valve can be moved between a first configuration and a second configuration, the prosthetic valve including a plurality of prosthetic valve leaflets being coupled to the inner frame and adapted to allow blood to flow from an inflow end of the prosthetic valve toward an outflow end of the prosthetic valve but to substantially block blood from flowing from the outflow end of the prosthetic valve toward the inflow end of the prosthetic valve, the outer frame and the inner frame collectively defining a first length of the prosthetic valve when the prosthetic valve is in the first configuration and a second length of the prosthetic valve when the prosthetic valve is in the second configuration, the second length being greater than the first length, an outer frame free end portion and an inner frame free end portion each opening toward the inflow end of the prosthetic valve in the first configuration, the inner frame having a length, the length of the inner frame being the same when the prosthetic valve is in both the first configuration and the second configuration, and a delivery sheath configured to receive the prosthetic valve in the second configuration, wherein the inner frame and the outer frame are each formed of shape memory material so that the inner frame and the outer frame are each compressible and self-expandable, wherein upon the prosthetic valve transitioning from the second configuration to the first configuration, the outer frame is configured to invert relative to the inner frame and the delivery sheath.

* * * * *